(12) United States Patent
Bombard et al.

(10) Patent No.: US 9,622,748 B2
(45) Date of Patent: Apr. 18, 2017

(54) ANASTOMOSIS SYSTEM WITH FLEXIBLE SHAFT

(75) Inventors: David L. Bombard, San Francisco, CA (US); Jaime S. Vargas, Menlo Park, CA (US); James T. Nielsen, San Francisco, CA (US); Phillipe R. Manoux, San Francisco, CA (US); Tenny Chang, Mountain View, CA (US); Stephen A. Yencho, Menlo Park, CA (US); Bernard A. Hausen, Menlo Park, CA (US); Brendan M. Donohoe, San Francisco, CA (US); Theodore M. Bender, San Francisco, CA (US); Nathan H. White, Palo Alto, CA (US); Bryan D. Knodel, Flagstaff, AZ (US)

(73) Assignee: DEXTERA SURGICAL INC., Redwood City, CA (US)

( * ) Notice: Subject to any disclaimer, the term of this patent is extended or adjusted under 35 U.S.C. 154(b) by 0 days.

(21) Appl. No.: 11/378,127

(22) Filed: Mar. 17, 2006

(65) Prior Publication Data

US 2006/0241660 A1    Oct. 26, 2006

Related U.S. Application Data

(63) Continuation of application No. 10/392,336, filed on Mar. 19, 2003, now Pat. No. 7,766,924, which is a (Continued)

(51) Int. Cl.
*A61B 17/115* (2006.01)
*A61B 17/04* (2006.01)
(Continued)

(52) U.S. Cl.
CPC ....... *A61B 17/1152* (2013.01); *A61B 17/0469* (2013.01); *A61B 17/072* (2013.01);
(Continued)

(58) Field of Classification Search
CPC . A61B 17/068; A61B 17/11; A61B 17/07207; A61B 17/07292;
(Continued)

(56) References Cited

U.S. PATENT DOCUMENTS 3,252,643 A * 5/1966 Strekopytov ........ A61B 17/072
227/109
3,254,650 A   6/1966 Collito
(Continued)

FOREIGN PATENT DOCUMENTS

DE    69406845    4/1998
DE    19732234    1/1999
(Continued)

OTHER PUBLICATIONS

"510(k) Notification for the Cardica C-Port Anastomosis System", Section 9, "Substantial Equivalence," and Appendices B, C, E, (Unpublished), No Date.
(Continued)

*Primary Examiner* — Diane Yabut
(74) *Attorney, Agent, or Firm* — Vista IP Law Group, LLP

(57) ABSTRACT

A surgical tool for performing anastomosis may include a handle and a tissue effector connected by a shaft, at least party of which may be flexible. The tissue effector may include a staple holder connected to an anvil.

19 Claims, 49 Drawing Sheets

Related U.S. Application Data continuation-in-part of application No. 10/151,441, filed on May 20, 2002, now Pat. No. 7,285,131, which is a continuation-in-part of application No. 09/363,255, filed on Jul. 28, 1999, now Pat. No. 6,391,038.

(51) Int. Cl.

| | | |
|---|---|---|
| A61B 17/072 | (2006.01) | |
| A61B 17/122 | (2006.01) | |
| A61B 17/00 | (2006.01) | |
| A61B 17/11 | (2006.01) | |
| A61F 2/06 | (2013.01) | |
| A61B 90/00 | (2016.01) | |

(52) U.S. Cl.
CPC ... *A61B 17/122* (2013.01); *A61B 2017/00243* (2013.01); *A61B 2017/07285* (2013.01); *A61B 2017/1107* (2013.01); *A61B 2017/1135* (2013.01); *A61B 2090/037* (2016.02); *A61F 2/064* (2013.01)

(58) Field of Classification Search
CPC .......... A61B 17/07285; A61B 17/0684; A61B 2017/07285
USPC .................................................. 606/139, 153
See application file for complete search history.

(56) References Cited

U.S. PATENT DOCUMENTS

| | | |
|---|---|---|
| 3,254,651 A | 6/1966 | Collito |
| 3,519,187 A | 7/1970 | Kapitanov et-al. |
| 3,618,842 A | 11/1971 | Bryan |
| 3,774,615 A | 11/1973 | Lim et al. |
| 3,795,034 A * | 3/1974 | Strekopytov et al. ...... 227/178.1 |
| 3,949,924 A | 4/1976 | Green |
| 4,076,162 A | 2/1978 | Kapitanov et al. |
| 4,214,587 A | 7/1980 | Sakura, Jr. |
| 4,241,861 A | 12/1980 | Fleischer |
| 4,248,267 A | 2/1981 | Brandenberg |
| 4,318,313 A | 3/1982 | Tartaglia et al. |
| 4,331,277 A | 5/1982 | Green |
| 4,350,160 A | 9/1982 | Kolesov et al. |
| 4,352,358 A | 10/1982 | Angelchik |
| 4,354,628 A * | 10/1982 | Green ............................ 227/19 |
| 4,366,819 A | 1/1983 | Kaster |
| 4,368,736 A | 1/1983 | Kaster |
| 4,485,811 A | 12/1984 | Chernousov et al. |
| 4,503,568 A | 3/1985 | Madras |
| 4,523,592 A | 6/1985 | Daniel |
| 4,553,542 A | 11/1985 | Schenck et al. |
| 4,593,693 A | 6/1986 | Schenck |
| 4,603,693 A | 8/1986 | Conta et al. |
| 4,605,001 A | 8/1986 | Rothfuss et al. |
| 4,607,637 A | 8/1986 | Berggren et al. |
| 4,610,383 A * | 9/1986 | Rothfuss et al. ............... 227/19 |
| 4,617,928 A * | 10/1986 | Alfranca .................... 227/180.1 |
| 4,624,255 A | 11/1986 | Schenck et al. |
| 4,624,257 A | 11/1986 | Berggren et al. |
| 4,633,874 A | 1/1987 | Chow et al. |
| 4,657,019 A | 4/1987 | Walsh et al. |
| 4,665,906 A | 5/1987 | Jervis |
| 4,665,916 A * | 5/1987 | Green ........................ 227/178.1 |
| 4,747,407 A | 5/1988 | Liu et al. |
| 4,752,024 A | 6/1988 | Green et al. |
| 4,773,420 A | 9/1988 | Green |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,938,408 A | 7/1990 | Bedi |
| 4,951,861 A | 8/1990 | Schulze et al. |
| 5,005,749 A | 4/1991 | Aranyi |
| 5,018,657 A | 5/1991 | Pedlick et al. |
| 5,062,842 A | 11/1991 | Tiffany |
| 5,104,025 A | 4/1992 | Main et al. |
| 5,119,983 A | 6/1992 | Green et al. |
| 5,156,310 A | 10/1992 | Biedenharn |
| 5,156,613 A | 10/1992 | Sawyer |
| 5,156,619 A | 10/1992 | Ehrenfeld |
| 5,172,845 A | 12/1992 | Tejeiro |
| 5,178,634 A | 1/1993 | Ramos Martinez |
| 5,193,731 A | 3/1993 | Aranyi |
| 5,205,459 A | 4/1993 | Brinkerhoff et al. |
| 5,211,683 A | 5/1993 | Maginot |
| 5,234,447 A | 8/1993 | Kaster et al. |
| 5,250,058 A | 10/1993 | Miller et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,300,065 A | 4/1994 | Anderson |
| 5,304,220 A | 4/1994 | Maginot |
| 5,314,435 A | 5/1994 | Green et al. |
| 5,314,468 A | 5/1994 | Ramos Martinez |
| 5,333,773 A | 8/1994 | Main et al. |
| 5,336,233 A | 8/1994 | Chen |
| 5,350,104 A | 9/1994 | Main et al. |
| 5,364,389 A | 11/1994 | Anderson et al. |
| 5,366,462 A | 11/1994 | Kaster et al. |
| 5,376,095 A | 12/1994 | Ortiz |
| 5,392,979 A | 2/1995 | Green et al. |
| 5,395,030 A | 3/1995 | Kuramoto et al. |
| 5,417,361 A | 5/1995 | Williamson, IV |
| 5,431,322 A | 7/1995 | Green et al. |
| 5,443,497 A | 8/1995 | Venbrux |
| 5,447,514 A | 9/1995 | Gerry et al. |
| 5,452,836 A | 9/1995 | Huitema et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,465,896 A | 11/1995 | Allen et al. |
| 5,478,003 A | 12/1995 | Green et al. |
| 5,478,354 A | 12/1995 | Tovey et al. |
| 5,489,058 A | 2/1996 | Plyley et al. |
| 5,522,834 A | 6/1996 | Fonger et al. |
| 5,533,661 A | 7/1996 | Main et al. |
| 5,535,935 A | 7/1996 | Vidal et al. |
| 5,540,677 A | 7/1996 | Sinofsky |
| 5,558,667 A | 9/1996 | Yarborough et al. |
| 5,562,241 A | 10/1996 | Knodel et al. |
| 5,571,167 A | 11/1996 | Maginot |
| 5,580,067 A | 12/1996 | Hamblin et al. |
| 5,586,711 A | 12/1996 | Plyley et al. |
| 5,605,572 A | 2/1997 | Berger |
| 5,609,285 A | 3/1997 | Grant et al. |
| 5,611,794 A | 3/1997 | Sauer et al. |
| 5,620,452 A | 4/1997 | Yoon |
| 5,632,432 A | 5/1997 | Schulze et al. |
| 5,632,433 A | 5/1997 | Grant et al. |
| 5,636,780 A | 6/1997 | Green |
| 5,643,340 A | 7/1997 | Nunokawa |
| 5,653,373 A | 8/1997 | Green et al. |
| 5,655,698 A * | 8/1997 | Yoon ......................... 227/176.1 |
| 5,657,921 A | 8/1997 | Young et al. |
| 5,662,258 A | 9/1997 | Knodel et al. |
| 5,662,259 A | 9/1997 | Yoon |
| 5,665,085 A | 9/1997 | Nardella |
| 5,669,544 A | 9/1997 | Schulze et al. |
| 5,669,918 A | 9/1997 | Balazs et al. |
| 5,669,934 A | 9/1997 | Sawyer |
| 5,673,840 A | 10/1997 | Schulze et al. |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,369 A | 1/1998 | Vaitekunas et al. |
| 5,707,380 A | 1/1998 | Hinchliffe et al. |

(56) References Cited

U.S. PATENT DOCUMENTS

| | | |
|---|---|---|
| 5,709,693 A | 1/1998 | Taylor |
| 5,711,472 A | 1/1998 | Bryan |
| 5,725,544 A | 3/1998 | Rygaard |
| 5,749,893 A | 5/1998 | Vidal et al. |
| 5,749,895 A | 5/1998 | Sawyer et al. |
| 5,752,965 A | 5/1998 | Francis et al. |
| 5,776,130 A | 7/1998 | Buysse et al. |
| 5,779,132 A | 7/1998 | Knodel et al. |
| 5,797,537 A | 8/1998 | Oberlin et al. |
| 5,797,920 A | 8/1998 | Kim |
| 5,799,857 A | 9/1998 | Robertson et al. |
| 5,816,471 A | 10/1998 | Plyley et al. |
| 5,817,113 A | 10/1998 | Gifford, III et al. |
| 5,824,015 A | 10/1998 | Sawyer |
| 5,827,265 A | 10/1998 | Glinsky et al. |
| 5,827,271 A | 10/1998 | Buysse et al. |
| 5,833,690 A | 11/1998 | Yates et al. |
| 5,833,695 A | 11/1998 | Yoon |
| 5,833,698 A | 11/1998 | Hinchliffe et al. |
| 5,862,972 A | 1/1999 | Green et al. |
| 5,865,730 A | 2/1999 | Fox et al. |
| 5,878,938 A | 3/1999 | Bittner et al. |
| 5,879,371 A | 3/1999 | Gardiner et al. |
| 5,893,369 A | 4/1999 | Lemole |
| 5,904,697 A | 5/1999 | Gifford, III et al. |
| 5,913,866 A * | 6/1999 | Ginn et al. ................. 606/174 |
| 5,915,616 A | 6/1999 | Viola et al. |
| 5,918,791 A | 7/1999 | Sorrentino et al. |
| 5,921,995 A | 7/1999 | Kleshinski |
| 5,944,730 A | 8/1999 | Nobles et al. |
| 5,976,159 A | 11/1999 | Bolduc |
| 5,993,464 A | 11/1999 | Knodel |
| 6,004,335 A | 12/1999 | Vaitekunas et al. |
| 6,010,054 A | 1/2000 | Johnson |
| 6,015,416 A | 1/2000 | Stefanchik et al. |
| 6,024,748 A | 2/2000 | Manzo et al. |
| 6,036,700 A | 3/2000 | Stefanchik et al. |
| 6,039,733 A | 3/2000 | Buysse et al. |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |
| 6,071,289 A | 6/2000 | Stefanchik et al. |
| 6,083,234 A | 7/2000 | Nicholas et al. |
| 6,110,187 A | 8/2000 | Donlon |
| 6,117,148 A | 9/2000 | Ravo et al. |
| 6,176,413 B1 | 1/2001 | Heck et al. |
| 6,183,486 B1 * | 2/2001 | Snow et al. ................. 606/151 |
| 6,187,019 B1 | 2/2001 | Stefanchik |
| 6,193,129 B1 | 2/2001 | Bittner et al. |
| 6,193,734 B1 | 2/2001 | Bolduc et al. |
| 6,200,263 B1 | 3/2001 | Person |
| 6,209,773 B1 | 4/2001 | Bolduc et al. |
| 6,248,117 B1 | 6/2001 | Blatter |
| 6,250,532 B1 | 6/2001 | Green et al. |
| 6,254,617 B1 | 7/2001 | Spence et al. |
| 6,280,460 B1 | 8/2001 | Bolduc et al. |
| 6,391,038 B2 | 5/2002 | Vargas |
| 6,394,948 B1 | 5/2002 | Borst et al. |
| 6,398,797 B2 | 6/2002 | Bombard |
| 6,436,097 B1 | 8/2002 | Nardella |
| 6,461,365 B2 | 10/2002 | Bolduc et al. |
| 6,478,804 B2 | 11/2002 | Vargas |
| 6,514,263 B1 | 2/2003 | Stefanchik et al. |
| 6,520,973 B1 | 2/2003 | McGarry |
| 6,530,932 B1 | 3/2003 | Swayze |
| 6,551,334 B2 | 4/2003 | Blatter et al. |
| 6,569,173 B1 | 5/2003 | Blatter et al. |
| 6,601,749 B2 * | 8/2003 | Sullivan et al. ............ 227/180.1 |
| 6,623,494 B1 * | 9/2003 | Blatter ........................ 606/153 |
| 6,626,921 B2 | 9/2003 | Blatter et al. |
| 6,652,542 B2 | 11/2003 | Blatter et al. |
| 6,663,590 B2 | 12/2003 | Blatter |
| 6,712,831 B1 | 3/2004 | Kaplan et al. |
| 6,726,694 B2 | 4/2004 | Blatter et al. |
| 6,736,825 B2 | 5/2004 | Blatter et al. |
| 6,743,244 B2 | 6/2004 | Blatter et al. |
| 6,821,286 B1 | 11/2004 | Carranza et al. |
| 6,905,504 B1 | 6/2005 | Vargas |
| 6,942,675 B1 | 9/2005 | Vargas |
| 6,994,669 B1 | 2/2006 | Gannoe et al. |
| 6,994,714 B2 | 2/2006 | Vargas |
| 7,014,644 B1 | 3/2006 | Bombard |
| 7,063,712 B2 | 6/2006 | Vargas |
| 7,217,285 B2 | 5/2007 | Vargas |
| 7,285,131 B1 | 10/2007 | Bombard |
| 7,300,444 B1 | 11/2007 | Nielsen |
| 7,303,570 B2 | 12/2007 | Bombard |
| 7,371,243 B1 | 5/2008 | Nielsen |
| 7,682,368 B1 | 3/2010 | Bombard |
| 7,699,859 B2 | 4/2010 | Bombard |
| 7,766,924 B1 | 8/2010 | Bombard |
| 7,850,703 B2 | 12/2010 | Bombard |
| 8,475,474 B2 | 7/2013 | Bombard |
| 2001/0004698 A1 | 6/2001 | Blatter et al. |
| 2001/0023353 A1 | 9/2001 | Vargas et al. |
| 2001/0023354 A1 | 9/2001 | Blatter et al. |
| 2002/0095166 A1 | 7/2002 | Vargas et al. |
| 2003/0014064 A1 | 1/2003 | Blatter |
| 2004/0097994 A1 | 5/2004 | Blatter et al. |
| 2004/0225306 A1 | 11/2004 | Blatter et al. |
| 2005/0216043 A1 | 9/2005 | Blatter et al. |
| 2006/0167485 A1 | 7/2006 | Blatter |

FOREIGN PATENT DOCUMENTS

| | | |
|---|---|---|
| EP | 1354559 | 5/1995 |
| EP | 1354559 A2 | 5/1995 |
| EP | 0625335 B1 | 11/1997 |
| EP | 0820724 | 1/1998 |
| EP | 0885595 | 12/1998 |
| EP | 0938870 | 9/1999 |
| EP | 0820725 | 1/2000 |
| EP | 0990420 | 4/2000 |
| FR | 2316910 | 7/1976 |
| RU | 1667844 | 8/1991 |
| WO | WO-98/19625 | 5/1998 |
| WO | WO-99/11178 | 3/1999 |
| WO | WO-99/21491 | 5/1999 |
| WO | WO-00/12013 | 3/2000 |
| WO | WO 00/59380 | 10/2000 |

OTHER PUBLICATIONS

Ethicon Endo-Surgery, "Atlas of Surgical Stapling", (1999).
U.S. Appl. No. 12/715,268, filed Mar. 1, 2010, Surgical Staples Fragibly Connected to Staple Holding Strip, David L. Bombard.
U.S. Appl. No. 11/378,127, filed Mar. 17, 2006, Anastomosis System With Flexible Shaft, David L. Bombard.
U.S. Appl. No. 10/607,524, filed Jun. 26, 2003, Anastomosis System and Method for Controlling a Tissue Site, Tenny Chang.
U.S. Appl. No. 10/988,326, filed Nov. 12, 2004, Method for Anastomosing Vessels, David L. Bombard.
U.S. Appl. No. 11/332,611, filed Jan. 13, 2006, Adhesivse-Based Anastomosis Method and System, David L. Bombard.
U.S. Appl. No. 11/670,877, filed Feb. 2, 2007, Anastomosis Stapler, Jamie Vargas.
U.S. Appl. No. 11/756,260, filed May 31, 2007, Anastomosis System With Cutting Element, David L. Bombard.
U.S. Appl. No. 11/865,893, filed Oct. 2, 2007, Anastomosis System With Anvil Entry Hole Sealer, Jamey Neilsen.
U.S. Appl. No. 12/970,678, filed Dec. 16, 2010, Surgical Stapler With Direct Sled to Staple Contact, David L. Bombard.

* cited by examiner

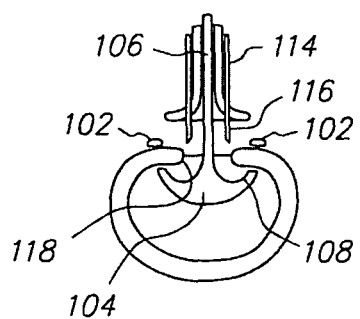
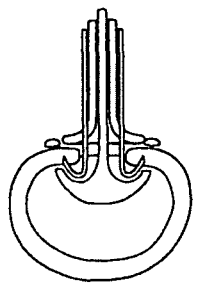
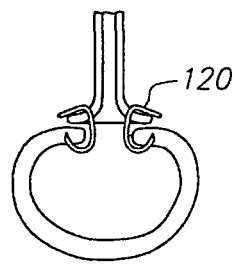
FIG. 20       FIG. 21       FIG. 22
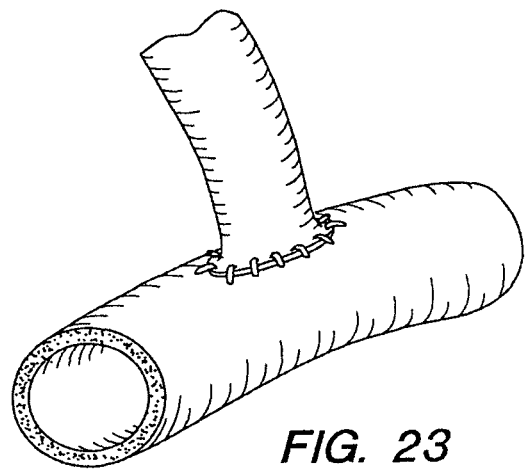
FIG. 23
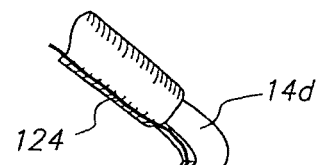
FIG. 24
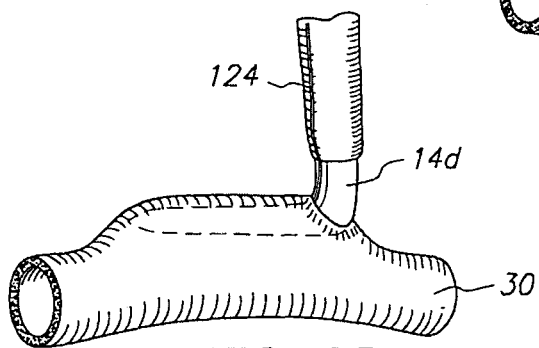
FIG. 25

ANASTOMOSIS SYSTEM WITH FLEXIBLE SHAFT

This application is a continuation of U.S. patent application Ser. No. 10/392,336, now U.S. Pat. No. 7,766,924, which in turn is a continuation-in-part of U.S. patent application Ser. No. 10/151,441, now U.S. Pat. No. 7,285,131, which in turn is a continuation-in-part of U.S. Pat. No. 6,391,038, all of which are hereby incorporated by reference in their entirety.

FIELD OF THE INVENTION

The invention relates to an apparatus and method for performing anastomosis.

BACKGROUND

Anastomosis is a procedure by which two hollow tissue structures are joined together. More particularly, vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart-lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patient's chest with the aid of visualizing scopes. In both conventional and less invasive CABG procedures, the surgeon has to suture one end of the graft vessel to the coronary artery and the other end of the graft vessel to a blood-supplying artery, such as the aorta. The suturing process is a time consuming and difficult procedure requiring a high level of surgical skill. In order to perform the suturing of the graft to a target vessel such as the coronary artery or the blood supplying artery, a surgeon holds the edges of the incision in the target vessel with one handle and holds a needle in the other hand for suturing, or an assistant may hold the edges of the incision in the target vessel while a surgeon makes small stitches as close as possible to the edges of the incision. This suturing requires a high degree of precision and is quite time consuming. In addition, during conventional CABG procedures blood flow at the anastomosis site is stopped during suturing. This prevents bleeding from the incision site but also prevents blood from reaching a portion of the heart muscle served by the vessel. Further, during off-pump CABG procedures a side clamp or other device may be used to isolate a portion of the wall of the aorta to which a graft vessel is sutured. The use of a side clamp or similar device can cause emboli to detach from the wall of the aorta and enter the bloodstream, which is undesirable.

Accordingly, it would be desirable to provide a vascular anastomosis system that allows the tissue at the anastomosis site to be controlled during suturing or other connection of the graft and target vessels. It would also be desirable to provide a vascular anastomosis system that allows the connection of a graft vessel to a target vessel prior to making an incision in the target vessel which allows blood flow between the target vessel and the graft vessel.

SUMMARY OF THE INVENTION

In one aspect of the invention, an anastomosis tool includes a tissue effector connected to a handle by a shaft or other structure. The tissue effector may be orientable relative to the handle and/or shaft. For example, the tissue effector may be configured to roll, pitch and/or yaw relative to the shaft. In this way, the tissue effector can be placed in a desired orientation at an anastomosis site, and the handle can be held in a convenient position by the user.

In another aspect of the invention, the tissue effector includes a staple holder moveable relative to an anvil. The staple holder holds at least one staple. The staple holder and the anvil are movable relative to one another, and move between an open position and a closed position. In the open position, the anvil is configured for insertion into a target vessel. The tissue effector may be biased to the open position with a spring or other mechanism or structure. In the closed position, the tissue effector holds the graft vessel against the wall of the target vessel.

In another aspect of the invention, the staple holder includes two or more spaced-apart arms. An end of the graft vessel is cut to form at least one flap therein, and each flap is folded onto an arm of the staple holder. One or more graft clips are provided on each arm, where each graft clip secures a corresponding flap to the surface of the arm. Each clip is configured to move between an open position for receiving a flap and a closed position for securing the flap to the corresponding arm of the staple holder. Each graft clip may utilize a cam-lock feature or other structure or mechanism to hold itself in the closed position. One or more spikes may be provided on each arm, such that the spike or spikes penetrate and hold the corresponding flap to secure it more thoroughly to the staple holder.

In another aspect of the invention, at least one of the arms of the staple holder includes at least one connector bay. A staple is held within each connector bay, such as by friction against its walls. One or more of the staples may be coated with sodium stearate or other biocompatible lubricant. A passage extends though each arm of the staple holder, where one end of each connector bay opens to that passage.

In another aspect of the invention, a connector deployer extends into each connector bay, such that one end of the connector deployer contacts or is in proximity to the corresponding staple. One end of each connector bay faces the anvil when the tissue effector is in the closed position, and the other end of each connector bay opens to a channel or other structure. The ends of the connector bays facing the anvil are against or in proximity to the flaps of the graft vessel held against the arms of the staple holder, such that deployment of the staples from the connector bays causes those staples to penetrate the flaps.

In another aspect of the invention, a ramp element is movable within each passage. The ramp element may be a component of a sled that is movable relative to the staple holder. Upon contacting a connector deployer, the ramp element urges it into the connector bay. In turn, that connector deployer urges the corresponding staple along the connector bay and out of the open end of the connector bay. As the ramp element translates along the channel, it sequentially encounters the connector deployers, thereby sequentially deploying the staples into the corresponding flap and into the wall of the target vessel. Alternately, at least one ramp element may be configured to deploy the staples in another manner, such as substantially simultaneously.

In another aspect of the invention, excess tissue may be incised from the flaps of the graft vessel. Such incising may be performed before, during or after the connection of the graft vessel to the target vessel. For example, a vein knife is configured to move relative to a second channel defined in an arm of the staple holder, where the second channel is positioned relative to the flap such that the flap can be to a desired size. Each flap may be incised during or after the anastomosis, freeing the graft vessel from the staple holder. The vein knife may be connected to the sled directly or indirectly. Thus, as the sled translates along the first channel, the vein knife translates along the second channel and incises the corresponding flap.

In another aspect of the invention, at least one graft clip blade optionally is attached to at least one of the arms of the staple holder. The graft clip blade has a serrated edge oriented to engage the corresponding flap of the graft vessel. The serrations on the edge of the graft clip blade assist in holding the corresponding flap securely, particularly as the vein knife incises excess tissue from the flap. Additionally, the graft clip blade may participate in incising excess tissue from the corresponding flap. Further, the serrations on the edge of the graft clip blade, in conjunction with the spikes, may assist in holding the excess tissue incised from each flap.

In another aspect of the invention, a cutter translates along a slot in the anvil to create an opening in the wall of the target vessel. The timing of the staple deployments are coordinated with the motion of the cutter. As one example, the sled and the cutter move simultaneously. The sled and the cutter are shaped, positioned and/or otherwise configured to connect the graft vessel to the target vessel and to incise an opening in the wall of the target vessel in a coordinated manner.

In another aspect of the invention, the distal end of one or more of the arms of the staple holder may be notched. After the staples have been deployed, the sled may be positioned such that its distal ends are located at the distal ends of the channels, such that the sled is visible via the notches. In this way, actuation of the sled and thus deployment of the staples can be visually confirmed.

In another aspect of the invention, the handle includes a trigger operationally connected to the tissue effector, providing for actuation of the tissue effector with a single motion of the trigger. That is, a single input to the anastomosis tool both deploys staples and incises the target vessel at the anastomosis site, such that a single input to the tool creates a complete anastomosis between the graft vessel and the target vessel.

In another aspect of the invention, the trigger is connected to a rocker that is configured to engage a proximal slider during actuation of the trigger. A first cable or other force transmission structure or mechanism is connected to the proximal slider, as well as to the anvil. The first cable is movable relative to a cable housing, which is fixed at one end to the staple holder and at the other end to the shaft. The anvil is fixed relative to the shaft as well. As the trigger is actuated, the rocker urges the proximal slider proximally, causing the proximal slider to pull the first cable proximally. Because the anvil is fixed relative to the shaft, the proximal motion of the first cable tensions the first cable. Because the cable housing is fixed to the staple holder, the tensioning of the first cable causes the staple holder to move closer to the anvil, thereby moving the tissue effector from the open position to the closed position. By moving the staple holder and keeping the anvil substantially stationary, the tissue effector closes without damaging the target vessel within which the anvil is positioned.

In another aspect of the invention, the rocker is configured to engage a distal slider during actuation of the trigger. A second cable or other force transmission structure or mechanism is connected to the distal slider, as well as to the sled. As the trigger is actuated, the rocker releases the distal slider to move proximally, causing the distal slider to pull the second cable proximally. The second cable is routed over a bend on the staple holder such that the motion of the second cable pulls the sled in the distal direction.

In another aspect of the invention, the flaps are decoupled from the tissue effector after the anastomosis is complete. Advantageously, this decoupling occurs as a result of the depression of the trigger, such that a single control is used to perform the entire anastomosis procedure. Decoupling may be performed by incising the flaps, by releasing the graft clips, or in any other appropriate manner.

BRIEF DESCRIPTION OF THE DRAWINGS

FIGS. 20-22 are side cross sectional views of the steps of performing the anastomosis with the continuous anastomosis staple shown in FIG. 19.

FIG. 23 is a perspective view of the completed anastomosis performed as shown in FIGS. 19-22.

FIGS. 24-27 are perspective views of the steps of an alternative anvil and clamp system for controlling an anastomosis site and forming an incision through the clamped tissue of the target vessel.

The use of the same reference symbols in different figures indicates similar or identical items.

DETAILED DESCRIPTION

Figure 1:
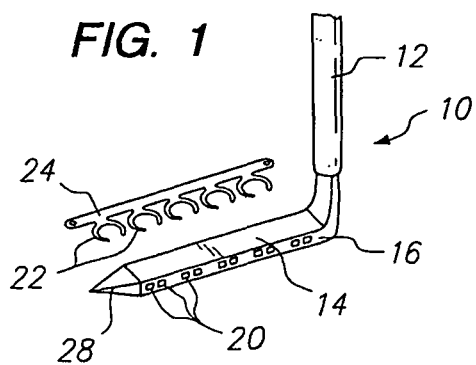
FIG. 1 is a perspective view of an anvil and a plurality of staples according to a first aspect of the present invention.

As shown in FIG. 1, one embodiment of an anvil 10 includes a handle 12 and an anvil arm 14 extending from the handle 12. The anvil arm 14 may be oriented substantially perpendicular to the handle 12, or oriented at a different angle. The anvil arm 14 may be provided with one or more staple bending features 16 on opposite sides of the anvil arm 14. In the anvil 10 shown in FIG. 1, the staple bending features 16 each include a plurality of recesses 20 which receive the ends of staples 22 and cause the staple ends to bend over. At least one of the staple bending features 16 may be configured differently or omitted, if desired. The staples 22 may be connected to a staple holding strip 24. The staples 22 are U-shaped and are arranged in a spaced apart parallel configuration such that the staples 22 all lie in a single plane. Alternately, the staples 22 may be shaped differently, and/or lie in one or more different planes. An exemplary anvil arm 14 has a height and a width of about 2 mm or less, advantageously about 1 mm or less, and a length of about 2 to 15 mm, advantageously 5 to 12 mm. The length of the anvil will vary depending on the diameter of the graft vessel selected. The length to width ratio of the anvil arm 14 is substantially between 2:1 and 15:1. A different length to width ratio may be used, if desired. As one example, the staples 22 have widths of about 0.2-3 mm. Advantageously, the staples 22 have widths of substantially 2 mm or less. The leg lengths of the staples 22 are substantially 0.2-3 mm. Alternately, other staple widths and/or leg lengths may be used.

Figure 2:
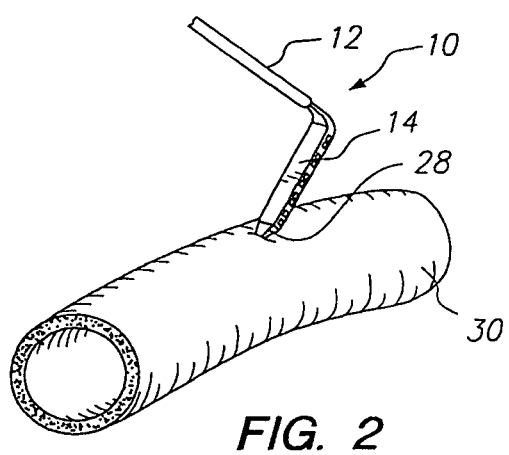
FIG. 2 is a perspective view of the anvil of FIG. 1 being inserted into a target vessel.

The anvil arm 14 has a sharp distal end 28 for puncturing the tissue of a target vessel to insert the anvil arm 14 into the target vessel. As illustrated in FIG. 2, the anvil arm 14 is inserted into a pressurized or unpressurized target vessel 30 by puncturing the target vessel with the distal end 28 of the anvil arm 14. The hole that is formed in the wall of the target vessel 30 by the anvil arm 14 is small enough to prevent significant bleeding through the puncture site. Alternately, the hole is closed by hand suturing. Alternately, the hole is closed with a biocompatible glue, adhesive or the like. Alternately, the hole is closed with a clip, clamp, or other implantable device that remains on the target vessel. Such a device may be positioned on the outer surface and/or inner surface of the target vessel, and may extend into the hole. A device for closing the hole may be constructed from nitinol or other superelastic or pseudoelastic material, or from stainless steel or other material, where that device moves between a first configuration and a second configuration during deployment, and where the second configuration holds the hole closed. The hole is less than substantially 2 mm wide, and advantageously less than 1 mm wide. Alternately, the anvil arm 14 has a blunt distal end 28 that is inserted through a hole created with a separate instrument, by a different instrument connected to the anvil arm 14, or by a sharp member connected to the anvil arm 14 that can be retracted into the anvil arm 14 or otherwise blunted or concealed after puncturing or creating an incision in the wall of the target vessel.

Figure 3:
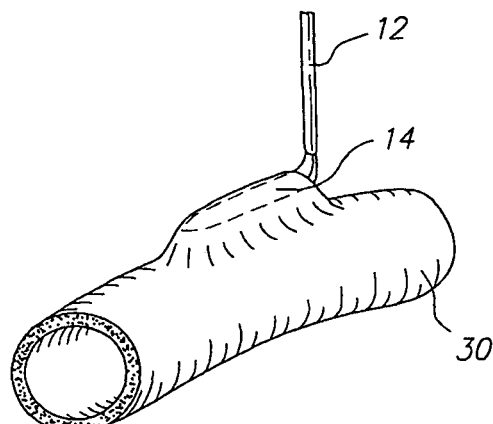
FIG. 3 is a perspective view of the anvil tenting a wall of a target vessel for an anastomosis procedure.

Once the anvil arm 14 has been inserted into the target vessel 30, the anvil arm 14 may be pulled against an inner wall of the target vessel 30, causing tenting of the thin tissue of the vessel wall as illustrated in FIG. 3. This tenting of the vessel wall provides control over the anastomosis site during an anastomosis procedure that is described with respect to FIGS. 4-6. However, tenting of the target vessel wall need not be tented in order to control the anastomosis site during the anastomosis procedure.

Figure 4:
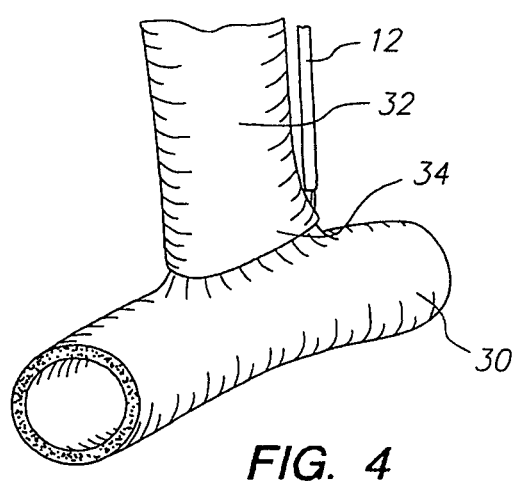
FIG. 4 is a perspective view of a graft vessel placed adjacent an exterior of the tented target vessel for the anastomosis procedure.
Figure 5:
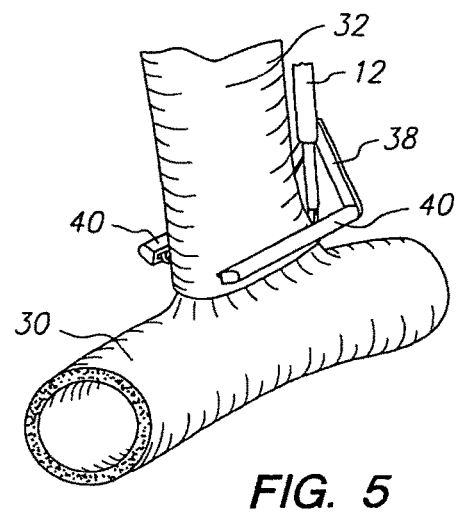
FIG. 5 is a perspective view of the staples being applied to the graft vessel and the target vessel during an anastomosis procedure.
Figure 29:
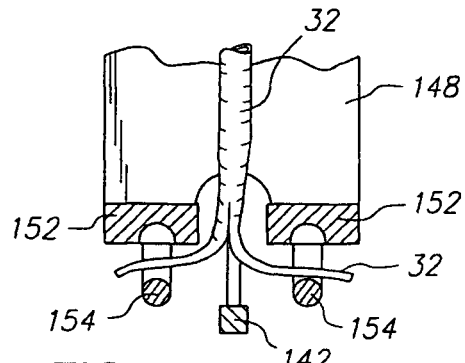
FIG. 29 is a cross sectional view taken along line C-C of FIG. 28, showing a first step of the anastomosis procedure.
Figure 30:
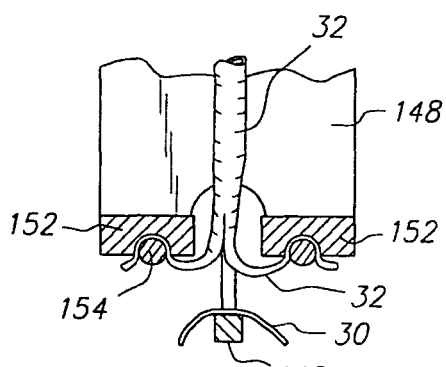
FIG. 30 is a cross sectional view taken along line C-C of FIG. 28, showing a second step of the anastomosis procedure.
Figure 31:
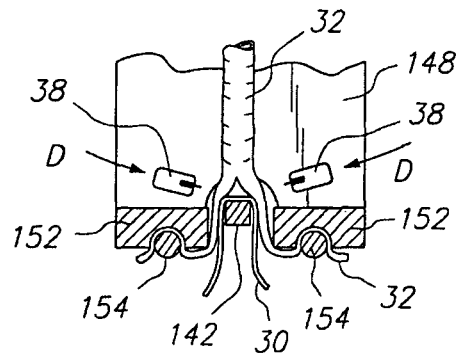
FIG. 31 is a cross sectional view taken along line C-C of FIG. 28, showing a third step of the anastomosis procedure.

As shown in FIG. 4, a graft vessel 32 is advanced to the anastomosis site and an end 34 of the graft vessel 32 is positioned adjacent an exterior surface of the target vessel 30 at the anastomosis site. The tented portion of the target vessel 30 is positioned within the perimeter of the end 34 of the graft vessel 32. As shown in FIG. 5, a staple holder 38 is provided having two arms 40 which are pivotally connected to the handle 12 of the anvil 10. Alternatively, the pivoting arms 40 of the staple holder 38 may be connected to the handle 12 in a different way, or may be connected to a separate or additional device. The arms 40 are spaced apart from one another across at least a part of their length. Thus, the graft vessel can be positioned between the arms 40. That is, the arms 40 are positioned on substantially opposite sides of the graft vessel. In this way, each arm 40 may be positioned against a flap at an end of the graft vessel, as illustrated in FIGS. 29-31. The arms 40 may be configured differently, if desired.

Figure 6:
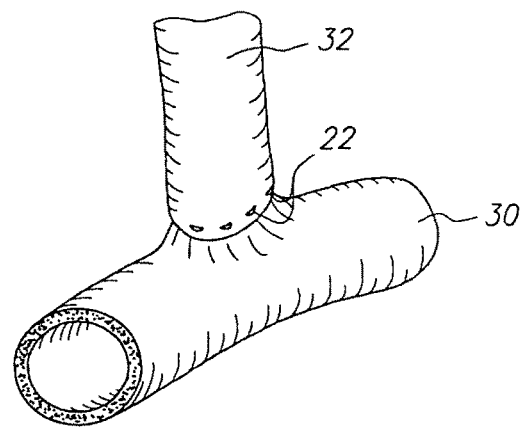
FIG. 6 is a perspective view of the completed anastomosis according to the first aspect of the present invention.

Referring also to FIG. 1, the staple holder 38 may be used to hold individual staples 22 and/or staple holding strips 24. In one embodiment, each arm 40 of the staple holder 38 carries one row of staples 22 or one staple holding strip 24, where the staples 22 are arranged in a substantially linear row. Alternately, staples 22 or staple strips 24 may be arranged in two or more rows, parallel or otherwise, on one or more arms 40. Alternately, the staples 22 may be staggered on one or more arms, such that at least one row of staples 22 does not fall along a straight line. The staples 22 or staple strips 24 may be arranged or aligned in any manner on each arm 40 that results in a secure anastomosis between the graft vessel and the target vessel. The staples 22 are inserted through the flaps at the end of the graft vessel 32, or another portion of the target vessel, and into the target vessel 30 by pivoting the arms 40 of the staple holder 38 towards the anvil arm 14. The staple bending features 16 are positioned in a configuration corresponding to the configuration of the staples 22, such that each staple 22 engages a corresponding staple bending feature 16 during deployment. When the ends of the staples 22 engage the staple bending features 16 on the anvil arm 14, the ends of the staples 22 are bent over, securing the graft vessel 32 and target vessel 30 together. Once the staple ends are bent over, the staples 22 are released from the staple holding strip 24 or the staple holder 38, resulting in spaced apart staples 22 securing the graft vessel 32 and the target vessel 30 together as shown in FIG. 6. Alternately, the staple holder 38 is a mechanism that deploys connectors other than or in addition to staples 22.

After stapling is complete, an incision is formed in the wall of the target vessel 30 to allow blood flow between the target vessel and the graft vessel 32. Some examples of methods and devices for forming the incision will be described in further detail below. FIG. 6 illustrates a completed anastomosis between a target vessel 30 and a graft vessel 32 with a plurality of staples 22. The spacing between the staples 22 is approximately 1 to 4 mm. This spacing is similar to the spacing between sutures in a conventional sutured anastomosis. A different spacing between the staples 22 may be used if desired. After completion of the anastomosis, the anvil arm 14 is withdrawn from the target vessel 30 between adjacent staples 22. The withdrawal of the anvil arm 14 leaves a gap that is approximately the same as the spacing between adjacent staples. Accordingly, substantially no blood leakage occurs at the location where the anvil arm has been withdrawn.

Figure 7:
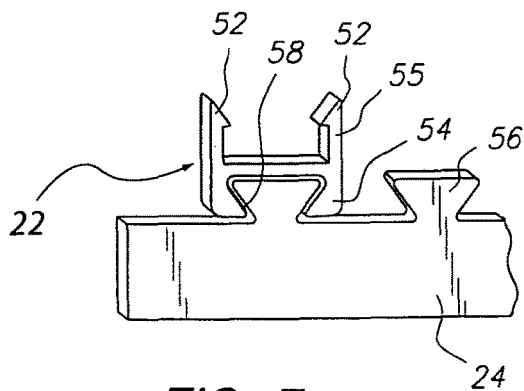
FIG. 7 is a perspective view of a staple supported on a staple holding strip.
Figure 8:
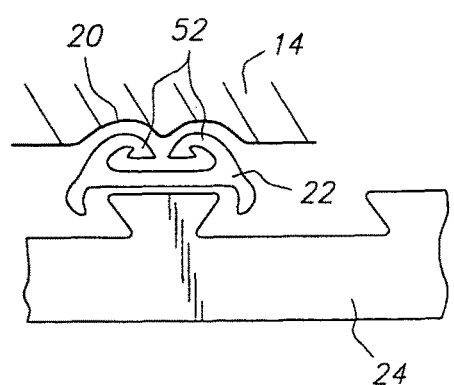
FIG. 8 is a side view of the staple and staple holding strip of FIG. 7 when the ends of the staple have been bent by contact with an anvil.

FIGS. 7 and 8 illustrate one example of a staple 22 connected to a staple holding strip 24. This staple 22 includes barbed staple ends 52 extending from the front portion of the staple 22 and a C-shaped portion 54 extending from a rear of the staple 22 for connecting the staple 22 to the staple holding strip 24. The staple holding strip 24 includes a plurality of protrusions 56 for receiving the staples 22. The C-shaped portion 54 of each staple 22 is received around one of the protrusions 56 and is secured in place at one or more locations, such as by welds 58 or by a frangible linkage or connection. Alternately, the C-shaped portion 54 of each staple 22 may be secured to the staple-holding strip 24 in a different way. As shown in FIG. 8, when the staple holding strip 24 is advanced toward the anvil arm 14, the barbed staple ends 52 are received in the recesses 20 in the anvil arm 14. Contact between each staple end 52 and the corresponding recess 20 generates a moment that causes the barbed staple ends 52 to bend towards one another. At the same time that the barbed staple ends 52 bend over, or after the bending of the staple ends 52, the staple 22 is detached from the staple holding strip 24. The staple 22 may be detached from the staple holding strip 24 by the action of bending the barbed staple ends 52 such that the C-shaped portion 54 of the staple 22 splays outward and breaks apart from the corresponding protrusion 56 on the staple holding strip 24, by bending a frangible connection between the staple holding strip and the staples to separate the staples, or any other known separation methods, such as melting of a connection between the staple and the staple holding strip.

Figure 9:
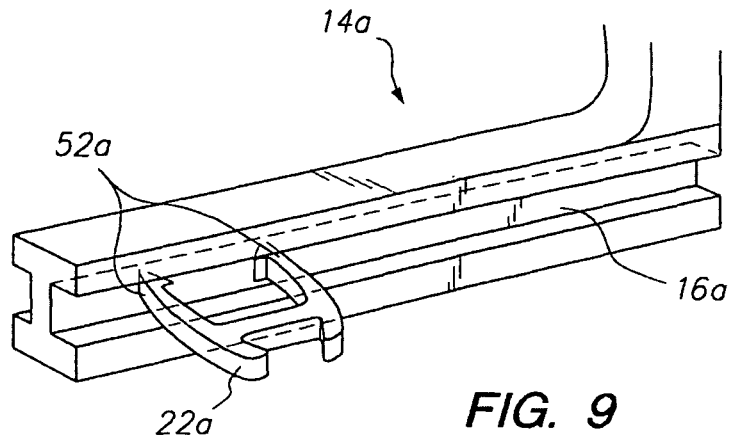
FIG. 9 is a perspective view of an anvil and staple according to another aspect of the present invention.

FIG. 9 illustrates an alternate staple 22a having inwardly curved barbed staple ends 52a. Because the staple ends 52a are themselves curved, the corresponding staple bending feature or features 16a need not be curved to bend the ends 52a of the staples 22a. As shown in FIG. 9, the staple bending features 16a on each side of the anvil arm 14a may be formed as a single longitudinal groove along the anvil arm 14a, where the staple bending feature 16a has a substantially flat surface. When the curved ends 52a of the staple 22a are received in the groove 16a of the anvil arm 14a, the ends bend inward to secure the tissue with the staple. Alternately, the staple may be configured differently. Alternately, two or more different kinds of staples are deployed by the staple holder 38 in order to form a single anastomosis.

Figure 10A:
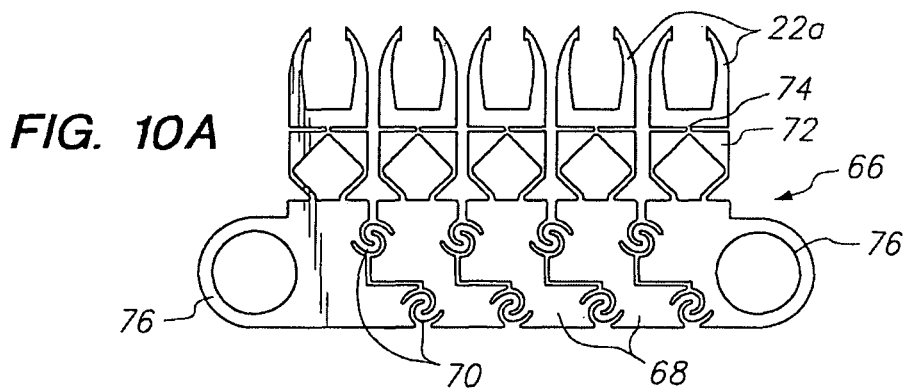
FIGS. 10A and 10B are is a side views of a plurality of staples supported on two examples of expandable staple holding strips.

Referring also to FIG. 10A, a plurality of staples 22a are positioned on an expandable staple holding strip called an expandable backbone 66. The expandable backbone 66 includes a plurality of elements 68 which are interconnected by one or more expanding members 70. Each of the backbone elements 68 is provided with a connecting diamond member 72 that is connected to one of the staples 22a. As shown in FIG. 10A, each staple 22a is connected to the corresponding diamond member 72 by a thin connecting section 74. The expandable backbone 66 allows the spacing between the staples 22a to be adjusted for the particular anastomosis to be performed. The backbone 66 allows expansion of the distance between staples from a distance of approximately 0.1 mm to a distance of approximately 1 to 4 mm, i.e., expansion of up to 40 times the original spacing. Alternately, the backbone 66 allows a different amount of expansion. The expanding backbone 66 also includes two openings 76 at opposite ends which may be engaged by holding pins (not shown) on an anastomosis system or staple holder. The opening 76 allow the backbone 66 to be easily expanded by relative motion of the holding pins. The connecting diamond members 72 are configured to collapse inwardly toward the backbone when the staples 22a engage the staple bending surface or surfaces 16a of the anvil. The collapsing of each diamond member 72 forces the corresponding staple 22a to separate from the diamond member 72 at a connecting section 74. The connecting section 74 is a frangible linkage connecting a staple 22a to a corresponding diamond member 72.

Figure 10B:
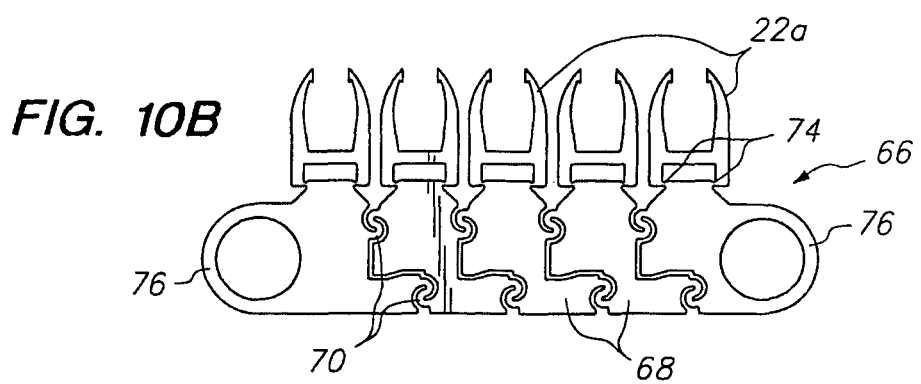

FIG. 10B illustrates another example of staples 22a detachably connected to a backbone 66. The staples 22a are each connected to the associated backbone elements 68 at two connecting sections 74. The staples 22a, backbone 66, and associated components are substantially as described above with regard to FIG. 10A.

Figure 11:
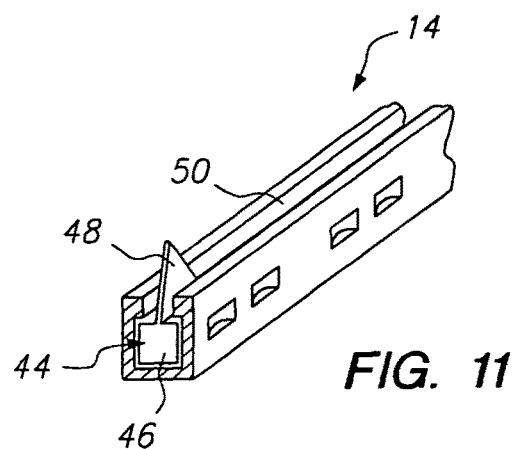
FIG. 11 is a perspective view of a portion of an anvil having a movable cutting device.

FIG. 11 shows a portion of an anvil arm 14 with a movable cutting device 44. The cutting device 44 includes a base 46 and a blade 48. The base 46 of the cutting device 44 is positioned in a longitudinal groove 50 in the anvil arm 14. After the anvil arm 14 has been inserted into the target vessel, the cutting device 44 may be moved longitudinally along the anvil arm 14 to form an incision in the target vessel.

Figure 12:
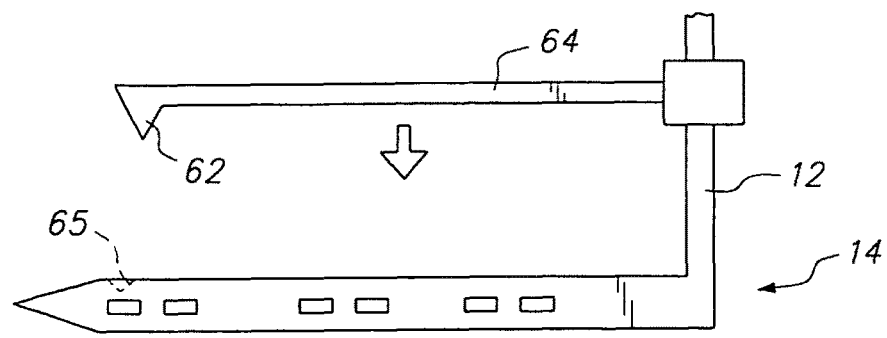
FIG. 12 is a side view of an anvil having an external cutting device.
Figure 12A:
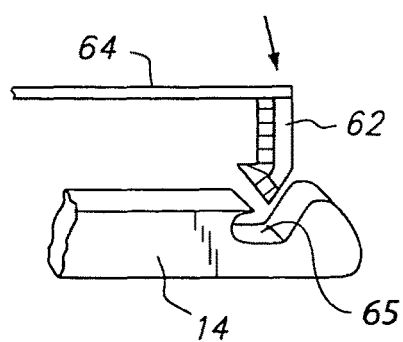
FIGS. 12A and 12B are side views of a portion of an anvil and two cutting devices that snap onto the anvil.
Figure 12B:
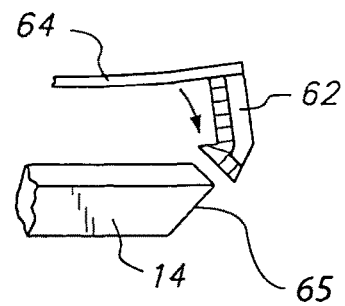

FIGS. 12, 12A, and 12B illustrate external cutting devices that are advanced down onto the anvil arm 14 after the anastomosis procedure and cut an incision in the target vessel from an exterior of the target vessel as the anvil arm 14 is withdrawn. As shown in FIG. 12, a knife 62 is positioned on a knife arm 64 that is movable along the handle 12 of the anvil. The knife 62 is moved downward in a direction substantially parallel to the longitudinal axis of the handle 12 until the knife 62 engages a recess 65 in the anvil arm 14. The knife 62 is thereby positioned substantially at the anastomosis site. The end of the graft vessel is then placed substantially against the wall of the target vessel at the anastomosis site, over the knife 62 and knife arm 64. As the anvil arm 14 is withdrawn from the anastomosis site, the knife 62 forms an incision in the target vessel. The knife 62 and knife arm 64 exit the anastomosis site via the joint between the graft vessel and the target vessel. The withdrawal of the anvil arm 14, knife 62 and knife arm 64 leaves a gap in the wall of the target vessel that is approximately the same as the spacing between adjacent staples to minimize or eliminate leakage through that gap. Alternately, the knife 62 may be moveable relative to the handle 12 in at least one direction in addition to a direction substantially parallel to the longitudinal axis of the handle 12. For example, the knife 62 may be moveable in a direction substantially parallel to the wall of the target vessel to create an arteriotomy in the target vessel at the junction between the graft vessel and the target vessel.

FIGS. 12A and 12B illustrate two alternate examples of the knife 62 which snap onto a corresponding engagement surface 65 of the anvil arm 14 so that the knife and anvil are secured together for formation of the incision during removal of the anvil arm 14 from the anastomosis site.

Figure 13:
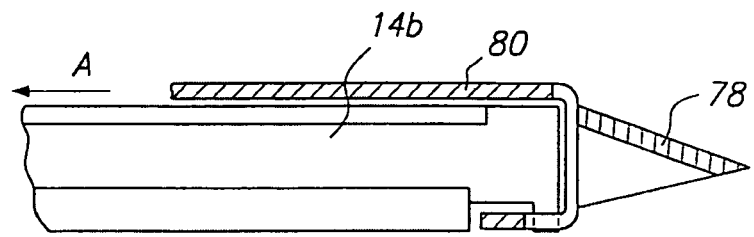
FIG. 13 is a side view of a portion of an anvil with an extendable cutting device.
Figure 14:
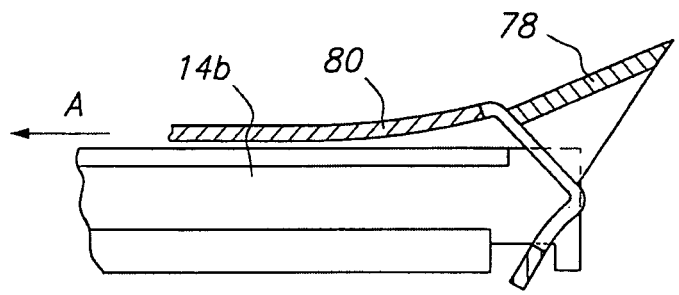
FIG. 14 is a side view of the anvil of FIG. 13 with the cutting device extended.

FIGS. 13-16 illustrate two variations of extendable cutting devices for making an incision in the target vessel while withdrawing the anvil arm 14 from the target vessel. FIG. 13 illustrates an anvil arm 14b having a blade 78 connected to a flexible blade support 80. When the blade support 80 is pulled in the direction of the arrow A with respect to the anvil arm 14b, the blade 78 moves from a forwardly extending position shown in FIG. 13 to an upwardly extending position shown in FIG. 14 as a result of flexure of the blade support 80. The blade 78 in the forwardly extending position may be used to form a small opening in the wall of the target vessel through which the anvil arm 14 is inserted into the target vessel. After an anastomosis has been performed, or while an anastomosis is performed, the blade 78 is moved to an upwardly angled or a vertical position in which the blade 78 is used to form an incision in the target vessel as the anvil arm 14b is removed from the target vessel.

Figure 15:
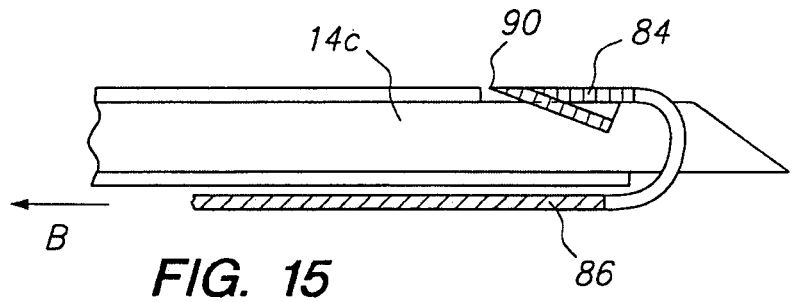
FIG. 15 is a side view of a portion of an anvil with an alternate extendable cutting device.
Figure 16:
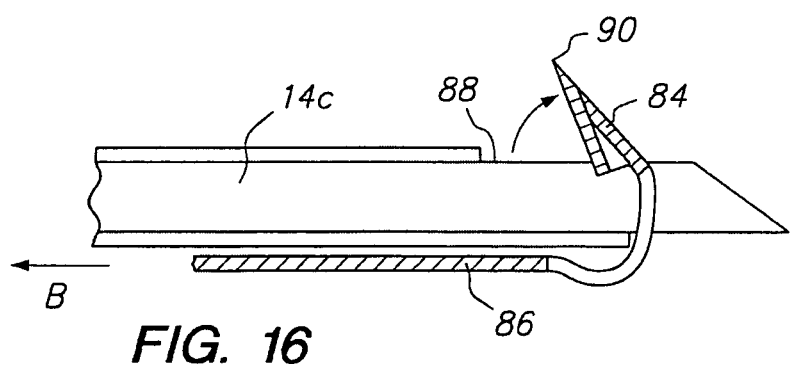
FIG. 16 is a side view of the anvil of FIG. 15 with the cutting device extended.

FIGS. 15-16 illustrate an alternate example of an anvil arm 14c having a blade 84 and a blade support 86. While the anvil arm 14c is inserted into the target vessel and during the anastomosis procedure, the blade 84 is positioned in a recess 88 in the anvil arm. The blade 84 may be moved from the position of FIG. 15 to the extended position of FIG. 16 by moving the blade support 86 in the direction of the arrow B with respect to the anvil arm. The blade 84 is flexible and stressed, such that freeing the blade 84 from the recess 88 causes the blade 84 to move to the extended position. Alternatively, the blade 84 may be extended automatically upon withdrawal of the anvil arm 14 when a blade tip 90 catches on an interior surface of the target vessel wall during withdrawal of the anvil arm.

The extendable cutting devices shown in FIGS. 13-16 are merely shown as examples of the type of cutting devices which may be used for making the incision. Once these cutting devices or blades have been extended from the anvil arm, they may be fixed to perform cutting as the anvil arm is removed from the target vessel or the blades may be movable along the anvil arm to make an incision prior to removal of the anvil arm from the target vessel.

Figure 55:
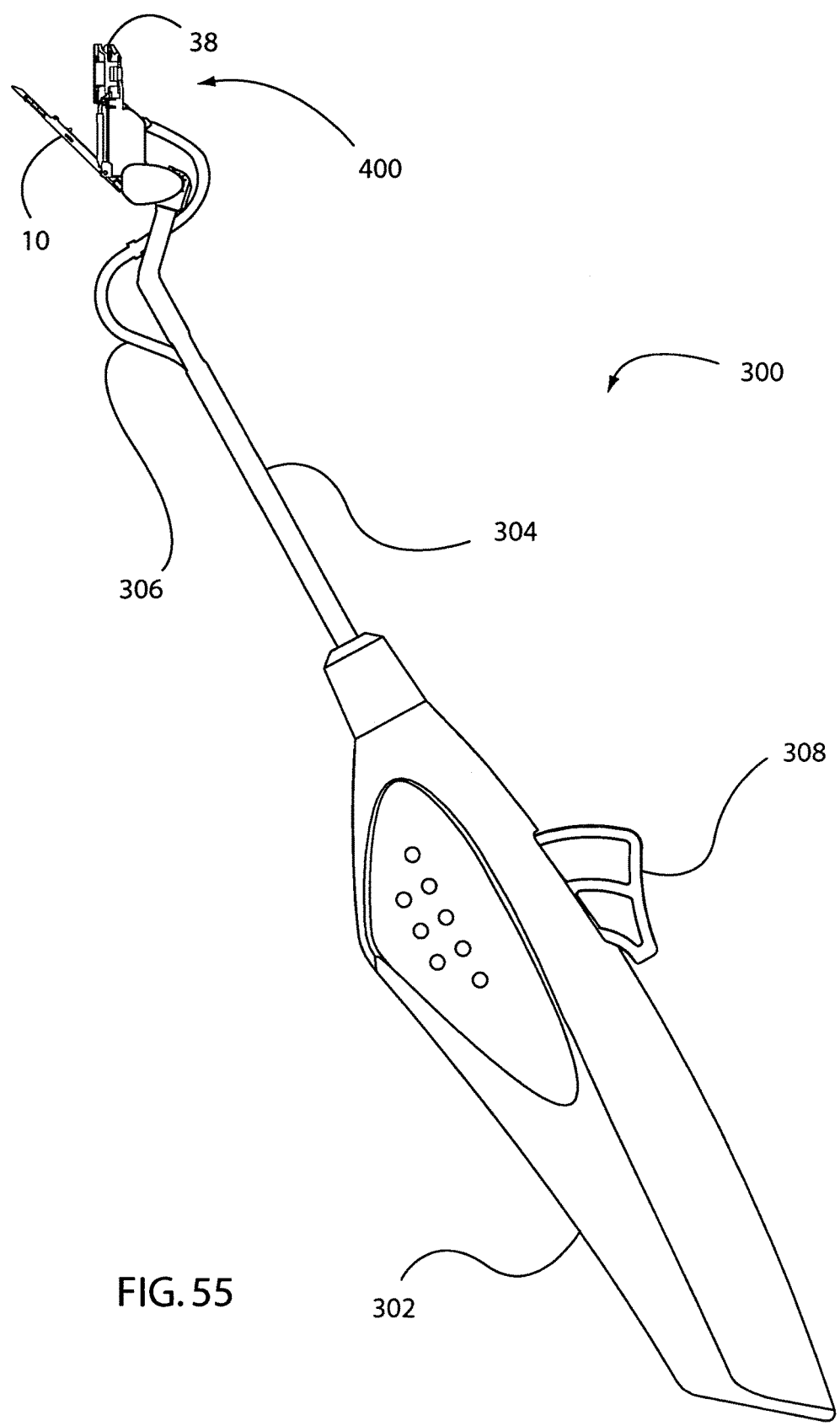
FIG. 55 is a side view of an anastomosis tool having a tissue effector and a handle.

Referring to FIG. 55, an exemplary anastomosis tool 300 is shown. The anastomosis tool 300 includes a handle 302, a shaft 304 connected to the handle 302, a cable housing 306 connected at one end to the handle 302, and a tissue effector 400 connected to both the shaft 304 and the cable housing 306. The anastomosis tool 300 may be configured differently, if desired. For example, the cable housing 306 may be omitted, and the cable or cables (not shown) that would otherwise extend therethrough are instead routed through the shaft 304. The handle 302 and/or the tissue effector 400 may be detachable from the shaft 304 to allow for interchangeability of these components. In this way, the same handle 302 may be used to perform more than one anastomosis within a single patient, where a different tissue effector 400 may be connected to that handle 302 for each anastomosis. Further, the handle 302 may be constructed from materials that can be sterilized, such as by an autoclave, and reused. The handle 302 may assume any appropriate configuration; the shape and configuration of the handle 302 described herein is exemplary and not limiting. The shaft 304 may be a rigid hollow structure such as a tube of stainless steel, but may be shaped differently and/or fabricated from a different material. Further, the shaft 304 may be flexible at least in part, rather than rigid. Alternatively, the shaft 304 may be omitted altogether, such that the handle 302 is connected to the tissue effector 400 by one or more cables that would otherwise have extended through the shaft 304. The handle 302 includes a trigger 308 that provides for actuation of the anastomosis tool 300 based solely on a single input to that trigger 308, as described in greater detail below. Alternately, additional inputs may be utilized to actuate the anastomosis tool 300. For example, actuation of the anastomosis tool 300 may be based on an input to one or more buttons in addition to the trigger 308.

The tissue effector 400 includes an anvil 10 and a staple holder 38. The tissue effector 400 may be permanently fixed to the shaft 304, or may be detachable from it such that is it decoupled from the handle 302. That is, tissue effectors 400 may be interchangeable. Alternately, the shaft 304 is not provided, and the tissue effector 400 is directly coupled to the handle 302. One end of the cable housing 306 is fixed to the staple holder 38.

Figure 34:
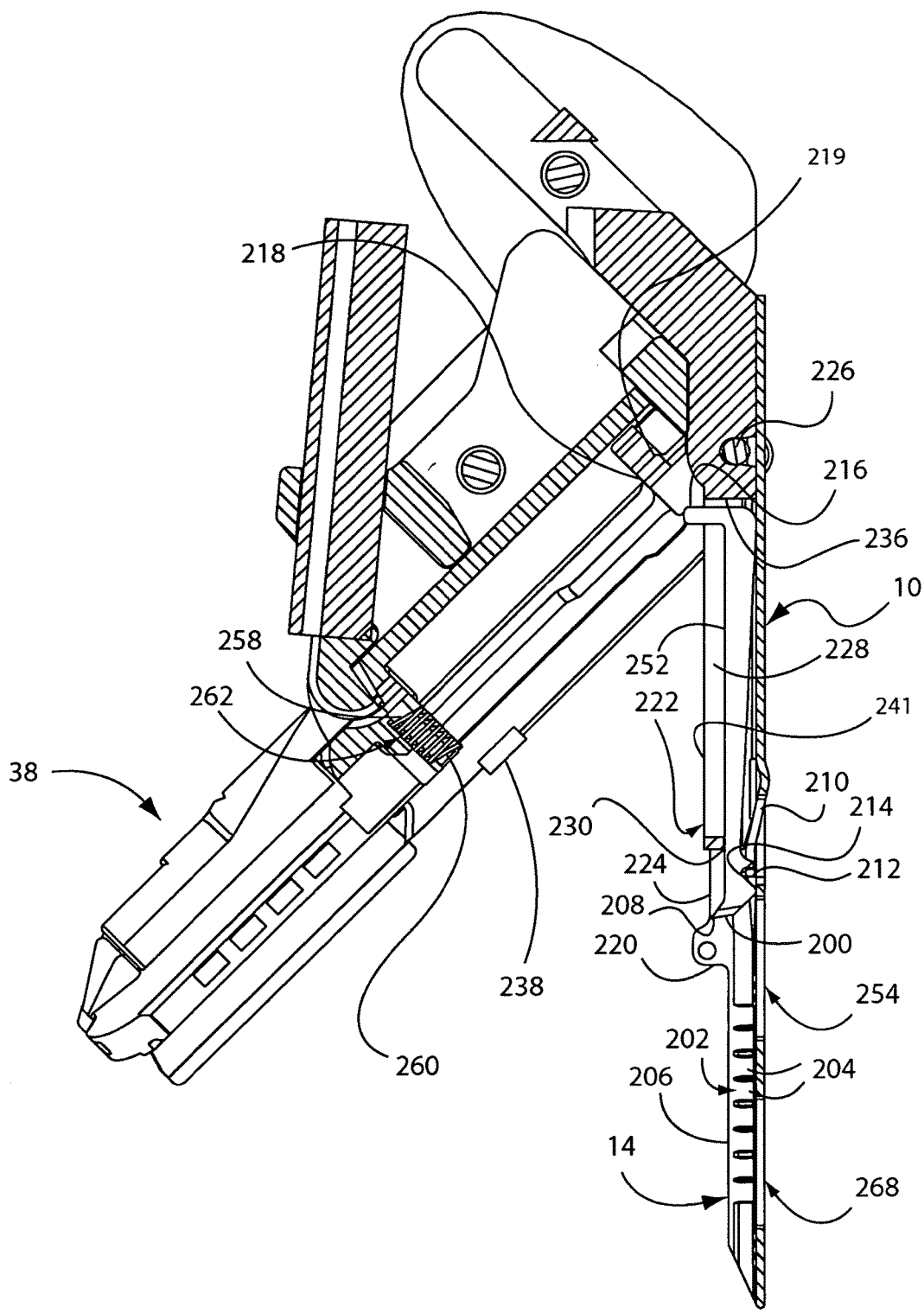
FIG. 34 is a side cutaway view of a first embodiment of an anvil, a cutter and a staple holder, where the anvil and staple holder are spaced apart from each other.
Figure 35:
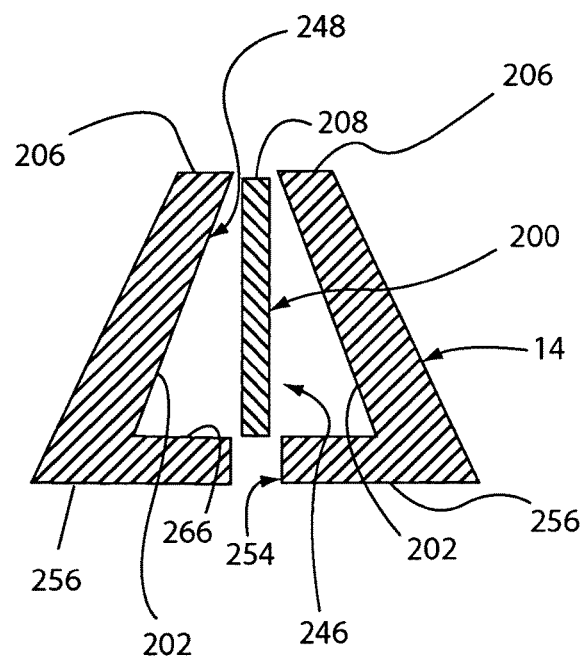
FIG. 35 is an end cross-section view of the anvil of FIG. 34.

The anvil 10 of the tissue effector 400 may be as described above, or may be configured differently. Advantageously, the anvil 10 also includes a cutter 200 that is moveable relative to the anvil 10 for making an incision in the wall of a target vessel. Referring to FIGS. 34 and 35, a tissue stop 220 is formed into or connected to the anvil 10. The portion of the anvil 10 distal to the tissue stop 220 is configured to penetrate into the wall of a target vessel, and may be referred to as the anvil arm 14. A channel 246 is defined within the anvil arm 14, through which a cutter 200 is configured to move. The cutter 200 is narrower than the channel 246, such that interior surfaces 202 on either side of the channel 246 may guide the translation of the cutter 200 relative to the anvil arm 14. As used in this document, the term "translation" as used in regard to the cutter 200 refers to motion of the cutter 200 in the distal or proximal direction, whether or not the cutter 200 or a portion thereof moves upward or downward during that motion. For convenience, the direction substantially perpendicular to the longitudinal centerline of the anvil arm 14 toward the wall of the target vessel may be referred to as "upward", and the direction substantially perpendicular to the longitudinal centerline of the anvil arm 14 away from the wall of the target vessel may be referred to as "downward". However, the positioning of the anvil arm 14 in use is not limited to an orientation in which these directions correspond to absolute directions measured relative to the ground. Similarly, for convenience, motion upward or downward may be referred to as "vertical" motion, and motion substantially parallel to the longitudinal centerline of the anvil arm 14 may be referred to as "horizontal" motion.

Figure 36:
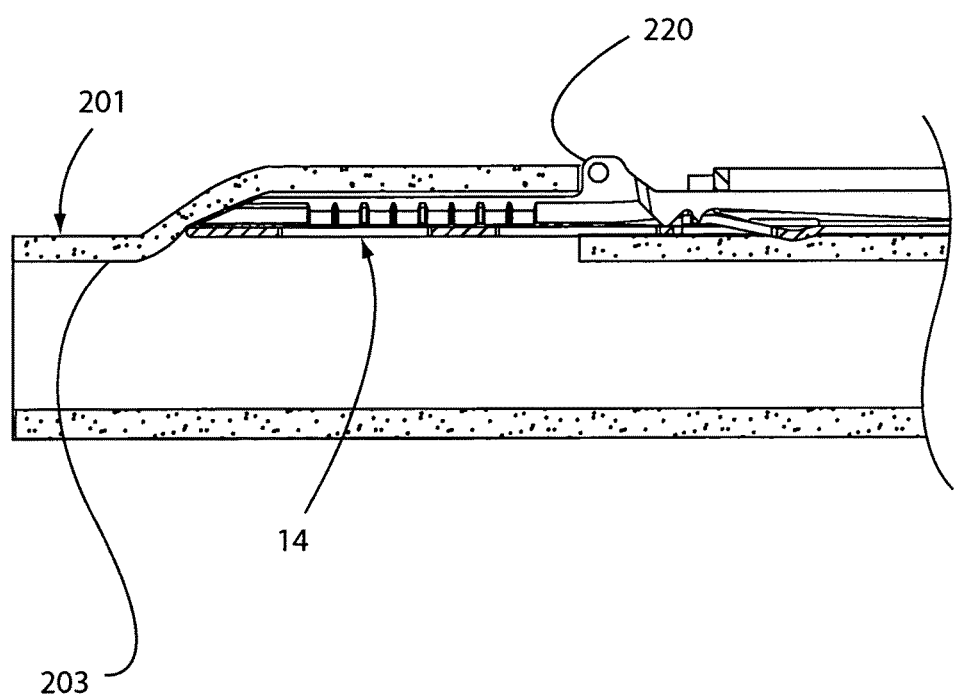
FIG. 36 is a side cutaway view of a portion of the anvil inserted into the lumen of a target vessel.

The anvil arm 14 includes a contact surface 206. Referring also to FIG. 36, in use, the contact surface 206 of the anvil arm 14 is placed substantially against the inner surface 203 of a target vessel 201. The contact surface 206 substantially defines a place that is substantially parallel to the longitudinal centerline of the anvil arm 14. Alternately, the contact surface 206 is contoured and/or oriented differently. An upper opening 248 extends along at least a portion of the contact surface 206 in a direction substantially parallel to the longitudinal centerline of the anvil arm 14, and opens into the channel 246. The upper opening 248 may divide the contact surface 206 into symmetrical or asymmetrical sections. Further, the contact surface 206 may be formed by two substantially planar surfaces, by one substantially planar surface and a differently-shaped surface, or by another set of surfaces. Additionally, the contact surface 206 may be formed by two thin edges, each edge occurring at the intersection of a wall of the upper opening 248 and an outer surface of the anvil arm 14. The upper opening 248 need not extend proximally any further than the tissue stop 220. However, the upper opening 248 may extend proximal to the tissue stop 220, if desired. A first lower opening 254 and a second lower opening 268 are defined through a lower surface 256 of the anvil arm 14. The lower surface 256 of the anvil arm 14 may be substantially parallel to the contact surface 206 or may be oriented differently relative to the contact surface 206. Alternately, the first lower opening 254 and/or the second lower opening 268 do not extend completely through the anvil arm 14, and instead are depressions extending along at least part of a bottom surface 266 of the channel 246.

Figure 37:
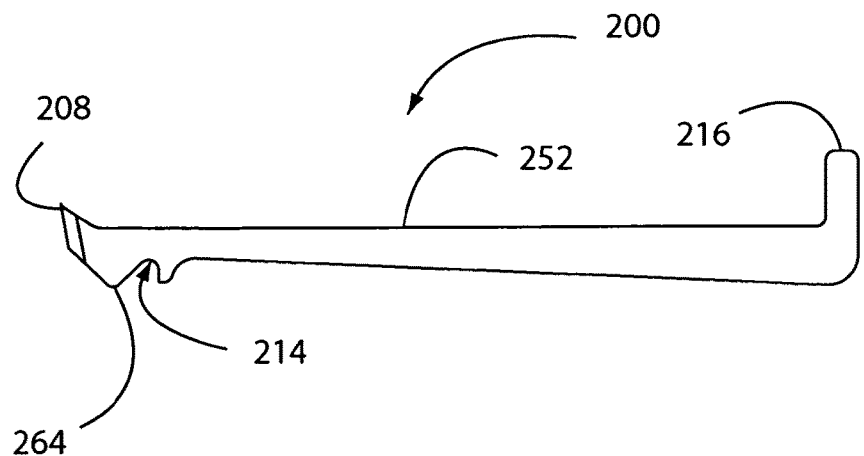
FIG. 37 is a side view of the cutter.
Figure 38:
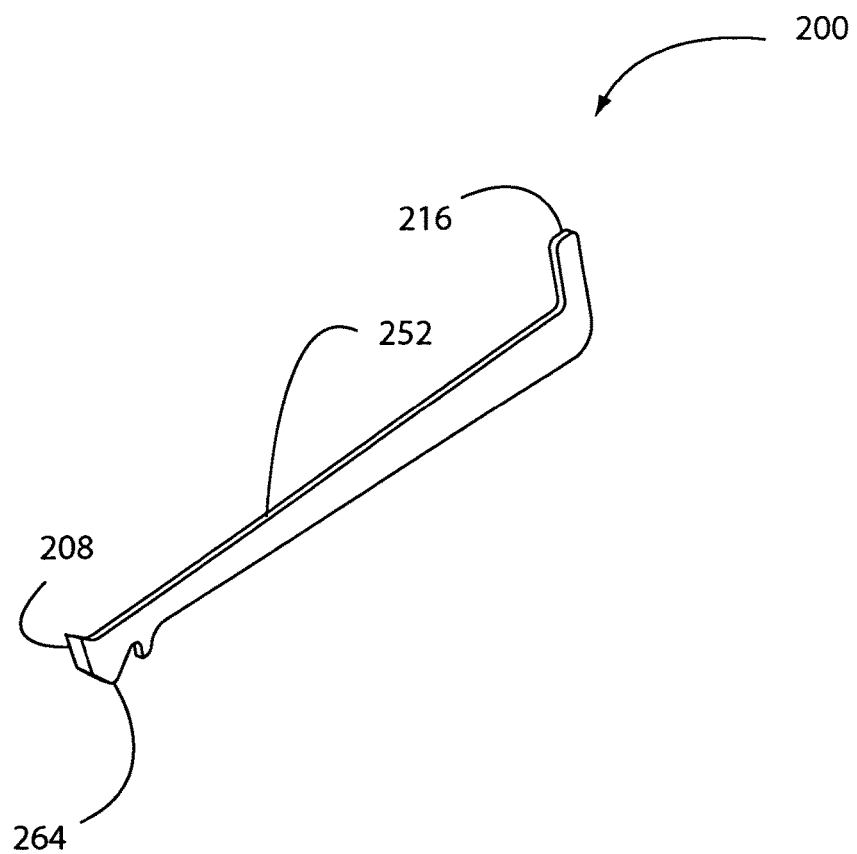
FIG. 38 is a perspective view of the cutter of FIG. 37.

Referring also to FIGS. 37-38, the cutter 200 is a thin, rigid member, shaped such that it can be held within the channel 246 in the anvil arm 14. The cutter 200 has a substantially constant width along its entire length. Alternately, the width of the cutter 20 may vary along its length. The cutter 200 may be made of metal, ceramic, plastic, or other material, or from a combination of different materials. A sharp projection 208 extends upward from the cutter 200 at or near its distal end. The projection 208 is substantially triangular, but may be shaped differently. The projection 208 may be smooth or serrated, or otherwise shaped or formed. A portion of the projection 208 may be ground or otherwise honed to a sharp edge to facilitate the motion of the projection 208 through the tissue of the wall of a target vessel, as described in greater detail below. If so, the cutter 200 is composed of a material that can be sharpened adequately to cut tissue. Alternately, the cutter 200 may be flexible, at least in part. Further, the projection 208 may be located at a different position on the cutter 200 than at or near its distal end. An additional sharp point (not shown) may be provided at the distal end of the cutter 200, extending in a distal direction, in order to create an initial puncture or incision in the wall of the target vessel. Such a point may be as described in U.S. patent application Ser. No. 10/134,081, which is herein incorporated by reference in its entirety.

Figure 39:
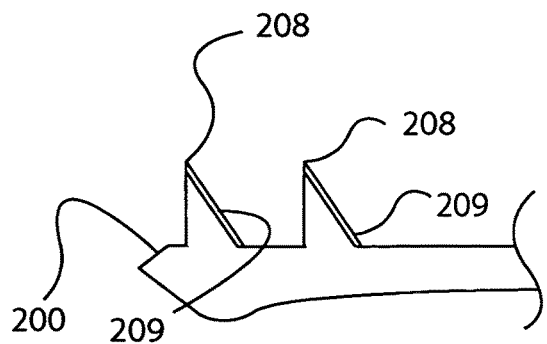
FIG. 39 is a side view of the distal end of a second embodiment of a cutter.
Figure 40:
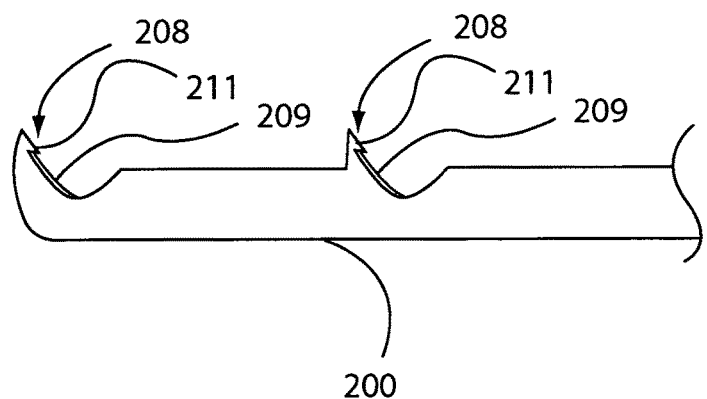
FIG. 40 is a side view of the distal end of a third embodiment of a cutter.
Figure 41:
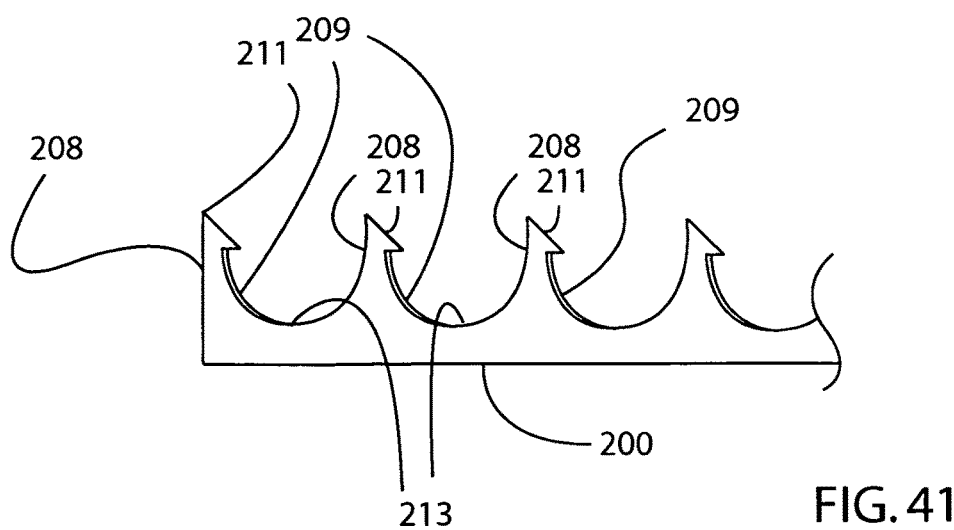
FIG. 41 is a side view of the distal end of a fourth embodiment of a cutter.
Figure 42:
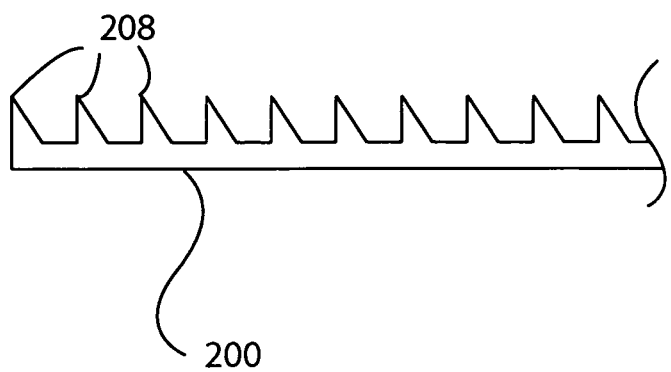
FIG. 42 is a side view of a portion of a fifth embodiment of a cutter.

One or more additional projections 208 may be provided, if desired. For example, two or more projections 208 may extend upward from the cutter 200. Where multiple projections 208 are used, they may cooperate with one another to create an incision in the wall of the target vessel. Referring also to FIG. 39, a second projection 208 extends upward from the cutter 200 proximal to a first projection 208. The projections 208 are both substantially the same triangular shape and the same size. However, the projections 208 may be shaped and sized differently. The projections 208 are both substantially planar, and are aligned such that both projections 208 lie in substantially the same plane. Each projection 208 may include at least one sharpened or beveled edge 209 oriented to engage and incise the wall of the target vessel when the cutter 200 is translated, as described below. Referring to FIG. 40, at least two projections 208 extend upward from the cutter 200. The projections 208 each have a barb 211 at the tip. However, the barb 211 may be omitted from some or all of the projections 208. Under the barb 211, a sharpened or beveled edge 209 extends downward and proximally. The edge 209 may be straight or curved. The upper end of the edge 209 is distal to the lower, proximal end of the corresponding barb. The edge 209 of each projection 208 is oriented to engage and incise the wall of the target vessel when the cutter 200 is translated. Referring to FIG. 41, at least two projections 208 extend upward from the cutter 200, at least one of which has a barb 211 at its tip. The edge 209 associated with each projection 208 is more curved than the edge 209 shown in FIG. 40. Alternately, the edge 209 is substantially straight, or gently curved, or positioned on a portion of a larger curved segment 213 extending downward from and proximal to the barb 211. Referring to FIG. 42, a number of projections 208 may be placed along a length of the cutter 200. This length may be comparable to the desired length of the incision in the wall of the target vessel. These projections 208 may be substantially triangular as shown, or may be shaped differently. Where more than one projection 208 is used on the cutter 200, the projections 208 need not have the same configuration. For example, projections 208 such as the exemplary projections 208 shown in FIGS. 39-41 may be mixed together on the same cutter 200. Alternately, one or more of the projections 208 are moveable relative to the cutter 200, such that one or more projections 208 can be moved upward or downward relative to the cutter 200.

Figure 43:
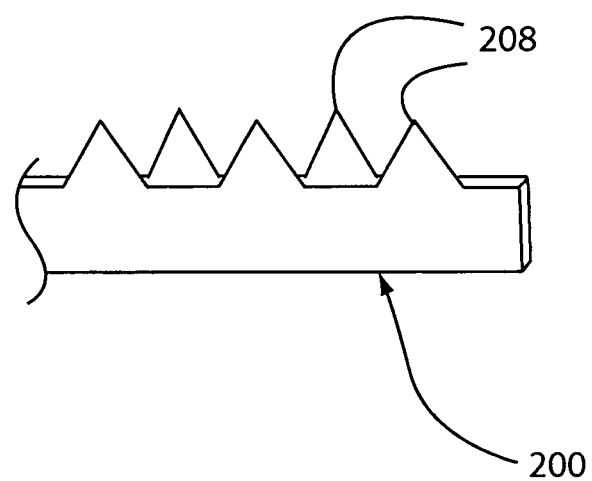
FIG. 43 is a side view of the distal end of a sixth embodiment of a cutter.

As another example of a configuration of the projections 208, referring to FIG. 43, the projections 208 extending upward from the cutter 200 each are substantially planar, and are aligned such that not all of the projections 208 lie in the same plane. In such a configuration, the projections 208 may create a wider incision in the wall of the target vessel than would be created if the projections 208 were substantially aligned. For example, one set of projections 208 may be aligned substantially in a first plane, and a second set of projections 208 may be aligned substantially in a second plane substantially parallel to the first plane. The second plane and the first plane may be oriented differently relative to one another, if desired. As another example, none of the projections 208 lie in a common plane with one or more other projections 208. Referring to FIGS. 39-42, by using multiple projections, the cutter 200 need not be translated as far to make an incision in the wall of the target vessel as it would if only a single projection 208 were used, as described in greater detail below.

Referring back to FIGS. 34-35, an interior surface 202 is located on each side of the channel 246. Each interior surface 202 may be substantially planar, curved, or may be shaped differently. Further, each interior surface 202 may be oriented at an angle to vertical or substantially vertical. The interior surfaces 202 may be formed such that the channel 246 is substantially bilaterally symmetrical, or may be formed to result in a channel 246 that is not bilaterally symmetrical. The interior surfaces 202 of the channel 246 within the anvil arm 14 may include raised features 204 that correspond to depressed staple bending features (not shown) on the outer surface of the anvil arm 14. That is, if the staple bending features are stamped into the anvil arm 14, or formed in another way that causes deformation of the anvil arm 14, the depressed staple bending features result in corresponding raised features 204 on the interior surface 202 of the channel 246. The raised features 204 do not interfere with the motion of the cutter 200 through the channel 246. Alternately, the raised features 204 are not present on the interior surface 202 of the channel 246.

Optionally, a safety feature 210 may be connected to the underside of the anvil 10. The safety feature 210 is biased toward the anvil 10 and the cutter 200. The safety feature 210 may be biased into the channel 246 within the anvil 10. Alternately, the safety feature 210 is connected to a different location, such as the underside of the anvil arm 14. The safety feature 210 may be flexible or rigid. The safety feature 210 includes a tip 212 that is oriented substantially transverse to the longitudinal centerline of the cutter 200. Alternately, the tip 212 may be oriented in a different direction. If the safety feature 210 is provided, the cutter 200 may include a safety recess 214 defined in it, corresponding to the tip 212 of the safety feature 210. The tip 212 is shaped and sized such that it can engage the safety recess 214. The tip 212 may be a bar or rod oriented substantially transverse to the direction of translation of the cutter 200, or may be shaped or oriented differently.

In FIG. 34, the staple holder 38 has not yet been moved into position to perform anastomosis. In this position, if the safety feature 210 is provided, the tip 212 of the safety feature 210 is biased upward to engage the safety recess 214. The engagement between the safety recess 214 and the tip 212 of the safety feature 210 substantially prevents translation of the cutter 200 within the channel 246. Thus, the cutter 200 and the projection 208 are prevented from deploying until the staple holder 38 has been moved into the appropriate position relative to the anvil arm 14, and inadvertent deployment of the cutter 200 is prevented.

Figure 58:
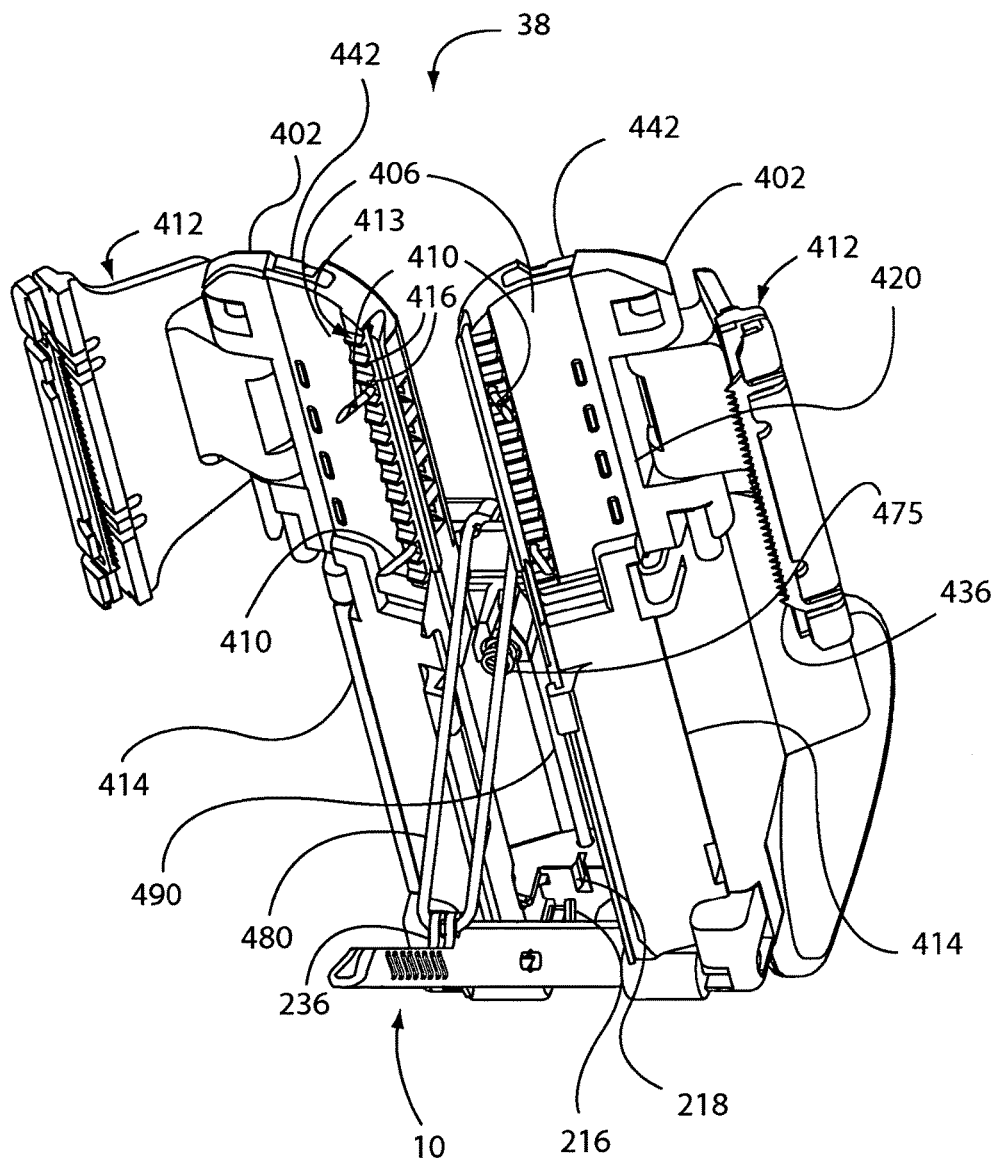
FIG. 58 is another perspective view of the tissue effector of FIG. 55 in the first position.
Figure 68:
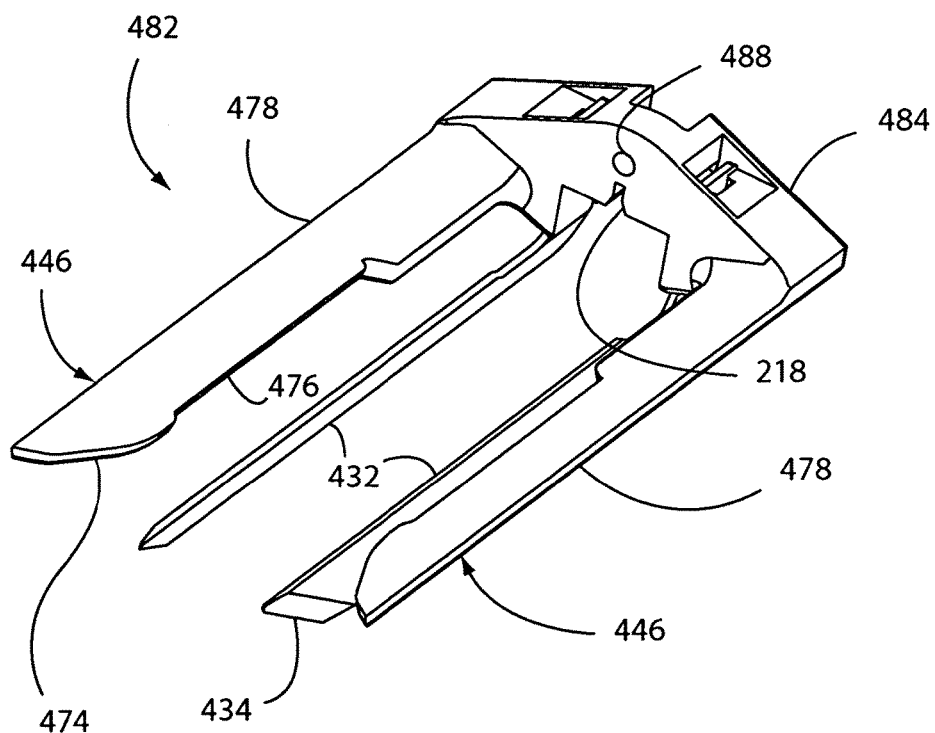
FIG. 68 is a perspective view of a sled used in the tissue effector of FIG. 55.
Figure 69:
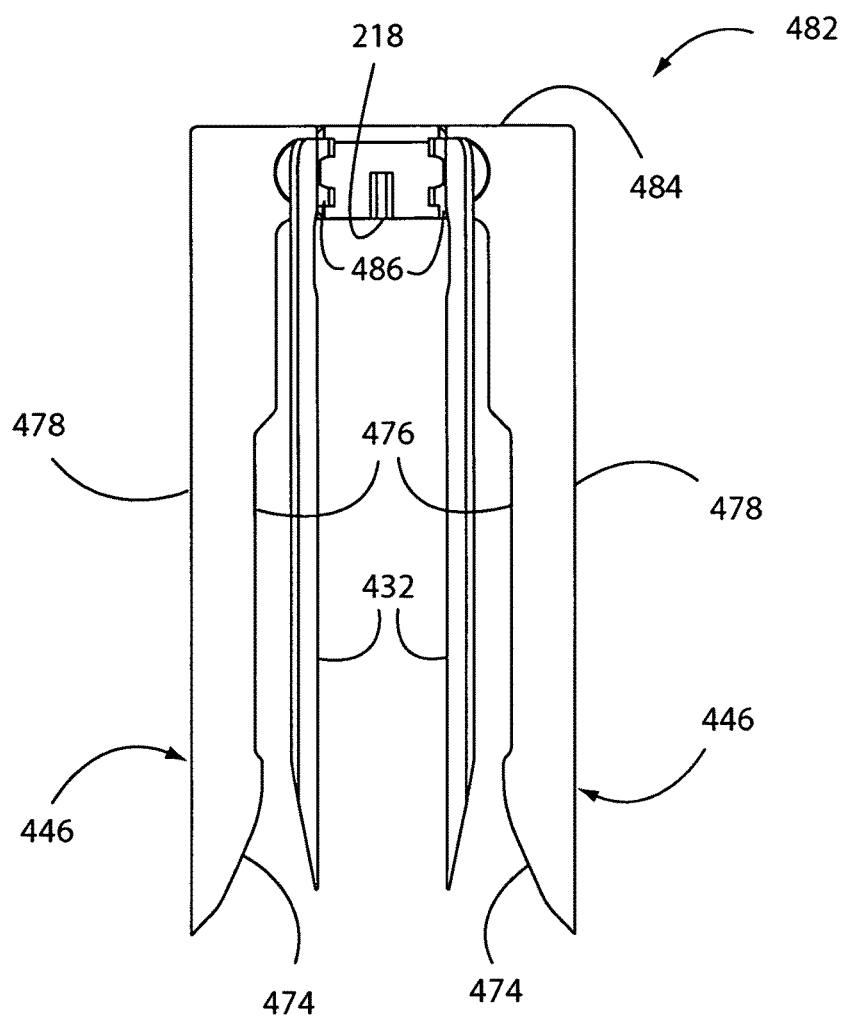
FIG. 69 is a bottom view of the sled of FIG. 68.

The cutter 200 includes an engagement member 216 extending upward from a location at or near its proximal end. The engagement member 216 instead may extend downward from the cutter 200 or to the side of the cutter 200. Further, the engagement member 216 may be positioned at a location other than at or near the proximal end of the cutter 200. The engagement member 216 is configured to engage at least a portion of a corresponding receiver 218 in the staple holder 38. Thus, after engagement between the engagement member 216 and the receiver 218, translation of the receiver 218 results in translation of the cutter 200. The receiver 218 is a structure that is at least partially open on its underside and that includes at least one surface 219 configured to engage the engagement member 216. As shown in FIG. 34, the surface 219 is a partially-curved surface shaped to receive the curved upper end of the engagement member 216. However, the receiver 218 may be a flat vertical surface, a curved surface, a structure such as an inverted cup that is open on its underside and that has a wall or walls encircling the engagement member 216, or any other structure or mechanism capable of engaging the engagement member 216 and urging it distally. Referring also to FIGS. 58 and 68-69, the receiver 218 may be defined in a sled 482, which is described in greater detail below.

An anvil insert 222 is fixed to the anvil 10. As one example, the anvil 10 is wider proximal to the anvil arm 14, open at its top with a space therein. The anvil insert 222 can be inserted into the anvil 10 through its top, such that the anvil insert 222 is partially or completely positioned within the anvil 10. However, the anvil insert 222 may be connected to the anvil 10 in another way. Alternately, the anvil insert 222 is connected to and capable of motion relative to the anvil 10. Further, the anvil insert 222 instead may be connected to the proximal end of the anvil arm 14, or another location on the anvil arm 14. A cavity 228 is defined within the anvil insert 222. An aperture 230 is defined through the distal end of the anvil insert 222 into the cavity 228, connecting the channel 246 in the anvil arm 14 and anvil 10 to the cavity 228. The cutter 200 extends through the aperture 230, such that the distal end of the cutter 200 is positioned within the channel 246 and the proximal end of the cutter 200 is positioned within the cavity 228.

A cutter stop 236 may be formed into or connected to the anvil insert 222, or formed into or connected to the anvil 10 itself or another structure or mechanism. The cutter stop 236 may engage the proximal end of the cutter 200 if the cutter 200 is moved to a defined position within the cavity 228, thereby restricting its proximal translation. A cavity 262 may be defined within the staple holder 38 or a separate component connected to the staple holder 38. A post 258 is positioned at the upper end of the cavity 262, where the post 258 is oriented downward. A biasing element 260 is connected at one end to the post 258. The biasing element 260 may be a coil spring, a leaf spring, a different type of spring, an elastomer, a wire form, or other structure or mechanism capable of exerting a biasing force. The biasing element 260 is positioned within and protected by the cavity 262, where the cavity 262 is used. The cavity 262 may be a cylindrical opening having a diameter substantially the same as the outer diameter of the biasing element 260, such that the cavity 262 restricts the biasing element 260 to motion substantially along the axis of the cavity 262 and thus directs the force exerted by the biasing element 260 in a substantially downward direction, preventing bending or other undesirable motion of the biasing element 260. The end of the biasing element 260 that is not connected to the post 258 contacts the cutter 200. As an example, the biasing element 260 may be a compression spring that is compressed between the post 258 and the cutter 200, resulting in a force on the cutter 200 that biases the cutter 200 downward. The cutter 200 is slidable relative to the biasing element 260, such that the biasing element 260 exerts a downward force on the cutter 200 at different locations along its upper surface 252 as the cutter 200 translates. Thus, at least the distal end of the cutter 200 is biased downward throughout its translation along the anvil 10. The entire cutter 200 may be biased downward, if desired. Alternately, the post 258 is omitted, and the biasing element 260 is fixed to an upper surface of the cavity 260. Alternately, the biasing element 260 is omitted, and the cutter 200 is biased downward in another way. For example, the cutter 200 may be constructed from an elastic or superelastic material that is formed in such a way as to produce a downward bias.

Figure 56:
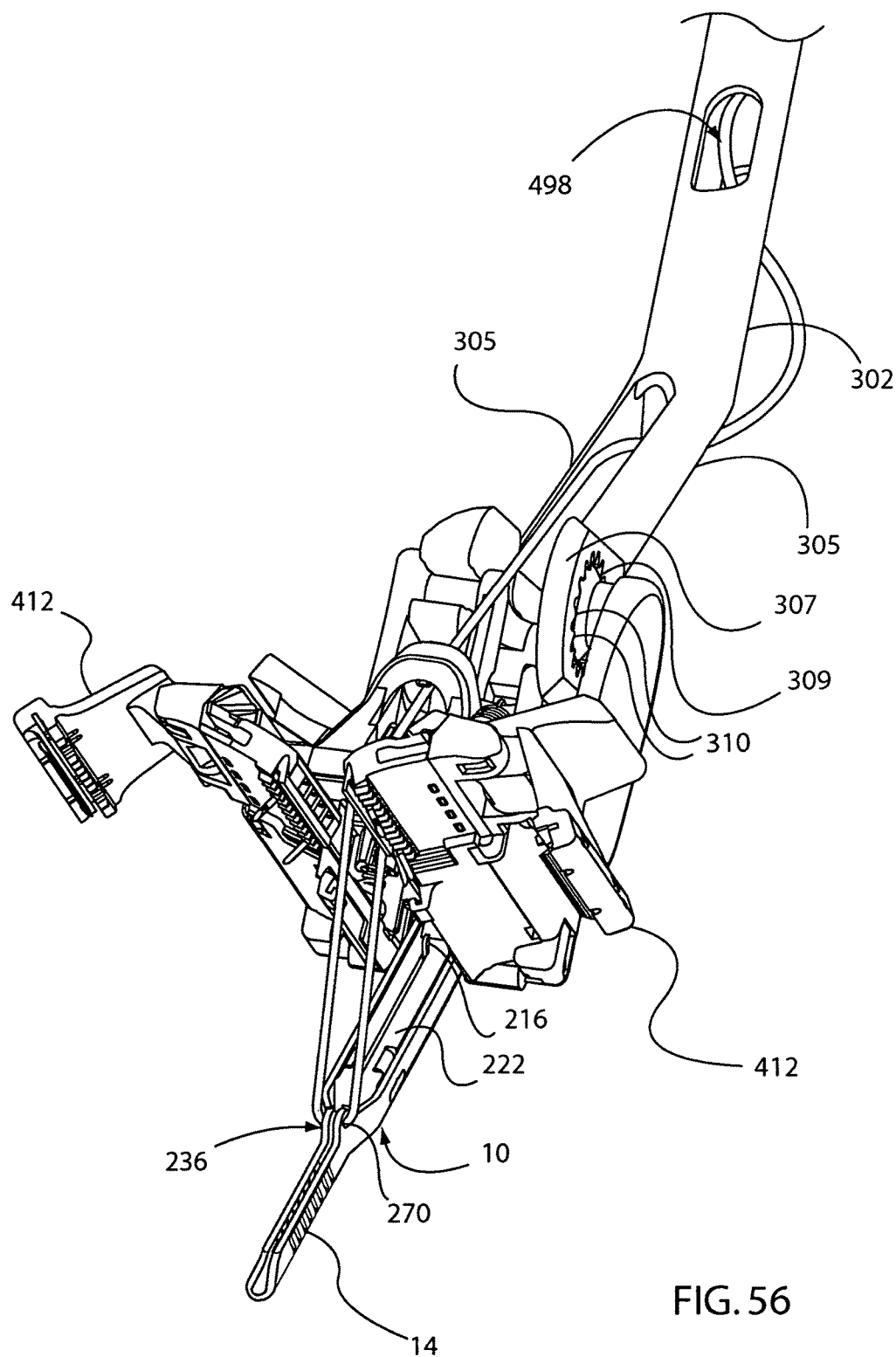
FIG. 56 is a perspective view of the tissue effector of FIG. 55 in first position.

Referring also to FIG. 56, the anvil 10 may include one or more attachment features 270. The attachment features 270 provide a location for attachment of one or more cables or other force transmission structures or mechanisms. As one example, the attachment features 270 may be one or more passages 270 through the cutter stop 236. The cutter stop 236 may include two or more spaced-apart members. If so, the attachment features 270 may be substantially aligned with one another, or offset from one another. However, the cutter stop 236 may be a single member, if desired. As another example, one or more of the attachment features 270 are separate from the cutter stop 236, and are positioned at a different location on the anvil 10. As another example, one or more of the attachment features 270 may extend in a direction from the anvil 10 that is other than upward.

The configuration of the attachment features 270 is related to the configuration of the cable or other force transmission structure or mechanism attached to it, such that the connection between them is secure. As one example, the cutter stop 236 includes two spaced-apart members, and the attachment features 270 are passages through the upper portion of each member of the cutter stop 236. Two separate cables are connected to the attachment features 270. The end of each cable is passed through one of the attachment features 270, after which it is welded, connected with adhesive, clamped, tied or otherwise secured to the cutter stop 236. Alternately, a single first cable is passed through each of the attachment features 270, such that the free ends of the first cable are spaced apart from the attachment features 270. In this way, no additional steps are needed to secure the first cable to the attachment features 270. However, the cable may be welded, connected with adhesive, clamped, tied or otherwise secured to the cutter stop 236, if desired.

Figure 44:
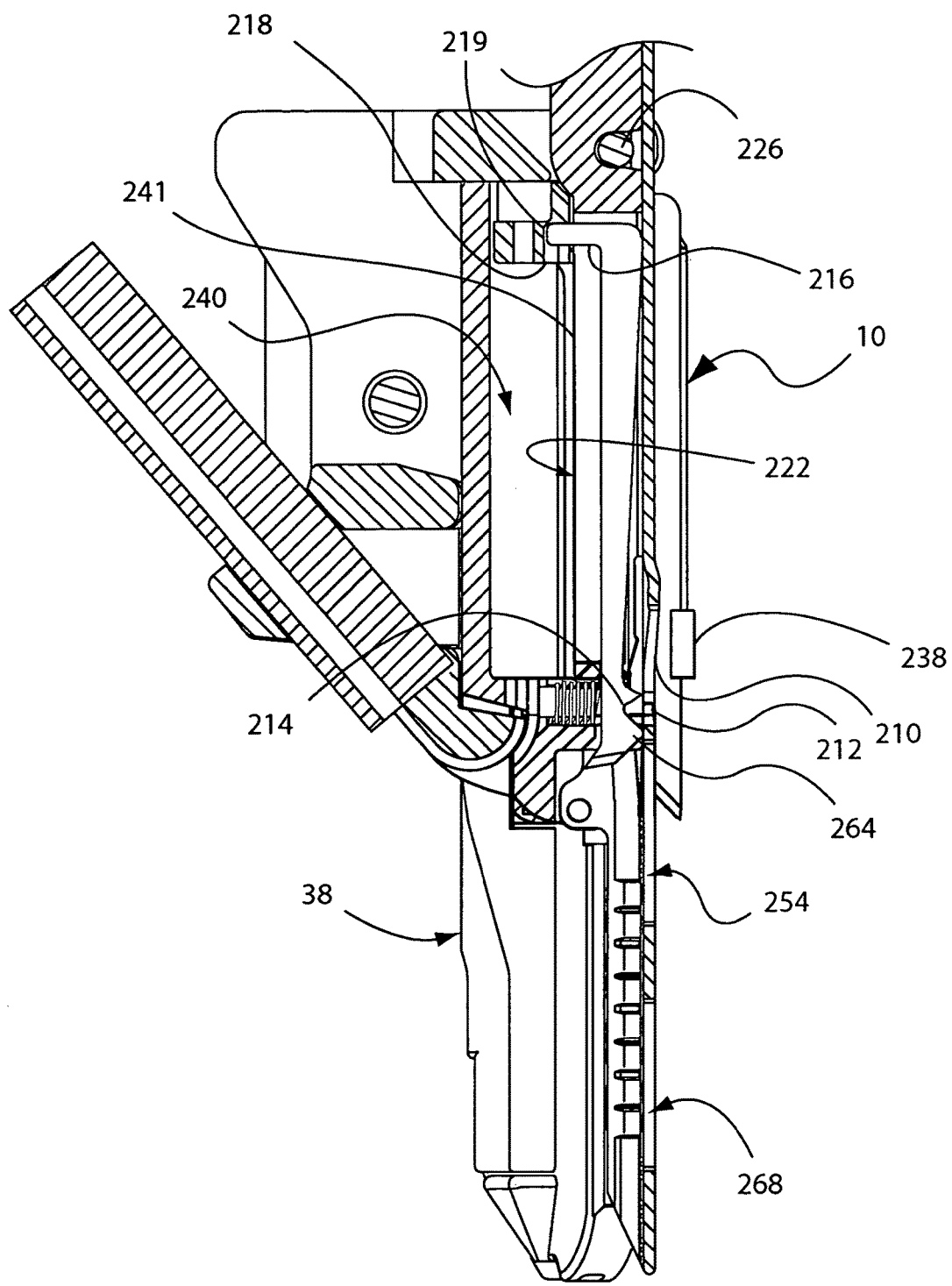
FIG. 44 is a side cutaway view of the anvil and staple holder of FIG. 34, where the cutter is in a first position.

Referring also to FIG. 44, the anvil 10 extends proximally to a pivot point such as a pin 226. The pivot point may be any other structure or mechanism that allows the anvil 10 to rotate about it. Alternately, the anvil insert 222 extends to the pin 226 instead of or in addition to the anvil 10. The pin 226 pivotally connects the staple holder 38 to the anvil 10. The pin 226 may be formed into or otherwise fixed to the staple holder 38 or anvil 10, if desired. The anvil 10 and/or anvil insert 222 may extend still further proximally from the pin 226. As one example, the anvil 10 extends proximally to the pin 226. The anvil insert 222 also extends proximally to the pin 226, and additionally extends as far as or further proximally to the proximal end of the anvil 10.

Figure 57:
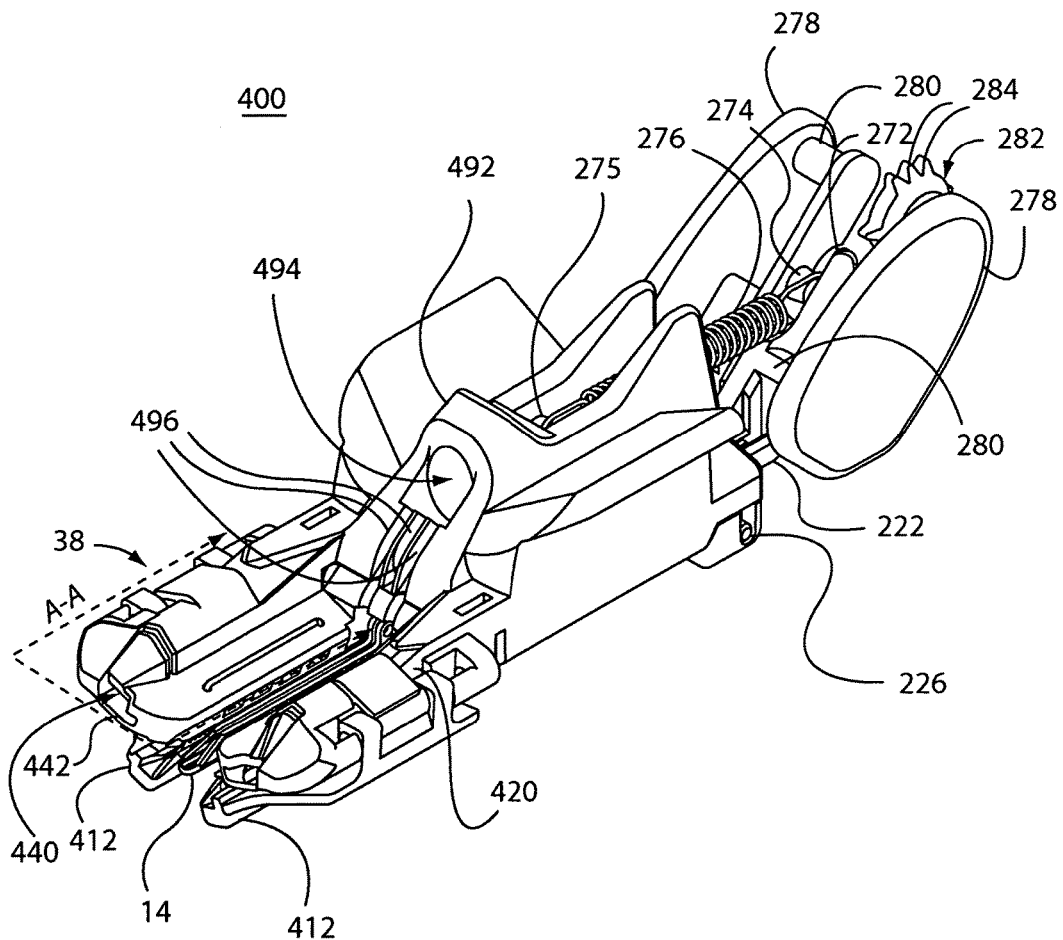
FIG. 57 is a perspective view of the tissue effector of FIG. 55 in a second position.

Referring also to FIG. 57, a proximal portion of the anvil insert 222 may be bent upward relative to a distal portion of the anvil insert 222. The proximal portion of the anvil insert 222 may be referred to as the spine 272. The spine 272 need not be bent upward relative to the proximal portion of the anvil insert 222, and instead may be bent downward or oriented substantially parallel to the proximal portion of the anvil insert 222. Alternately, the spine 272 is a separate structure or mechanism that is connected to the anvil insert 222. A post 274 may be defined in or connected to the spine 272. The post 274 may be cylindrical, or may be shaped differently. One end of a spring 276 is connected to the post 274. The spring 276 is a coil spring, but may be a different type of spring if desired. The other end of the spring 276 is connected to the staple holder 38, such as to an attachment member 275 defined in or connected to the staple holder 38. The attachment member 275 may be cylindrical, or may be shaped differently. The spring 276 may be connected to the post 274 and to the attachment member 275 by hooking an end of the spring 276 to each, by welding, by adhesive, or by any other appropriate structure, mechanism or method. The spring 276 may be connected to the staple holder 38 and/or the spine 272 in a different way, if desired. The spring 276 is sized and configured to be in tension, so as to bias the tissue effector 400 to an open position. That is, the spring 276 presses the staple holder 38 about the pin 226, toward the spine 272 of the anvil insert 222.

Optionally, one or more buttons 278 are connected to the spine 272. The wing or buttons 278 may be spaced apart from the spine 272 and connected to it by one or more connection members 280. The buttons 278 each may be sized and shaped for contact with a user's finger. For example, two buttons 278 may be sized and shaped such that a user may conveniently press one with a thumb and the other with a forefinger. The precise shape and size of the buttons 278 is not critical to the invention. Optionally, at least one button 278 is connected to a cog 282 that in turn connects to the shaft 304 of the anastomosis tool 300, as described in greater detail below. The cog 282 includes one or more teeth 284. Advantageously, the cog 282 is substantially circular, and the teeth 284 extend substantially radially outward from it.

Figure 59:
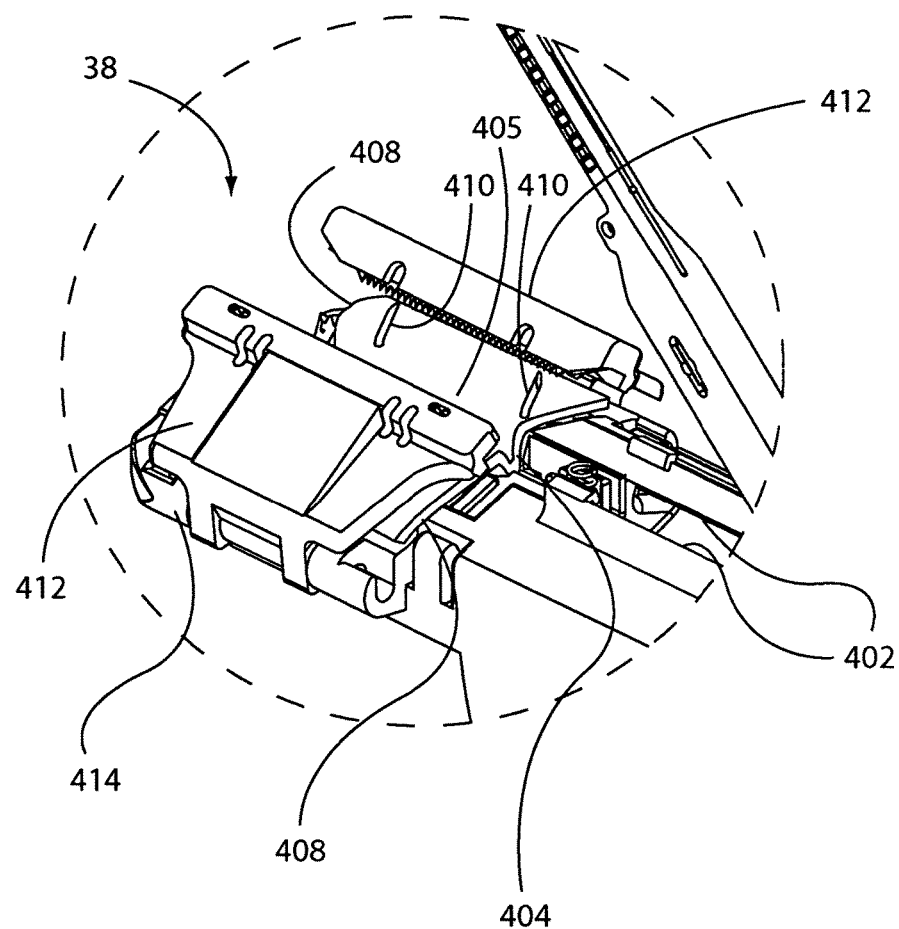
FIG. 59 is a perspective view of the tissue effector of FIG. 55 in the first position, with a graft vessel being connected to it.

Referring to FIG. 58, the underside of the staple holder 38 is seen. The staple holder 38 includes two arms 402, where those arms 402 are spaced apart from one another at least at one end. More or fewer arms 402 may be provided. The arms 402 extend distally from the remainder of the staple holder 38. However, the arms 402 may be positioned differently, if desired. The arms 402 are generally linear in configuration, and the longitudinal centerlines of the arms 402 are substantially parallel to one another. However, the arms 402 may be shaped differently and/or oriented differently relative to one another. One or more of the arms 402 may be angled relative to a horizontal plane to facilitate connecting the flaps of the graft vessel to the wall of the target vessel. Referring also to FIG. 59, the arms 402 are spaced apart from one another at least at one end to allow a graft vessel 404 to be placed between them, and to allow the tissue effector 400 to be freed from the completed anastomosis.

The underside of each arm 402 includes a flap receiving surface 406. Each flap receiving surface 406 is substantially flat across at least a portion of its area. Each flap 408 at the end of the graft vessel 404 is placed onto a corresponding flap receiving surface 406, and the main body of the graft vessel 404 extends between the arms 402 of the staple holder 38. Advantageously, each flap 408 is substantially flat against the corresponding flap receiving surface 406. One or more of the flap receiving surfaces 406 may include a ridged region 413 that has individual ridges 416 spaced apart from one another. The individual ridges 416 may be parallel to one another, or oriented differently. The ridges 416 extend away from the flap receiving surface 406. As one example, each flap receiving surface 406 includes a ridged region 413 in proximity to its inner edge. As used in this document in the context of the staple holder 38, the term "inner" refers to proximity to the space between the arms 402, and the term "outer" refers to distance from the space between the arms 402.

Advantageously, two flaps 408 are present at the end of the graft vessel 404. These flaps 408 may be created in any appropriate manner, such as by incising the end of the graft vessel 404 with a scalpel. However, the end of the graft vessel 404 may have more than two flaps 408. Further, the end of the graft vessel 404 may have a single flap 408. That is, a single incision may be made at the end of the graft vessel 404, substantially parallel to its centerline. As a result, a single flap 408 is created that extends substantially continuously around the circumference of the end of the graft vessel 404, where the opposite ends of the flap 408 are adjacent to the incision.

Optionally, one or more spikes 410 may extend outward from at least one of the flap receiving surfaces 406. As at least one of the flaps 408 is placed onto the corresponding flap receiving surface 406, one or more of the spikes 410 penetrate that flap 408 partially or completely, thereby assisting in holding the flap 408 in place against the flap receiving surface 406.

A graft clip 412 is connected to each arm 402. Each graft clip 412 may be configured to rotate relative to the corresponding arm 402. As one example, each graft clip 412 is pivotally connected to the corresponding arm 402 at or near the outer edge 414 of that arm 402. Alternately, at least one graft clip 412 is movable relative to the corresponding arm 402 in a different way, such as by sliding. Alternately, at least one graft clip 412 is initially a separate component from the arm 402, and is connectable to the corresponding arm 402. Each graft clip 412 is moveable between an open position and a closed position relative to the corresponding arm 402. The graft clip 412 is positioned relative to the flap receiving surface 406 on the corresponding arm 402 such that, in the closed position, the graft clip 412 is configured to engage a flap 408 of the graft vessel 404. The graft clip 412 may engage substantially all of the flap 408, or less than all of the flap 408. Optionally, the graft clip 412 may include ridges 416 corresponding to ridges 416 extending from the flap receiving surface 406.

Alternately, the spikes 410 alone hold the flaps 408 onto the corresponding flap receiving surfaces 406, and one or more graft clips 412 are not used. The spikes 410 are oriented at an angle that facilitates the opening of the tissue effector 400 after the flaps 408 are connected to the target vessel. Where the spikes 410 alone hold the flaps 408, the vein knives 432 that are described below may be omitted, because the staple holder 38 is disengaged from the flaps 408 simply by removal of the spikes 410 from the flaps 408. Thus, by eliminating the graft clips 412, construction of the tissue effector 400 may be simplified. Alternately, a structure or mechanism other than or in addition to the spikes 410 may be used to hold the flaps 408 onto the corresponding flap receiving surfaces 406.

Each graft clip 412 is locked or otherwise held in the closed position to securely hold the flap 408 between itself and the corresponding flap receiving surface 406. The pressure between the graft clip 412 and the flap receiving surface 406, alone or in conjunction with ridges 416 on the graft clip 412 and the flap receiving surface 406 and/or spikes 410 extending upward from the flap receiving surface, holds the flap 408 firmly in place. The spikes 410, if used, may engage the graft clip 412 when it is in the closed position. The ridges 416 on the graft clip 412 and the flap receiving surface 406, if used, engage opposite sides of at least one flap 408, thereby gripping the flap 408 firmly and resisting motion of the flap 408 in a direction substantially perpendicular to the orientation of the ridges 416. However, each graft clip 412 may be shaped or configured in any manner that allows it to participate in holding the corresponding flap 408 to the corresponding flap receiving surface 406.

Figure 59A:
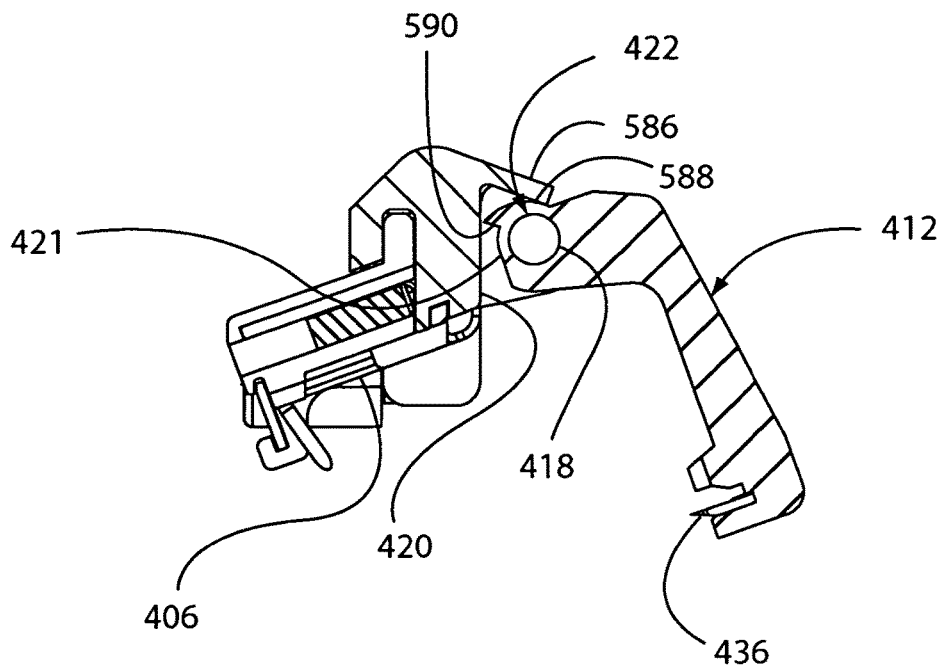
FIG. 59A is a detail cross-section view of a cam lock used in the tissue effector of FIG. 55, where the cam lock is in an open position.

The graft clip 412 may be locked or otherwise held in the closed position with any appropriate mechanism, structure or method. As one example, the graft clip 412 uses a cam lock to hold itself in the closed position. Referring also to FIG. 59A, the graft clip 412 is in an open position. In the open position, the graft clip 412 is positioned to receive a flap 408 of the graft vessel 404 between it and the flap receiving surface 406. The graft clip 412 is rotatable about an axle 418 that is spaced apart from a wall 420 defined on an arm 402 of the staple holder 38. The wall 420 may be perpendicular or otherwise angled to the flap receiving surface 406. The axle 418 is connected to the arm 402, and is substantially fixed relative to the wall 420. Alternately, the axle 418 is movable relative to the wall 420. The axle 418 extends substantially longitudinally, but may be angled relative to the longitudinal direction. The arm 402 also includes an overhang 586 that extends outward and downward from the main portion of the arm 402. Alternately, the overhang 586 extends in a different direction. The overhang 586 may extend laterally outward at least as far as the longitudinal centerline of the axle 418, but need not do so.

The graft clip 412 includes a lobe 422 in proximity to the axle 418, where the lobe 422 has a non-circular cross section. The lobe 422 has a variable thickness, where thickness is defined as the distance between the surface of the axle 418 and the surface of the lobe 422. The lobe 422 includes a first portion 588 that has a relatively small thickness. When the graft clip 412 is in the open position, the first portion 588 is substantially adjacent to the overhang 586. The thickness of the first portion 588 of the lobe 422 is substantially equal to the distance between the axle 418 and the overhang 586. Alternately, the first portion 588 of the lobe 422 may have a different thickness. Moving counterclockwise along the lobe 422, its thickness increases, then decreases rapidly to form a step 590, which may be substantially aligned with the centerline of the axle 418. Continuing to move counterclockwise along the lobe 422, its thickness once again increases. The graft clip 412 may be a mirror image of the clip 412 shown in FIG. 59A, such that the thickness of the lobe 422 relative to the angular position thereon is reversed from the description above. Similarly, if the graft clip 412 is viewed from the opposite direction, the thickness of the lobe 422 will be reversed from the description above. The operation of the graft clip 412 is the same.

In the open position, which is the initial position of the graft clip 412, the first portion 588 of the lobe 422 is adjacent to the overhang 586. This first portion 588 may be substantially as thick as the distance between the axle 418 and the overhang 586. The portion of the lobe 422 adjacent to and immediately clockwise from the step 590 may be in contact with or in proximity to the wall 420. The graft clip 412 is rotated about the axle 418 from the open position to the closed position in a clockwise direction by the user or by a mechanism associated with the tissue effector 400. As this rotation begins, increasingly-thick portions of the lobe 422 move between the axle 418 and the overhang 586. As a result, the overhang 586, axle 418, and/or lobe 422 may flex to accommodate the increased amount of thickness of the lobe 422 between the axle 418 and the overhang 586. Further, this increase in thickness between the axle 418 and the overhand 586 may provide at least some resistance to the motion of the graft clip 412.

Figure 59C:
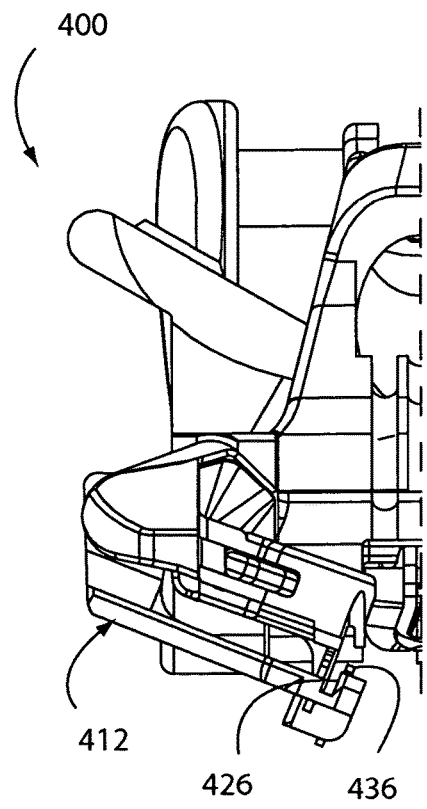
FIG. 59C is an end view of the left half of the tissue effector of FIG. 55, in the closed position.
Figure 60:
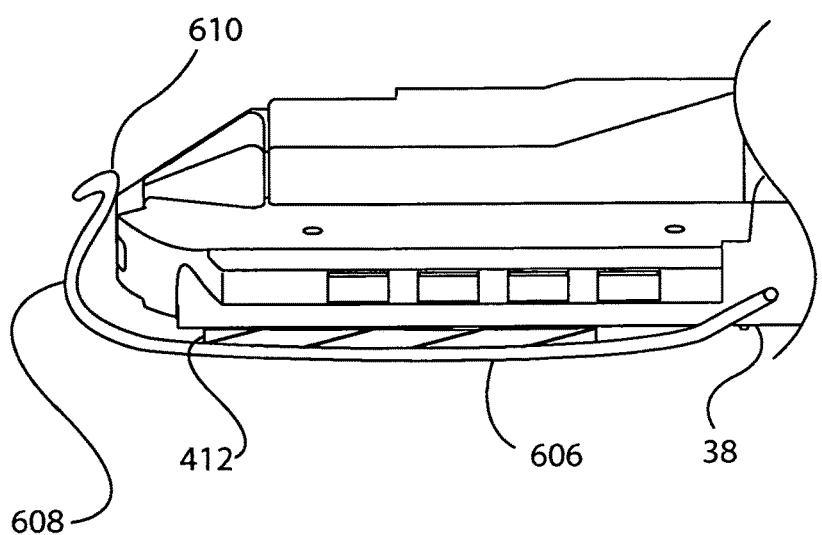
FIG. 60 is a detail side view of a portion of the tissue effector of FIG. 55, showing an embodiment of a graft clip.

Referring also to FIG. 60, as the rotation of the graft clip 412 continues, the step 590 encounters the overhang 586, then moves past the overhang 586. As a result, the thickness of the lobe 422 between the overhang 586 and the axle 418 decreases abruptly. The stiffness of the overhang 586 is such that the overhang 586 can flex enough to allow the graft clip 412 to rotate past the step 590. Rotation of the graft clip 412 may stop at or shortly after the motion of the step 590 past the overhang 586, such that the graft clip 412 stops at the closed position shown in FIG. 59C. Motion of the graft clip 412 in the counterclockwise direction would cause the step 590 to encounter the end of the overhang 586, stopping the rotation of the graft clip 412. Thus, the step 590 acts to hold the graft clip 412 in the closed position.

Alternately, a structure or mechanism other than a cam lock may be used to hold the graft clip 412 in a closed position. As one example, at least one elastic band (not shown) may be used to hold the graft clip 412 against the staple holder 38. Each elastic band may be fixed to either the graft clip 412 or the staple holder 38. As another example, the graft clip 412 and the corresponding arm 402 may each include corresponding magnets (not shown), such that magnetic force holds the graft clip 412 in contact with the arm 402 in the closed position.

As another example, referring to FIG. 60, a snap arm 606 may be used to hold the graft clip 412 in a closed position. The snap arm 606 is connected at one end to the corresponding arm 402. This connection may be a hinge, or may be any other connection that allows the snap arm 606 to move between an open position, in which the graft clip 412 may be opened, and a closed position, in which the graft clip 412 is held closed. The connection between the proximal end of the snap arm 606 and the arm 402 is made proximal to the flap receiving surface 406. Alternately, the connection between the snap arm 606 and the staple holder 38 is made at a different location. Alternately, a different part of the snap arm 606 than its proximal end is connected to the arm 402.

The distal end of the snap arm 606 includes a catch 608 that is shaped to engage the distal end of the corresponding arm 402. For example, the catch 608 may be curved such that a lobe 610 of the catch 608 is proximal to the distal end of the arm 402 when the snap arm 606 is in the closed position, thereby holding the snap arm 606, and the graft clip 412, in place. The catch 608 is at least partially flexible such that the catch 608 can be snapped down onto the distal end of the corresponding arm, thereby holding the snap arm 606 in the closed position. The catch 608 may be configured differently, if desired. When the snap arm 606 is in the closed position, at least a portion of the graft clip 412 is positioned between the snap arm 606 and the corresponding arm 402. Thus, in the closed position, the snap arm 606 presses the graft clip 412 against the arm 402, holding it in place. As a result, the graft clip 412 holds the corresponding flap 408 against the flap receiving surface 406.

Alternately, a separate snap arm 606 is not used, and the graft clip 412 itself includes a catch 608 that engages the corresponding arm 402 of the tissue effector 400. Alternately, the snap arm 606, or the graft clip 412 that includes a catch 608, is oriented differently, such as described above with regard to FIGS. 59A-59B.

Figure 61:
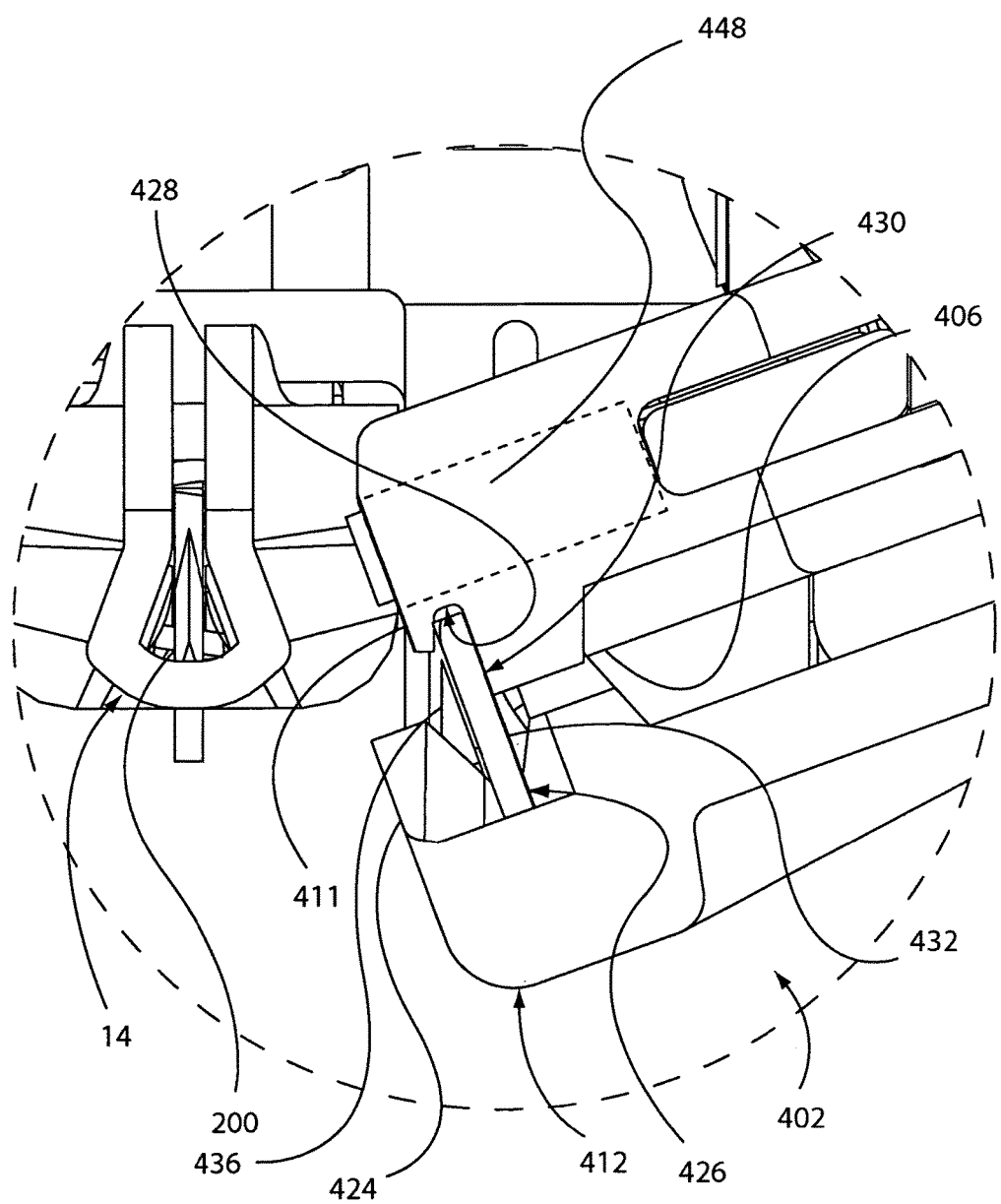
FIG. 61 is a detail end view of a portion of the tissue effector of FIG. 55.

Referring also to FIG. 61, in the closed position, each graft clip 412 is configured to press a flap 408 of the target vessel against the corresponding flap receiving surface 406. The flap 408 is not shown for clarity. In the closed position, the graft clip 412 and the flap receiving surface 406 are substantially fixed relative to one another. The graft clip 412 and the corresponding flap receiving surface 406 may be configured such that a portion of each would contact the other in the closed position, absent the flap 408. Thus, where the flap 408 is present, the graft clip 412 compresses the flap 408 against the flap receiving surface 406. Additionally, the graft clip 412 may include an overhang 424, which extends along at least a portion of the edge of the graft clip 412. The overhang 424 may be substantially parallel to and in proximity to the corresponding inner edge 411 of the arm 402 in the closed position. Alternately, the overhang 424 may be configured differently relative to the arm 402. The overhang 402 may bend the flap 408 and/or press, pinch or otherwise hold it against the corresponding edge of the arm 402.

Still referring to FIG. 61, a first channel 426 may be defined in the graft clip 412, and a corresponding second channel 428 may be defined in the arm 402. The first channel 426 and the second channel 428 are substantially linear and substantially aligned with one another. Alternately, the first channel 426 and the second channel 428 are configured differently, aligned differently with respect to one another and/or have a different cross-section. Each channel 426, 428 is open along one side, at least in part. The first channel 426 and the second channel 428 are oriented and aligned relative to one another such that the openings in the channels 426, 428 face one another to form a vein knife passage 430. The channels 426, 428 may be spaced apart from one another at least in part and still form the vein knife passage 430; that is, the vein knife passage 430 need not be bounded around its entire periphery. Alternately, the channels 426, 428 are oriented and aligned differently, and/or the vein knife passage 430 is formed differently. Each vein knife passage 430 is oriented such that, when the tissue effector 40 is in the closed position, the longitudinal centerline of the vein knife passage 430 is substantially parallel to the longitudinal axis of the anvil 10. Alternately, the vein knife passages 430 are aligned differently relative to the longitudinal axis of the anvil 10 when the tissue effector 400 is in the closed position.

Figure 62:
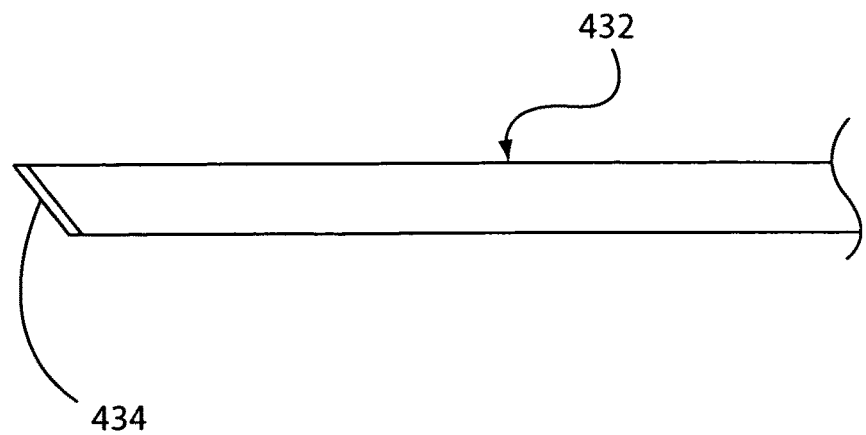
FIG. 62 is a side view of a vein knife used in the tissue effector of FIG. 55.

Referring also to FIG. 62, at least one vein knife passage 430 is configured to receive a corresponding vein knife 432. The fit between the dimensions of the vein knife 432 and the corresponding vein knife passage 430 is close enough that the vein knife passage 430 guides the vein knife 432 and substantially prevents wobbling or other disruption of the motion of the vein knife 432 as it travels along the vein knife passage 430, and loose enough to allow the vein knife 432 to slide easily along that vein knife passage 430 substantially without binding or interference. Each vein knife 432 has a blade 434 or other sharp element at its distal end. The blade 434 of at least one vein knife 432 may be angled. Alternately, the blade 434 of at least one vein knife may be curved or otherwise shaped. The proximal end of each vein knife 432 is connected to a sled, which is described in greater detail below. The vein knife 432 is configured to translate or otherwise move between a first position and a second position. In the first position, the blade 434 of the vein knife 432 is located proximal to the flap 408 held between the graft clip 412 and the flap receiving surface 406. The vein knife 432 translates or otherwise moves to the second position and cuts the flap 408 as it does so. In the second position, the blade 434 of the vein knife 432 is located adjacent or distal to the portion of the flap 408 held between the graft clip 412 and the flap receiving surface 406. The first and second positions are reversed when the vein knife 432 is moved in the opposite direction.

Figure 63:
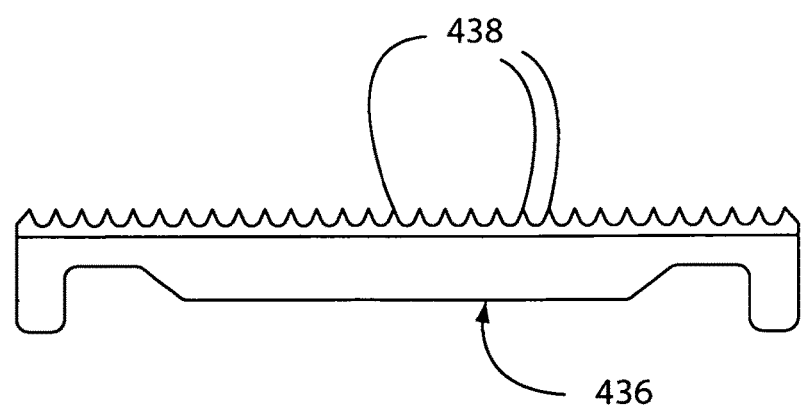
FIG. 63 is a side view of a graft clip blade used in the tissue effector of FIG. 55.

Optionally, one or more graft clip blades 436 are connected to at least one graft clip 412. Referring also to FIG. 63, one or more of the graft clip blades 436 may be serrated. Each graft clip blade 436 is located in and against one side of the first channel 426, such that it does not interfere with the motion of the vein knife 432. Alternately, one or more graft clip blades 436 are located in a different position on the corresponding graft clip 412 or arm 402. Serrations 438 on the graft clip blade 436 are oriented toward the open face of the first channel 426 in the graft clip 412. The serrations 438 may be sized and shaped in any appropriate manner. The serrations 438 assist in holding the flap 408 between the graft clip 412 and the flap receiving surface 406. That is, one or more of the serrations 438 may penetrate into or through the flap 408, thereby holding the tissue of the flap 408 substantially fixed relative to the graft clip 412 and the flap receiving surface 406. When the vein knife 432 translates along the vein knife passage 430 to incise the flap 408, the serrations 438 hold the flap 408. The motion of the vein knife 432 may apply stress to the tissue of the flap 408 such that the serrations 438 themselves act to cut the tissue of the flap 408. Thus, the cutting action may be a scissors-like action resulting from the relative motion of the vein knife 432 and the graft clip blade 436. More than one graft clip blade 436 can be provided in at least one vein knife passage 430. For example, two graft clip blades 436 may be located in one first channel 426, in and against two different sides of the first channel 426 and spaced apart from one another a sufficient distance to allow the vein knife 432 to slide therebetween. Other configurations or numbers of graft clip blades 436 may be utilized, if desired.

Figure 59B:
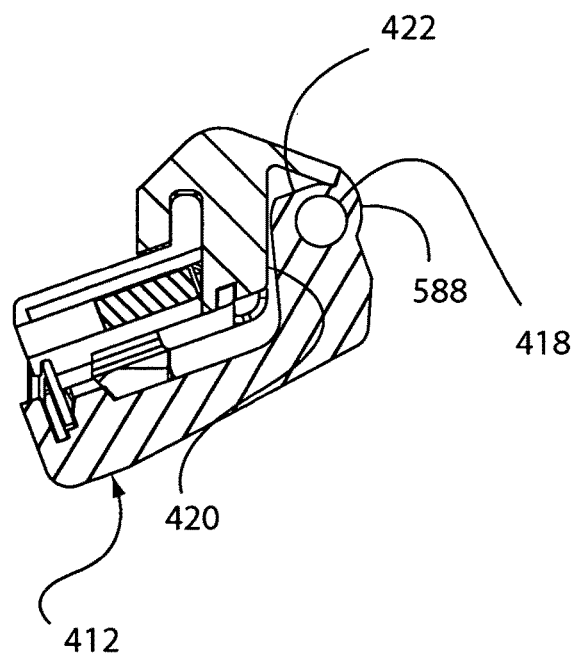
FIG. 59B is a detail cross-section view of the cam lock of FIG. 59A in a closed position.
Figure 59D:
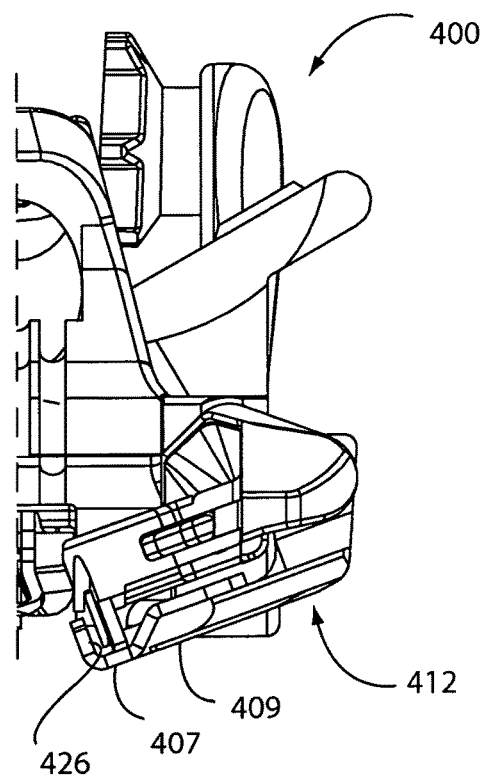
FIG. 59D is an end view of the right half of another embodiment of the tissue effector of FIG. 55, in the closed position.

Alternately, referring to FIG. 59D, at least one graft clip 412 may have a thinner cross-section than the graft clip 412 of FIGS. 59-59B. This thinner cross-section may be achieved by utilizing metal, such as sheet metal, to form at least part of the graft clip 412. However, metal need not be used in order for the graft clip 412 to be made thinner. As shown in FIG. 59C, the graft clip 412 may be an assembly having a first piece 407 connected to a second piece 409. The first piece 407 is located at or near the first channel 426 of the graft clip 412. Alternately, the graft clip 412 may be a single-piece, or may be an assembly having additional components. The second piece 409 may be made of plastic or any other suitable material. Other materials may be used to form the pieces 407, 409 if desired. Advantageously, the graft clip blades 436 may be formed into the first piece 407, particularly where at least the first piece 407 of the graft clip 412 is metal. By forming the graft clip blades 436 into a portion of the graft clip 412 rather than connecting them to the graft clip 412, construction of the graft clip 412 may be simplified.

The use of a thinner graft clip 412 results in less compression of the surface of the heart, where the target vessel is a coronary artery and the anvil arm 14 is inserted into that coronary artery. The vertical distance between the bottom of the anvil arm 14 and the bottom of the graft clip 412 substantially defines the distance across which the heart tissue near the coronary artery is compressed as the tissue effector 400 moves from the open to the closed position. By decreasing that distance, the heart tissue around the coronary artery is compressed a lesser distance. As a result, the amount of force required to move the tissue effector 400 from an open position to a closed position, in which compressive force is applied against the heart tissue, may be decreased. This reduction in force may simplify the construction of the tissue effector 400.

Figure 64:
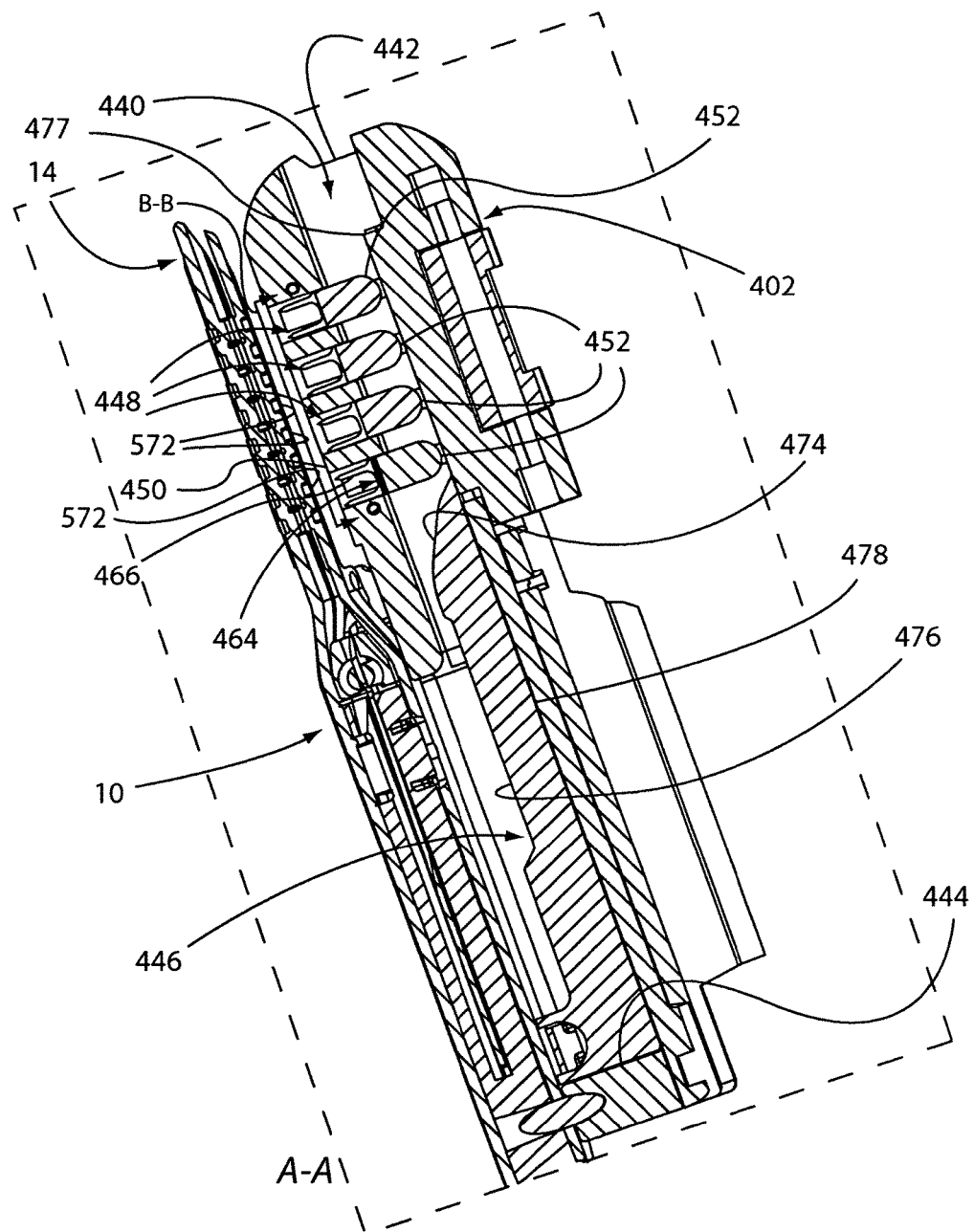
FIG. 64 is a cross-section view of section A-A of FIG. 57.

Referring also to FIG. 64, a cross-section of one arm 402 of the staple holder 38 is shown. The staple holder 38 is substantially symmetrical, such that the arm 402 shown is substantially a mirror image of the other arm 402. Alternately, the staple holder 38 is not symmetrical, and/or the arms 402 are not mirror images of one another. A passage 440 is defined within each arm 402. Each passage 440 extends substantially longitudinally within the corresponding arm 402, and the longitudinal centerline of each passage 440 is substantially parallel to the longitudinal centerline of the anvil 10 when the tissue effector 400 is in the closed position. Alternately, at least one passage 440 is oriented differently relative to its corresponding arm 402. The passage 440 may have a rectangular cross-section, or a different cross-section. Further, the dimensions of the passage 440 may be substantially constant along its entire length, or may change along at least part of its length. Optionally, the distal end 442 of the passage 440 is open, and/or the proximal end 444 of the passage 440 is open.

Figure 69A:
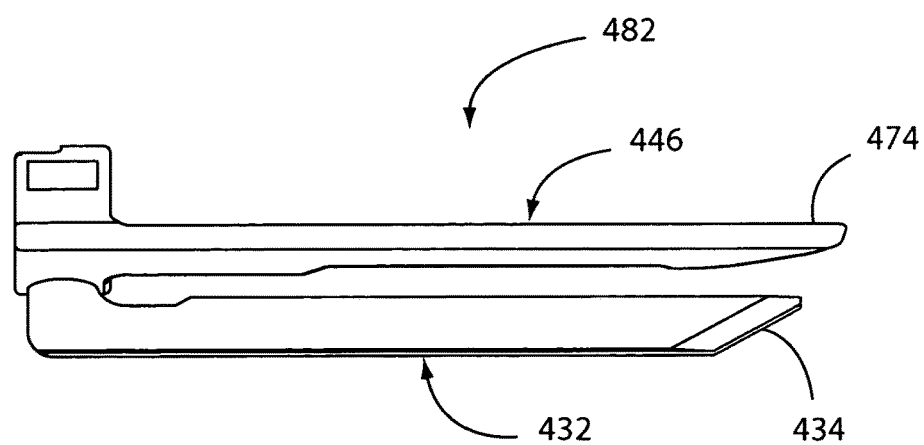
FIG. 69A is a side view of the sled of FIG. 68.

A ramp element 446 is configured to translate or otherwise move through at least a portion of each passage 440. Referring also to FIGS. 68-69A, the ramp elements 446 may be molded or otherwise formed into a unitary ramp element assembly 484, or may be molded or otherwise formed separately and then connected together. The ramp elements 446 may be formed from stainless steel or other appropriate material. The vein knives 432 are connected to the ramp element assembly 484 to form a sled 482. As an example, apertures 486 are defined in the ramp element assembly 484, and the proximal end of each vein knife 432 is sized and shaped to provide for a pressure or interference fit within the corresponding aperture 486. However, any other appropriate mechanism, structure or method may be used to connect each vein knife 432 to the ramp element assembly 484. Alternately, the ramp elements 446 and the vein knives 432 are cast, molded or otherwise formed as a single unit. The vein knives 432 are fixed to the ramp element assembly 484, such that the ramp elements 446 and the vein knives 432 translate as a unit substantially simultaneously. Alternately, at least one ramp element 446 is moveable relative to at least one vein knife 432. As another example of the sled 482, each ramp element 446 is connected to the corresponding vein knife 432, but the ramp elements 446 are not connected to one another.

The sled 482 includes an attachment feature 488. The attachment feature 488 may be an aperture through a portion of the ramp element assembly 484 that is configured to receive a second cable 490 or other force transmission mechanism or structure. Where a cable is used and the attachment feature 488 is an aperture, the second cable 490 may be inserted into and/or through the attachment feature 488, and held in place there such as by tying off one end of the cable, by welding, by adhesive, or any other appropriate connection method. Alternately, the attachment feature 488 may be a ring, a hook, a raised area, a depression, or any other structure or mechanism appropriate for connection to a cable or other force transmission mechanism or structure.

One or more connector bays 448 are defined in each arm 402, between the passage 440 within the arm 402 and an inner surface 450 of the arm 402. The connector bays 448 and the passages 440 are substantially hollow. The cross-sectional shape of each connector bay 448 is selected to allow it to receive and hold a staple, as described below. The connector bays 448 are oriented such that the longitudinal centerline of each connector bay 448 is substantially perpendicular to the longitudinal centerline of the corresponding passage 440. Alternately, at least one connector bay 448 is oriented differently relative to the corresponding passage 440. Each connector bay 448 has substantially the same cross-section and length. Alternately, at least one connector bay 448 has a different cross-section and/or length than at least one other connector bay 448. The connector bays 448 may be oriented relative to a local horizontal such that the longitudinal centerline of each connector bay 448 forms an angle of between 0° and 45° relative to that local horizontal. A different orientation may be used, if desired. The use of the term "horizontal" here and elsewhere in this document is used for convenience in description only, and does not restrict the orientation in which the anastomosis tool 300 may be used.

Figure 65:
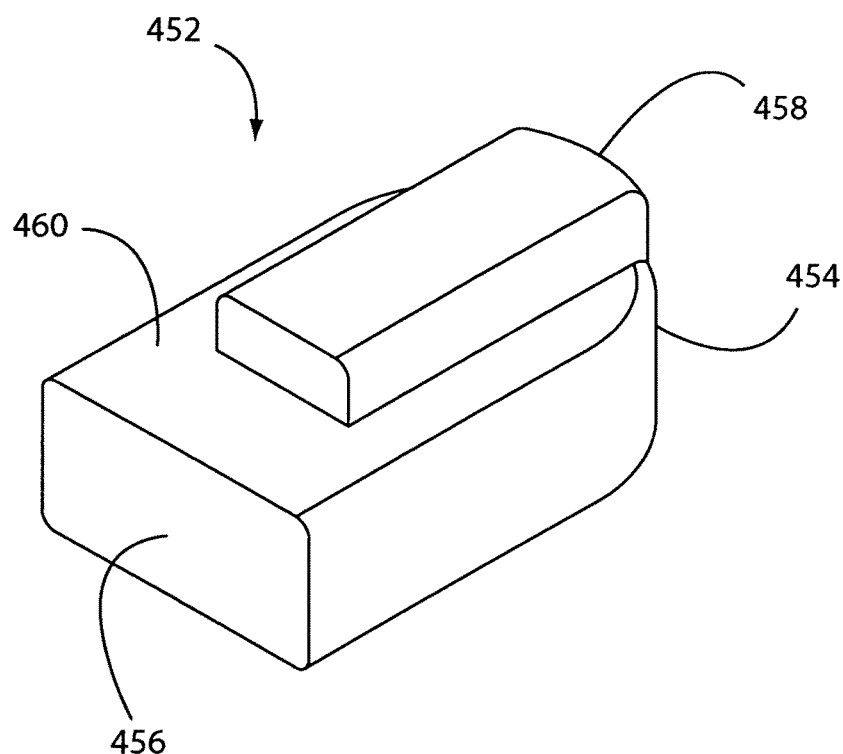
FIG. 65 is a perspective view of a connector deployer used in the arm of FIG. 64.
Figure 66:
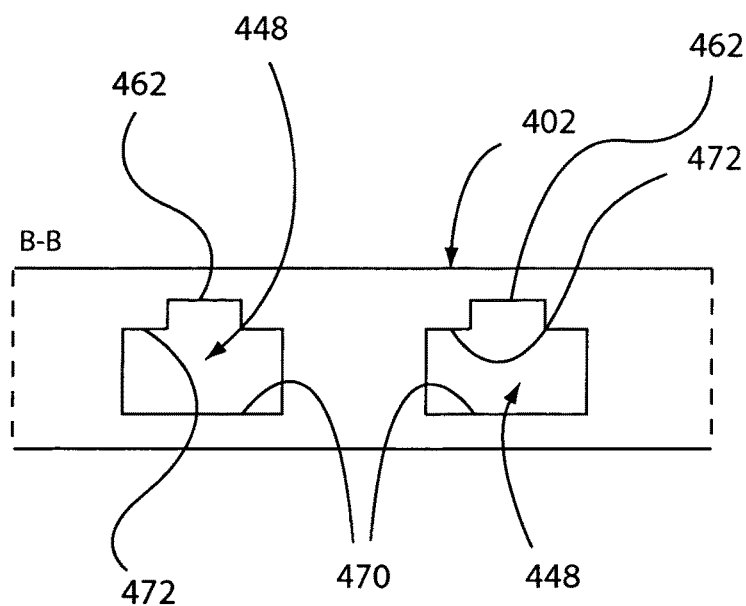
FIG. 66 is a side view of a portion of the arm of FIG. 64 as defined by the line B-B of FIG. 64.

Referring also to FIG. 65, at least one connector bay 448 is configured to receive a connector deployer 452. Each connector bay 448 is shaped to allow the corresponding connector deployer 452 to translate or otherwise move within it. The sliders 452 may be shaped in any appropriate manner. As one example, a connector deployer 452 is substantially curved at its outer end 454 and substantially flat at its inner end 456. The connector deployer 452 may vary in height along at least a portion of its length and/or width. As one example, a registration element 458 may extend upward from the upper surface 460 of the connector deployer 452. The registration element 458 may be formed into the connector deployer 452, or otherwise manufactured into it or connected to it.

Where a registration element 458 is used, the corresponding connector bay 448 is shaped accordingly. That is, the size, shape and orientation of the registration element 458 of the connector deployer 452 corresponds to the size, shape and orientation of a registration feature 462 of the connector bay 448. For example, where the connector deployer 452 and registration element 458 of FIG. 65 is used, the corresponding connector bay 448 is shaped as shown in FIG. 66. The registration element 458 translates along the registration feature 462 as the connector deployer 452 translates along the connector bay 448. In this way, the connector deployer 452 is maintained in a desired orientation throughout its translation relative to the connector bay 448, and the connector deployer 452 is prevented from cocking in the connector bay 448 during that translation. The sliders 452 and corresponding connector bays 448 may be shaped differently, if desired. The sliders 452 are all shaped substantially identically. Alternately, at least one of the sliders 452 is shaped differently from at least one of the others, and the corresponding connector bay or bays 448 are shaped accordingly. Optionally, a biocompatible lubricant such as sodium stearate may be used between at least one connector deployer 452 and the corresponding connector bay 448 to facilitate the translation of the connector deployer 452 relative to the connector bay 448.

Each connector deployer 452 is moveable between a first position and a second position. In the first position, the outer end 454 of the connector deployer 452 extends at least partially into the passage 440. Alternately, the outer end of the connector deployer 452 does not extend into the passage 440. In the second position, the connector deployer 452 has translated relative to the corresponding connector bay 448 and completed its motion. The outer end 454 of the connector deployer 452 no longer extends into the passage 440. Alternately, the outer end 454 of the connector deployer 452 still extends into the passage 440 in the second position. Each connector deployer 452 translates or otherwise moves from the first position to the second position as a result of contact with the ramp element 446. This translation is described in greater detail below.

Figure 67:
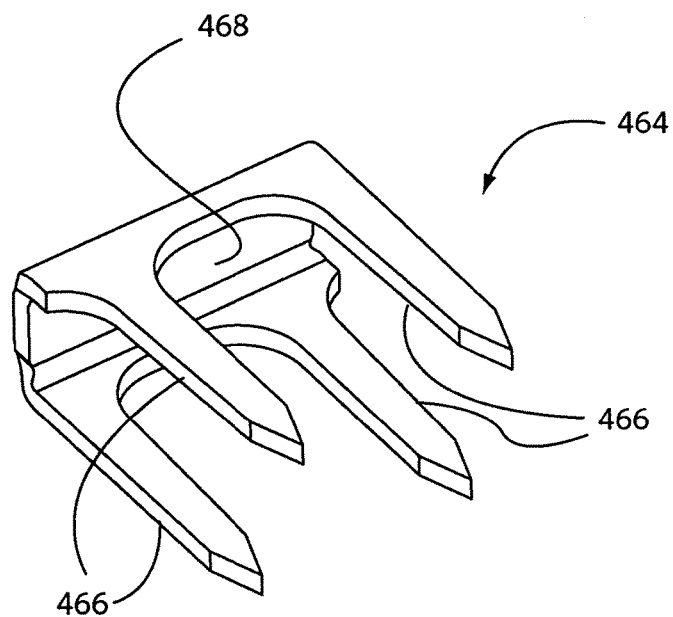
FIG. 67 is a perspective view of a staple configured to be deployed from the tissue effector of FIG. 55.

A connector 464 is placed in at least one connector bay 448. In an exemplary embodiment shown in FIG. 64, the connector 464 is a staple. Each connector 464 is located closer to the inner surface 450 of the arm 402 than the corresponding connector deployer 452. The connector 464 may be configured as disclosed in pending U.S. patent application Ser. No. 10/309,519 filed on Dec. 4, 2002, which is hereby incorporated by reference in its entirety. As one example, referring also to FIG. 67, the connector 464 includes four tines 466 extending from a base 468. The tines 466 may be offset from one another. A different configuration of connector 464 may be used, if desired. The connector 464 is constructed from 316L stainless steel, but may be constructed from a different type of stainless steel, or from a different material. As another example, the connector 464 may be a connector other than a staple, such as a pin or clip.

Each connector 464 is oriented in the connector bay 448 such that the tines 466 extend in a direction facing substantially out of the connector bay 448. Alternately, each connector 464 is oriented differently. The base 468 of the connector 464 may be in contact with the inner end of the corresponding connector deployer 452 when that connector deployer 452 is in the first position, or may be spaced apart from the inner end of that connector deployer 452 in the first position. When the connector deployer 452 is in the first position, the corresponding connector 464 is held within the connector bay 448 in any appropriate way. Referring also to FIG. 66, as one example, the tines 466 of each connector 464 may be biased against at least part of the corresponding connector bay 448. For example, at least one tine 468 may be biased against a lower surface 470 of the connector bay 448 and at least one other tine 469 may be biased against an upper surface 472 of the connector bay 448. The biasing force exerted by each tine 468 against the corresponding surface 470, 472 of the connector bay 448 holds the connector 464 in place when the connector deployer 452 is in the first position. The biasing forces exerted by the tines 468 are high enough to hold the connector 464 securely within the connector bay 448, and are low enough to allow the connector 464 to translate easily as a result of contact with the corresponding connector deployer 452. As another example, each connector 464 may be held in place in the corresponding connector bay 448 with a biocompatible substance that provides friction between that connector 464 and the connector bay 448, where the amount of force required to overcome that friction and move the connector 464 is selected to be less than the amount of deployment force to be exerted on the connector 464 by the corresponding connector deployer 452. The translation of a connector deployer 452 from the first position to the second position causes deployment of the corresponding connector 464, as described in greater detail below.

The ramp element 446 translates or otherwise moves within the passage 440, as described above. The distal end 474 of the ramp element 446 is configured to engage the sliders 452 as it moves, causing those sliders 452 in turn to translate or otherwise move relative to their respective connector bays 448. As one example, the ramp element 446 is curved and/or angled at its distal end 474, where the curvature and/or angularity begins at or near the most distal point of the ramp element 446 and continues proximally along the inner surface 476 of the ramp element 446. That is, the ramp element 446 increases in width from its most distal point to a selected point spaced apart from and proximal to that most distal point. The ramp element 446 may be shaped such that the curvature and/or angularity of the distal end 474 is present on the inner surface 476 of the ramp element 446, and such that the outer surface 478 of the ramp element 446 is substantially flat against a wall of the passage 440. However, the ramp element 446 may be shaped in any other appropriate manner. The ramp element 446 may be translated distally along at least a portion of the passage 440. In the course of this translation, the distal end 474 of the ramp element 446 sequentially contacts and thereby actuates the sliders 452, beginning with the most proximal and concluding with the most distal. Alternately, the ramp element 446 translates proximally to contact and actuate sequentially the sliders 452, beginning with the most distal and concluding with the most proximal. Alternately, the ramp element 446 is configured to move in such a manner that at least a component of its motion is toward the inner surface 450 of the arm 402, such that the ramp element 446 engages more than one connector deployer 452 at a time. Thus, the ramp element 446, another component of the sled 482, or a different component may actuate the sliders 452 serially or in parallel.

Optionally, one or more of the sliders 452 are omitted from the tissue effector 400, such that the ramp element 446 and/or a different component of the sled 482 directly contacts one or more of the staples 464 to urge that staple or staples 464 out of the corresponding arm 402. That is, the intermediate mechanism between the sled 482 and at least one of the staples 464 may be omitted. If so, the sled 482 and/or at least one connector 464 are configured such that contact between them urges the connector 464 in the desired direction. For example, one or more of the staples 464 may include a structure analogous to the connector deployer 452 formed into it, where that structure is implanted into the patient along with the connector 464. This additional structure is small, and is positioned outside the lumen of both the graft vessel and the target vessel, such that its presence in the patient has no effect. Such a structure may be composed of stainless steel or other biocompatible material, or from bioabsorbable material that is gradually absorbed by the patient. Such biocompatible and bioabsorbable materials are standard in the art.

Optionally, one or more of the connector bays 448 may be omitted from one or more of the arms 402 of the tissue effector 400. For example, if the staples 464 are deployed in parallel, the staples 464 may be connected to the sled 482 or other component such as by adhesive, where that connection is able to withstand an amount of force less than the force with which the deployed connector 464 grips the graft vessel 404 and the target vessel 580. As a result, after the staples 464 are deployed into tissue and grip the vessels 404, 580 and the sled 482 or other component is pulled away from the anastomosis, the connection between each connector 464 and the sled 482 or other component is broken, thereby freeing the staples 464 from the tissue effector 400.

Figure 74:
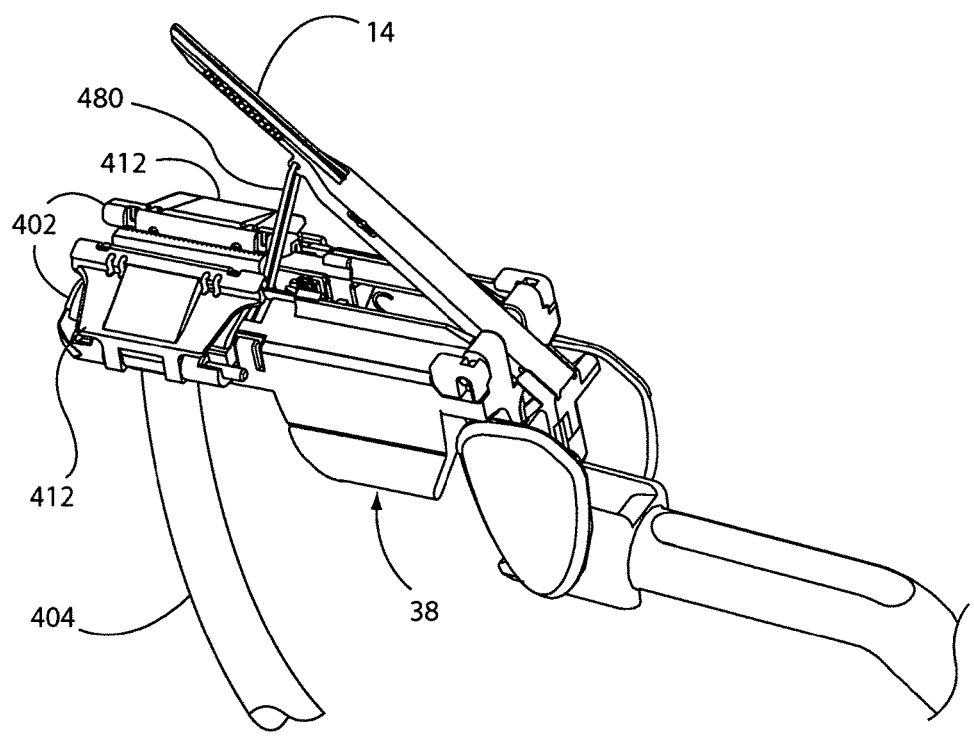
FIG. 74 is a perspective view of the tissue effector of FIG. 55 with a graft vessel loaded onto it.

Referring also to FIGS. 58 and 74, the anvil 10 is connected to a force transmission mechanism such as a first cable 480. As described above, the anvil 10 may include a cutter stop 236 having one or more attachment features 270 to which the first cable 480 is connected. However, the first cable 480 may be connected to a different or an additional part of the anvil 10.

The sled 482 is connected to a force transmission mechanism such as a second cable 490. As described above, the sled 482 includes an attachment feature 488 to which the second cable 490 is connected. However, the second cable 490 may be connected to a different or an additional part of the sled 482. Alternately, one or both of the cables 480, 490 are not used, and a different force transmission mechanism is used instead. For example, one or both force transmission mechanisms may be a chain, a shaft, one or more gears, one or more tubes for handling pressurized gas or vacuum, conductive elements for carrying electricity, and/or other appropriate mechanisms.

The cables 480, 490 extend proximally from the tissue effector 400. Optionally, a cable housing 306 is provided. The cable housing 306 is a tube that is at least partially flexible, through which at least a portion of the cables 480, 490 extend. Two or more lumens or passages may be present in the cable housing 306, such that each cable 480, 490 extends through a different lumen or passage. Referring also to FIG. 57, the staple holder 38 includes a collar 492. The collar 492 may be formed into the staple holder 38, or formed separately from and attached to the staple holder 38. The collar 492 includes a passage 494 therethrough. The diameter of the passage 494 may be substantially the same as the outer diameter of the cable housing 306, such that the distal end of the cable housing 306 may be received into and/or through the collar 492 and held therein. Similarly, the shape of the passage 494 may substantially correspond to the shape of the distal end of the cable housing 306. The distal end of the cable housing 306 is fixed to the collar 492 via a friction fit, adhesive, welding, or any other appropriate structure, mechanism or method. The cable housing 306 need not have a uniform shape, size or cross-section along its entire length. Alternately, the distal end of the cable housing 306 may connect to a different portion of the tissue effector 400, or may not connect to the tissue effector 400 at all. Additionally, the cable housing 306 may pass over and/or connect to one or more of the connection members 280 of the tissue effector 400, and/or one or more other components of the tissue effector 400.

One or more channels 496 may be defined on the surface of the staple holder 38 distal to the collar 492. Each channel 496 receives a cable 480, 490. At least one channel 496 may be curved in a convex manner, such that the corresponding cable 480, 490 curves as well. The convex curvature causes the most distal part of that channel 496 to be located between the upper and lower ends of the channel 496. The cable 480, 490 in that channel 496 may be under tension, such that it follows the curvature of that channel 496. Thus, the channel 496 causes the cable 480, 490 received therein to curve back in a proximal direction. For example, the second cable 490 is connected to the sled 482. Tension on the second cable 490 that results from proximal motion of its proximal end also results in distal motion of the sled 482.

Referring also to FIG. 56, the shaft 304 may be bifurcated at its distal end, forming two spaced-apart arms 305. The cable housing 306 passes between the arms 305, such that the arms 305 constrain the potential lateral motion of the cable housing 306. Alternately, the cable housing 306 does not pass between the arms 305. At least one arm 305 forms or connects to a paddle 307 at its distal end. The cable housing 306 extends in a curved configuration, such as an S-shaped or serpentine configuration, between the shaft 304 and the tissue effector 400. The paddle or paddles 307 may be substantially planar and parallel to one another. A receiving opening 309 is provided through at least one paddle 307, each opening corresponding to a cog 282 of the tissue effector 400. One or more detents 310 are present along the perimeter of the receiving opening 309, corresponding to the teeth 284 of the cog 282. The teeth 284 are configured to engage the detents 310 in the receiving opening 309. The button 278 connected to the cog 282 may be connected to the spine 272 with a single connection member 280 spaced apart from the cog 282, or may be connected to the spine 272 with one or more flexible connection members 280. As a result, the buttons 278 can be compressed together, such that the teeth 284 are moved out of engagement with the corresponding detents 310. The cog 282 thus can be moved to a position out of contact with the receiving opening 309, such that it is located between the paddles 307. Consequently, the cog 282 and the tissue effector 400 can be freely rotated to a desired orientation. The buttons 278 are then released, such that the cog 282 re-enters the receiving opening 309 and the teeth 284 engage the detents 310 in the receiving opening 309 once again. Alternately, the cog 282 engages a corresponding gear or other structure or mechanism in or on the shaft 304, such that motion of the corresponding gear rotates the cog 282. Alternately, the cog 282 is connected to the shaft 304 or one or more components in and/or on the shaft 304 in such a way that the cog 282 can be rotated or otherwise manipulated as desired. Alternately, the tissue effector 38 is connected to the shaft 304 with a mechanism or structure other than or in addition to the cog 282.

The cog 282 allows the tissue effector 38 to be oriented at a plurality of positions relative to the shaft 304. That is, the cog 282 allows the tissue effector 38 to move such that the longitudinal centerline of the tissue effector 38 may be positioned at more than one angle relative to the longitudinal centerline of the shaft 304. The cog 282 or other mechanism may allow the tissue effector 38 to move smoothly through a range of orientations relative to the handle 302, or may allow the tissue effector 38 to move among two or more discrete orientations relative to the handle 302. Thus, the tissue effector 38 is orientable to two or more different positions relative to the handle 302. The relative motion between the tissue effector 38 and the shaft 304 allows the tissue effector 38 to be utilized on target vessels having a number of different orientations within the patient, while allowing convenient access by the surgeon or other medical professional. That is, the surgeon may hold the handle 302 in a single convenient position, and orient the tissue effector 38 into a selected position relative to the shaft 304 and handle 302 that is optimal for use with a particular target vessel. Optionally, the arms 305 or a mechanism connected to the arms may be capable of rotation relative to the shaft 304, providing additional freedom of motion for the tissue effector 38. Alternately, the cog 282 is not present, and the arms 305 otherwise allow motion of the tissue effector 38 relative to the shaft 304. Alternately, the tissue effector 400 is fixed relative to the shaft 304.

Referring also to FIG. 55, the shaft 304 is substantially hollow along at least part of its length, starting at its proximal end and continuing distally. The entire shaft 304 may be substantially hollow. An aperture 498 or other opening is located in the wall of the shaft 304 at a point along its length where it is hollow. Thus, the aperture 498 provides access to the lumen of the shaft 304. The cable housing 306 extends through the aperture 498 into the lumen of the shaft 304. Alternatively, the cable housing 306 does not enter the lumen of the shaft 304, and instead is attached to the outer surface of the shaft 304 with adhesive, clips, pins, and/or any other appropriate attachment mechanisms, structures or methods. If so, the shaft 304 need not include a lumen. Alternately, the cable housing 306 does not connect to the shaft 304 at all, and instead connects to the handle 302 directly. If so, the shaft 304 need not include a lumen, and may be solid.

Figure 70:
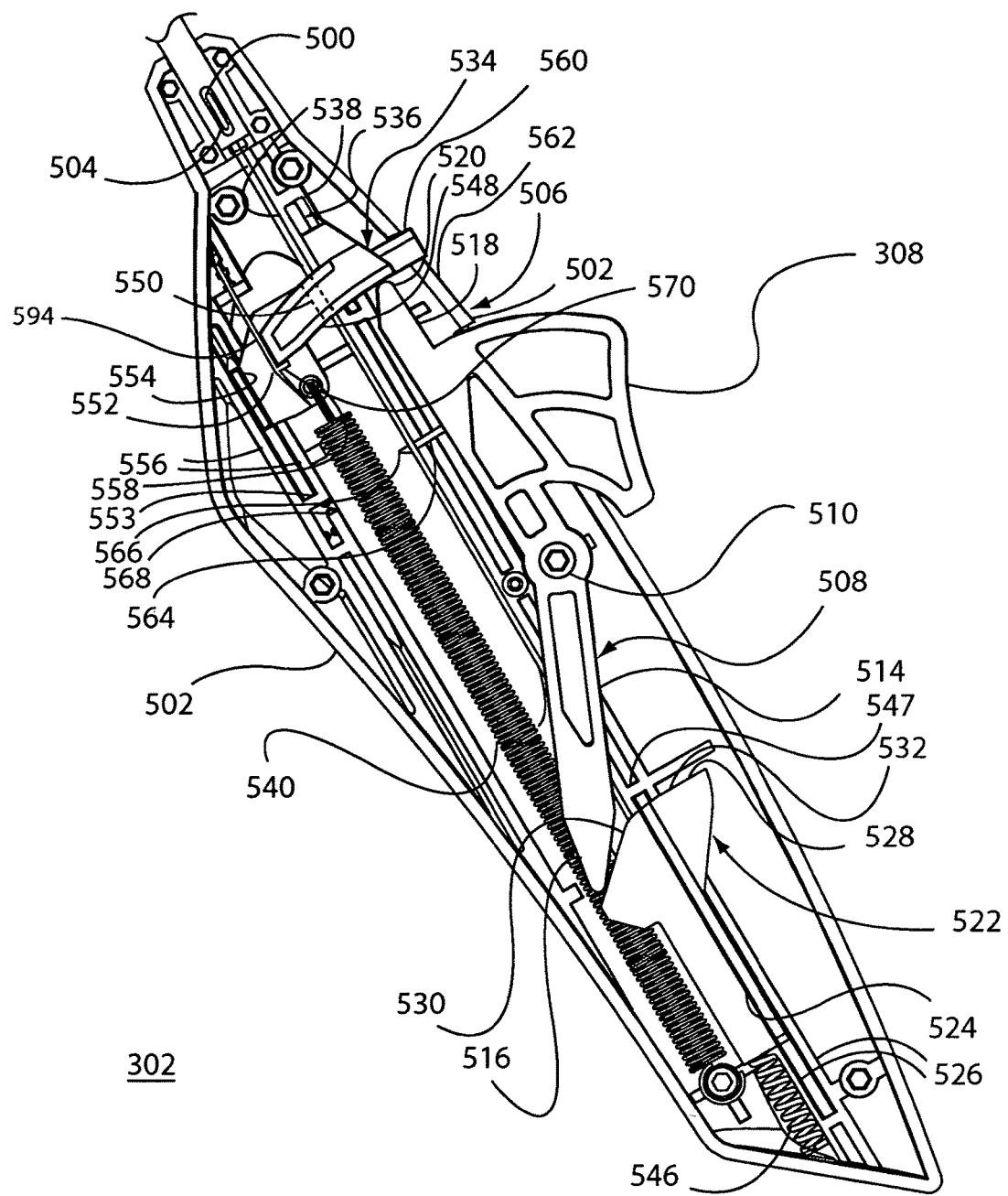
FIG. 70 is a side cross-section view of the handle of FIG. 55 in a first position.

The proximal end of the shaft 304 is connected to the handle 302. The handle 302 may be formed from two or more individual handle shell members 502 that are connected to one another. Alternately, the handle 302 may be constructed differently. The shaft 304 may be fixed to the handle 302 such that it does not substantially move relative to the handle 302. Referring also to FIG. 70, as one example, a member 500 extends from one handle shell member 502 into the hollow interior of the handle 302. That member 500 may connect at its other end to the other handle shell member 502. The proximal end of the shaft 304 includes a corresponding aperture 504, such that the member 500 fits within the aperture 504. The aperture 504 is substantially the same size as the cross-section of the member 500. When the shell members 502 are assembled, the member 500 engages the aperture 504 of the shaft 304 and holds the shaft 304 in place. Alternately, a member 500 extends from each handle shell member 502, and those members 500 both engage the aperture 504 of the shaft 304. As another example, ribs (not shown) may be defined in the inner surface of the handle, and a corresponding retainer (not shown) is defined at or near the proximal end of the shaft. The retainer is wider than the shaft 304, and has a selected thickness. The ribs are spaced apart from one another substantially the same distance as the thickness of the retainer. The ribs thus substantially prevent the shaft 304 from translating proximally or distally. The handle 302 may engage the retainer with a registration feature or other structure or mechanism to substantially prevent rotation of the shaft 304 about its longitudinal axis. Alternately, the handle 302 holds the shaft 304 in a different way.

The handle 302 has a substantially hollow interior. Where the shaft 304 includes a lumen, the lumen of the shaft 304 opens into the interior of the handle 302. The cables 480, 490 extend out of the lumen of the shaft 304 into the hollow interior of the handle 302. Alternately, the cables 480, 490 extend through the cable housing 306 directly into the handle 302, bypassing the shaft 304.

Referring to FIGS. 70 and 78, mechanisms within the handle 302 are utilized to actuate the tissue effector 38 via the cables 480, 490. Alternately, at least some of those mechanisms are separate from the handle 302. A single input to the anastomosis tool 300 via the trigger 308 actuates the anastomosis tool 300. Alternately, one or more additional inputs to the anastomosis tool 300 are required, such as actuation of a safety switch or depression of a second feature. The trigger 308 initially extends outward from the upper surface of the handle 302 through an aperture 506 in the handle 302. Alternately, the trigger 308 initially extends from a different surface of the handle 302. Alternately, the trigger 308 is initially flush with the surface of the handle 302, or otherwise configured. The handle 302 may be shaped ergonomically for ease of operation. For example, as shown in FIGS. 70 and 78, the handle 302 is curved and tapered slightly toward its proximal end, and substantially bilaterally symmetrical, such that the proximal end of the handle 302 can be gripped easily with either the left or the right hand. Alternately, the handle 302 may be ergonomically configured in a different way for ease of actuation by the user. The trigger 308 is positioned on the handle 302 such that it can be actuated conveniently by a user's thumb. Alternately, the trigger 308 could be placed on the underside of the handle 302 for actuation with the index finger of either hand. More than one finger may be used to actuate the trigger 308 and/or other mechanisms for actuating the anastomosis tool 300.

The trigger 308 is connected to a rocker 508. The trigger 308 may be formed into the rocker 508, or otherwise connected to it. The rocker 508 is located inside the handle 302. Alternately, the rocker 508 is located at least partly outside the handle 302. The rocker 508 is rotatably mounted to a rocker axle 510. The rocker axle 510 extends from one interior surface of the handle 302, and may extend to a different interior surface of the handle 302 to provide additional stiffness and/or stability to the rocker axle 510. Alternately, the rocker axle 510 may connect to the handle 302 in a different way.

Figure 71:
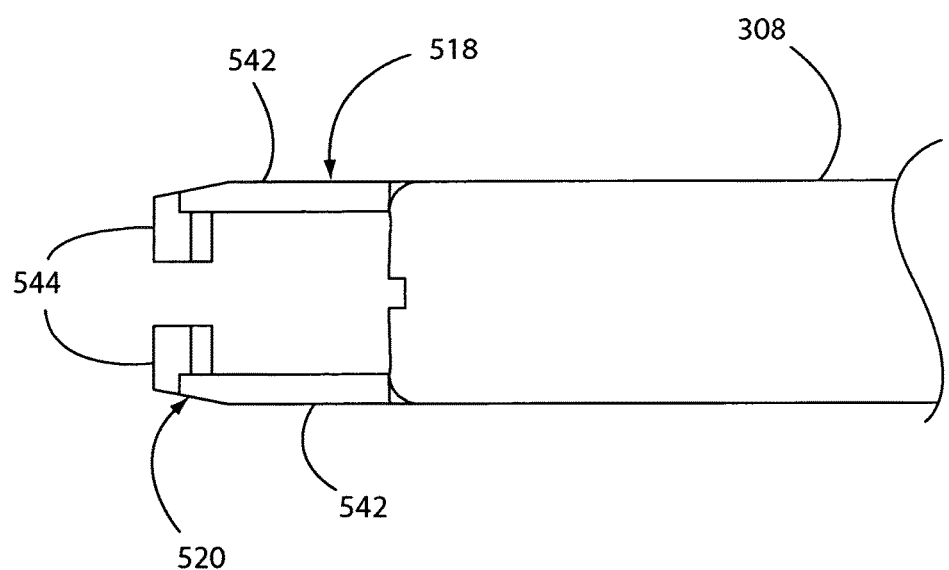
FIG. 71 is a top view of a portion of a rocker utilized in the handle of FIG. 55.

The rocker 508 includes a proximal arm 514 extending proximally to the rocker axle 510. The proximal arm 514 may be formed into the rocker 508, or otherwise connected to it. The proximal end 516 of the proximal arm 514 may be tapered to a curved or rounded surface. Alternately, the proximal end 516 of the proximal arm 514 is shaped differently. Alternately, the entire proximal arm 514 is tapered. The rocker axle 510 is located proximal to the trigger 308. As a result, depression of the trigger 308 causes rotation of the rocker 508 such that the proximal end 516 of the proximal arm 514 moves upward. Alternately, the trigger 308 and the rocker axle 510 are positioned differently relative to one another. The rocker 508 also includes a distal arm 518 extending distal to the trigger 308, where the distal arm 518 has a distal end 520. The distal arm 518 may be formed into the rocker 508, or otherwise connected to it. Referring also to FIG. 71, at least a portion of the distal arm 518 may be bifurcated into two or more spaced-apart members 542. A post 544 may be located at the distal end of each member 542. At least one post 544 substantially may take the shape of a cylindrical or rectangular solid. Each post 544 is angled relative to the corresponding member 542, protruding at least partly inward. This angle may be substantially ninety degrees, or any other angle. Alternately, at least one post 544 extends outward from the corresponding member. The posts 544 are spaced apart from one another by a distance that is less than the distance separating the spaced-apart members 542. Alternately, at least one post 544 is located at a position on the corresponding member 542 other than its distal end. As one example, at least one post 544 may be positioned a short distance proximal to the distal end of the corresponding member 542.

Because the rocker axle 510 is located proximal to the trigger 308, depression of the trigger 308 causes the distal end 520 of the distal arm 518 to move downward. Alternately, the arms 514, 518 of the rocker 508 are configured to move in another manner when the trigger 308 is depressed. Alternately, the rocker 508 may be shaped or configured differently than described above.

A proximal slider 522 is also included within the handle 302. The proximal slider 522 includes at least one flange 524 extending laterally from at least one side thereof. Advantageously, a flange 524 extends from each side of the proximal slider 522 for stability. Additional flanges 524 may be provided, if desired. Ribs 526 are molded, formed, connected or otherwise attached to the inner surface of the handle 302. Two ribs 526 are spaced apart from one another a distance substantially equal to the thickness of the corresponding flange 524, such that each flange 524 is configured to slide therebetween. Each pair of ribs 526 substantially constrains the motion of the corresponding flange 524. Where the ribs 526 are substantially linear, and ribs 526 and corresponding flanges 524 are utilized on opposite sides of the proximal slider 522, the ribs 526 substantially linearly constrain the motion of the corresponding flange 524. A spring 546 is connected at one end to the handle 302, and is connected to or engages the proximal slider 522. The spring 546 is in compression, and thereby biases the proximal slider 522 distally. A stop 547 may be connected to or defined in the inner surface of one or more of the handle shell members 502, where the stop or stops 547 are located distal to the proximal slider 522. The stop or stops 547 act to restrain the distal motion of the proximal slider 522, thereby defining a position that is the most distal the proximal slider 522 can travel. Alternately, a different or additional mechanism, structure or method may be used to bias the proximal slider 522 distally. Alternately, the spring 546 is initially neither in tension nor compression, but is compressed by the rocker 508 during at least a portion of its travel.

The spring 546 stores energy within itself when it is in tension. Alternately, an energy storage device could be used in lieu of the spring 546. As one example, the energy storage device is a reservoir or cylinder of pressurized gas. Valves, tubing and/or other structure may be used to route the pressurized gas to desired locations in the handle 302 such that the energy stored in the gas is used to bias the proximal slider 522 distally, and/or to perform other actuation functions within the handle 302 and/or the tool 300. The gas may be carbon dioxide, nitrogen, a different gas, air, or a combination of gases. As another example, a cylinder or source of vacuum may be used as an energy storage device. Valves, tubing and/or other structure may be used to route the vacuum to desired locations in the handle 302 such that the vacuum can be used to bias the proximal slider 522 distally, and/or to perform other actuation functions within the handle 302 and/or the tool 300. That is, compressed gas may be used for controlling the operation of the tool 300 instead of or in addition to providing energy storage. As another example, a battery may be used as an energy storage device. Wiring and actuators such as solenoids or motors may be provided within the handle 302 such that the stored electrical energy in the battery is used to bias or hold the proximal slider 522 distally, and/or to perform other actuation functions within the handle 302 and/or the tool 300. That is, electromagnetic energy may be used for controlling the operation of the tool 300 instead of or in addition to providing energy storage. Where such an alternate energy storage device is provided, the trigger 308 may be configured differently, such that actuation of the anastomosis tool 300 may be performed simply by contacting the trigger 308 with a finger, or moving the trigger 308 through a more limited range of motion. Alternately, the trigger 308 may be omitted altogether, and the anastomosis tool 300 may be actuated remotely by a computer, dedicated control station, handheld computing device, or other device.

A contact feature 528 is defined on the distal surface of the proximal slider 522. Alternately, the contact feature 528 is a separate element connected to the proximal slider 522. The contact feature 528 is configured to engage the proximal end 516 of the proximal arm 514 at or after the time the trigger 308 is depressed, as described in greater detail below. The contact feature 528 is angled proximally and downward along a lower portion 530 thereof, and is substantially vertical along an upper portion 532 thereof. Alternately, the contact feature 528 is shaped and/or angled differently.

The first cable or cables 480 are connected to the proximal slider 522 in any appropriate way. As an example, at least one aperture or port (not shown) may be formed in the proximal slider 522, and at least one cable 480 is inserted into at least one aperture and secured thereto. As other examples, an end of the cable or cables 480 may be wound around all of or a portion of, crimped to, welded to, or secured by adhesive to the proximal slider 522. The proximal arm 514 of the rocker 508 may be bifurcated to allow the first cable or cables 480 to extend substantially along the longitudinal centerline of the handle 302 and between the bifurcations substantially without interference. Similarly, the lower portion 530 of the contact feature 528 may be bifurcated as well. Where both the proximal arm 514 and the contact feature 528 are bifurcated, the two are aligned such that they contact one another during at least a portion of the travel of the rocker 508.

A distal slider 534 is also included within the handle 302. The distal slider 534 includes a flange 536 extending outward from at least one side thereof. Advantageously, a flange 536 extends from each side of the distal slider 534 for stability. Additional flanges 536 may be provided, if desired. Ribs 538 are molded, formed, connected or otherwise attached to the inner surface of the handle 302. Two ribs 538 are spaced apart from one another a distance substantially equal to the thickness of the corresponding flange 536, such that each flange 536 is configured to slide therebetween. Each pair of ribs 538 substantially constrains the motion of the corresponding flange 536. Where the ribs 538 are substantially linear, and ribs 538 and corresponding flanges 536 are utilized on opposite sides of the distal slider 534, the ribs 538 substantially linearly constrain the motion of the corresponding flange 524.

A contact surface 548 is defined on at least a portion of the proximal surface of the distal slider 534. The contact surface 548 may be curved or angled. As one example, the contact surface 548 has a concave curvature. Other shapes or configurations of the contact surface 548 may be utilized. Alternately, the contact surface 548 is located on a portion of the distal slider 534 other than its proximal surface. The distal slider 534 may include a passage 550 through it to allow the cables 480, 490 to pass therethrough. Alternately, the passage 550 is not provided in the distal slider 534, and the distal slider 534 is bifurcated or otherwise shaped to allow the cables 480, 490 to pass through it. Alternately, the cables 480, 490 are routed through the handle in such a way as to bypass the distal slider 534 altogether.

The distal slider 534 may include a lower guide 552. The lower guide 552 extends downward from the remainder of the distal slider 534, and may extend proximal to the contact surface 548. Further, the lower guide 552 may be thinner than the remainder of the distal slider 534. Alternately, the lower guide 552 is not included in the distal slider 534, or may be configured differently relative to the remainder of the distal slider 534. Optionally, the lower guide 552 may include a flange 554 extending outward from at least one side thereof. Advantageously, a flange 554 extends from each side of the lower guide 552 for stability. Additional flanges 554 may be provided, if desired. These flanges 554 provide additional stability to the distal slider 534. Ribs 556 are molded, formed, connected or otherwise attached to the inner surface of the handle 302. Two ribs 556 are spaced apart from one another a distance substantially equal to the thickness of the corresponding flange 554, such that each flange 554 is configured to slide therebetween. Each pair of ribs 556 substantially constrains the motion of the corresponding flange 554. Where the ribs 556 are substantially linear, and ribs 556 and corresponding flanges 554 are utilized on opposite sides of the distal slider 534, the ribs 556 substantially linearly constrain the motion of the corresponding flange 554.

A spring 540 is connected at one end to the distal slider 534 and at the other end to the handle 302. An aperture 558 may be provided in the lower guide 552, or in another part of the distal slider 534. One end of the spring 540 includes a hook or similar structure, which is received into and held by the aperture 558. Alternately, the spring 540 is connected to the distal slider 534 in a different way. The spring 540 is in tension, and thereby biases the distal slider 534 proximally. Alternately, a different or additional mechanism, structure or method may be used to bias the distal slider 534 proximally.

Referring also to FIG. 70, a holder 594 is connected to the inner surface of the handle 302. This connection may be accomplished in any appropriate manner.

The holder 594 is substantially restrained against longitudinal motion by its engagement with the shell members 502. Contact between the distal slider 534 and the rocker 508 prevents the distal slider 534 from substantially moving proximally. This contact occurs between the contact surface 548 of the distal slider 534 and the distal tip 520 of the distal arm 518 of the rocker 508. Alternately, this contact occurs between other or additional components of the distal slider 534 and/or the rocker 508.

The spring 540 stores energy within itself when it is in tension. Alternately, an energy storage device such as a reservoir or container of pressurized gas, a battery, or other energy storage device could be used in lieu of the spring 540. Where a reservoir of pressurized gas is utilized, valves, tubing and other structure may be used to route the pressurized gas to desired locations in the handle 302 such that the energy stored in the gas is used to bias the distal slider 534 proximally, and/or to perform other actuation functions within the handle 302 and/or the tool 300. Similarly, where a battery is utilized, wiring and actuators such as solenoids or motors may be provided within the handle 302 such that the stored electrical energy in the battery is used to bias or hold the distal slider 534 proximally, and/or to perform other actuation functions within the handle 302 and/or the tool 300. Where such an alternate energy storage device is provided, the trigger 308 may be configured differently, such that actuation of the anastomosis tool 300 may be performed simply by contacting the trigger 308 with a finger, or moving the trigger 308 through a more limited range of motion. Alternately, the trigger 308 may be omitted altogether, and the anastomosis tool 300 may be actuated remotely by a computer, dedicated control station, handheld computing device, or other device.

The second cable 490 is connected to the distal slider 534 in any appropriate way. As an example, at least one aperture or port (not shown) may be formed in the distal slider 534, and at least one cable 480 is inserted into at least one aperture and secured thereto. As other examples, an end of the cable or cables 480 may be wound around all of or a portion of, crimped to, welded to, or secured by adhesive to the distal slider 534. The second cable 490 may have an amount of slack in it when the distal slider 534 is in the first, predeployment position shown in FIG. 70. The amount of slack, if any, is related to the distance traveled by the distal slider 534 during actuation, as described in greater detail below.

Optionally, the distal slider 534 includes a verification stub 560. The verification stub 560 extends substantially upward from the upper end of the distal slider 534. Alternately, the verification stub 560 extends from a different portion of the distal slider 534, or in a different direction. The verification stub 560 may extend into or through a slot 562 through the handle 302. Because it is connected to the distal slider 534, the verification stub 560 moves along the slot 562 in the handle 302 when the distal slider 534 moves during operation, as described below. As a result, the position of the verification stub 560 may be used to confirm visually whether a particular anastomosis tool 300 has been actuated or not. That is, the verification stub 560 may be located in a first position before the anastomosis tool 300 is actuated, and in a second position after the anastomosis tool 300 is actuated, such that the user can determine whether the anastomosis tool 300 has been actuated by viewing the position of the verification stub 560.

Optionally, the rocker 508 includes a ratchet 564 extending substantially downward from a location distal to the rocker axle 510. Alternately, the ratchet 564 extends in a different direction. The ratchet 564 includes a member 566 at its lower end extending substantially transverse to the remainder of the ratchet 564. Alternately, the member 566 extends in a different direction. Alternately, the member 566 is a notch or other element defined in the ratchet 564. The ratchet 564 moves in conjunction with the rocker 508. Thus, when the trigger 308 is depressed and the distal end of the rocker 508 moves downward, the ratchet 564 moves downward as well. A pawl feature 568 is configured to engage the member 566 of the ratchet 564 after the ratchet 564 has moved downward a particular distance, allowing the ratchet 564 to continue to move downward after engagement, but preventing the ratchet 564 from moving back upward past the pawl feature 568 after engagement.

Alternately, the rocker 508, sliders 522, 534, and/or other mechanisms in the handle are not used, and a different mechanism or mechanisms are used to actuate the tissue effector 400 and complete the anastomosis. For example, a fluid logic mechanism may be used, where a container of gas within the handle or a connection to a tank outside the handle provides gas under pressure to a switching assembly or other mechanism. The switching assembly utilizes and/or directs the pressure of the gas to successively actuate the components of the tissue effector 400. Vacuum or liquid may be used instead of gas, if desired. As another example, the handle 302 may include an electromechanical assembly under analog or digital control, such that actuation of the trigger 308 or other component causes actuation of the tissue effector.

The operation of the anastomosis tool 300 will now be described. Referring to FIGS. 59 and 74, an end of the graft vessel 404 is incised substantially in the longitudinal direction to form flaps 404 therein. At least one incision may be made in a different direction. Advantageously, two incisions are made to create two flaps 404 of substantially the same size. However, the flaps 404 may be of different sizes. Further, more than two flaps 404 may be created with more than two incisions. Alternately, a single flap 404 is made with a single incision. The graft vessel 404 is loaded onto the staple holder 38 as described above, such that each flap 408 is held between a graft clip 412 in the closed position and a flap receiving surface 406, and the graft vessel 404 extends between the arms 402 of the staple holder 38. Referring also to FIG. 70, the anastomosis tool 300 is initially in a pre-deployment configuration. In this configuration, the distal arm 518 of the rocker 508 is at an uppermost position, the trigger 308 correspondingly extends outward from the handle 302 to its greatest extent, and the proximal arm 514 of the rocker 508 is at a lowermost position. The distal end 520 of the distal arm 518 of the rocker 508 may engage the contact surface 548 of the distal slider 534 at or near the uppermost end of the contact surface 548. This contact may be between the posts 544 of the distal arm 518 and the contact surface 548, and/or between another portion of the distal arm 518 and the contact surface 548. The stops 596 of the holder 594 hold the distal slider 534 substantially in place against the proximal bias exerted by the spring 540. Alternately, where the holder 594 is not used, contact between the rigid distal arm 518 and the contact surface 548 holds the distal slider 534 substantially in place against the proximal bias exerted by the spring 540. In the pre-deployment configuration, the proximal end 516 of the proximal arm 514 may be spaced apart from the lower portion 530 of the proximal slider 522, or may be in contact with the lower portion 530 of the proximal slider 522. The proximal slider 522 is biased distally to its most distal possible position. Alternately, the proximal slider 522 is positioned differently in the pre-deployment configuration. Alternately, the rocker 508 and/or the trigger 308 may be in a different position in the pre-deployment configuration, particularly where the rocker 508 and/or trigger 308 are shaped or configured differently than shown in FIG. 70. If so, the rocker 508 may engage the proximal slider 522 and/or the distal slider 534 in a different manner than described above.

Figure 77:
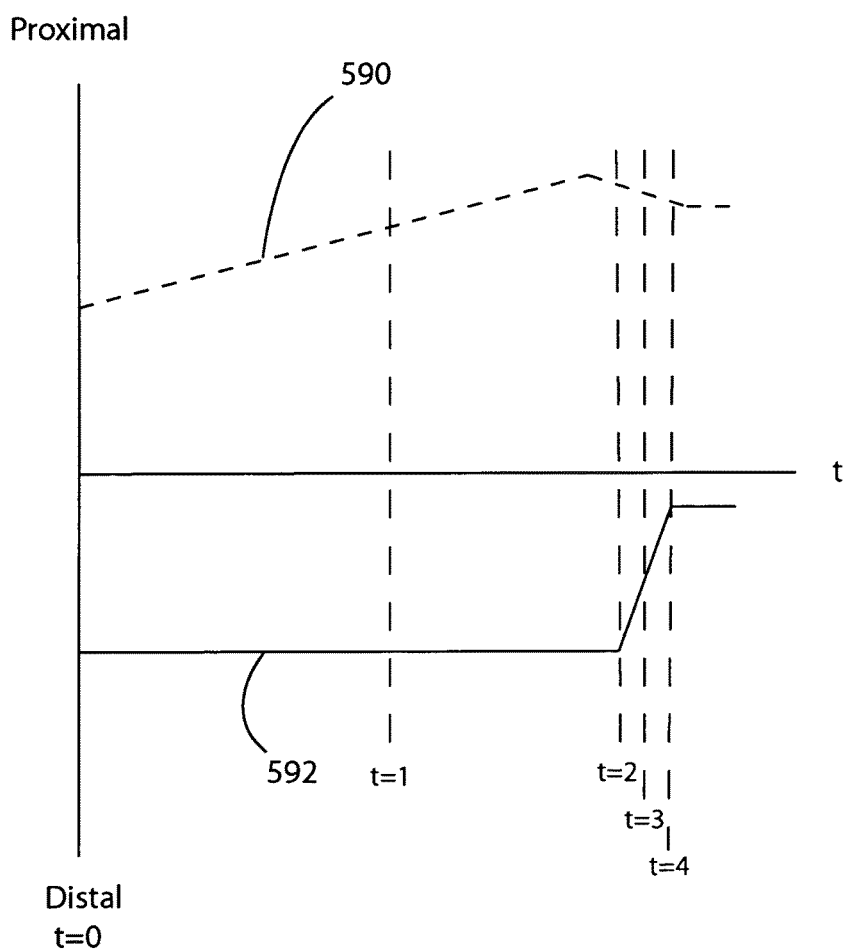
FIG. 77 is a graph qualitatively illustrating the positions of the distal slider and the proximal slider of the handle over time, with regard to an arbitrary point between them.

Referring also to FIG. 77, when the handle 302 is in the pre-deployment configuration, the time is t=0. The position 590 of the proximal slider 522 is at an initial position, and the position 592 of the distal slider 534 is also at an initial position. The positions 590, 592 of the sliders 522, 534 on the graph of FIG. 77 are qualitative, and are shown with respect to an arbitrary point selected between them. That is, the graph of FIG. 77 illustrates an exemplary set of motions of the sliders 522, 534 over time.

The first cable or cables 480 are connected to the proximal slider 522 and the second cable 490 is connected to the distal slider 534, as described above. In the pre-deployment configuration, both cables 480, 490 include some slack, such that a small initial motion of the trigger 308 takes up the slack and causes the cables 480, 490 to become tensioned. In this way, small motions of the trigger 308 before deployment is intended do not begin the actuation of the anastomosis tool 300. Alternately, one or more of the cables 480, 490 are tensioned in the pre-deployment configuration.

Figure 72:
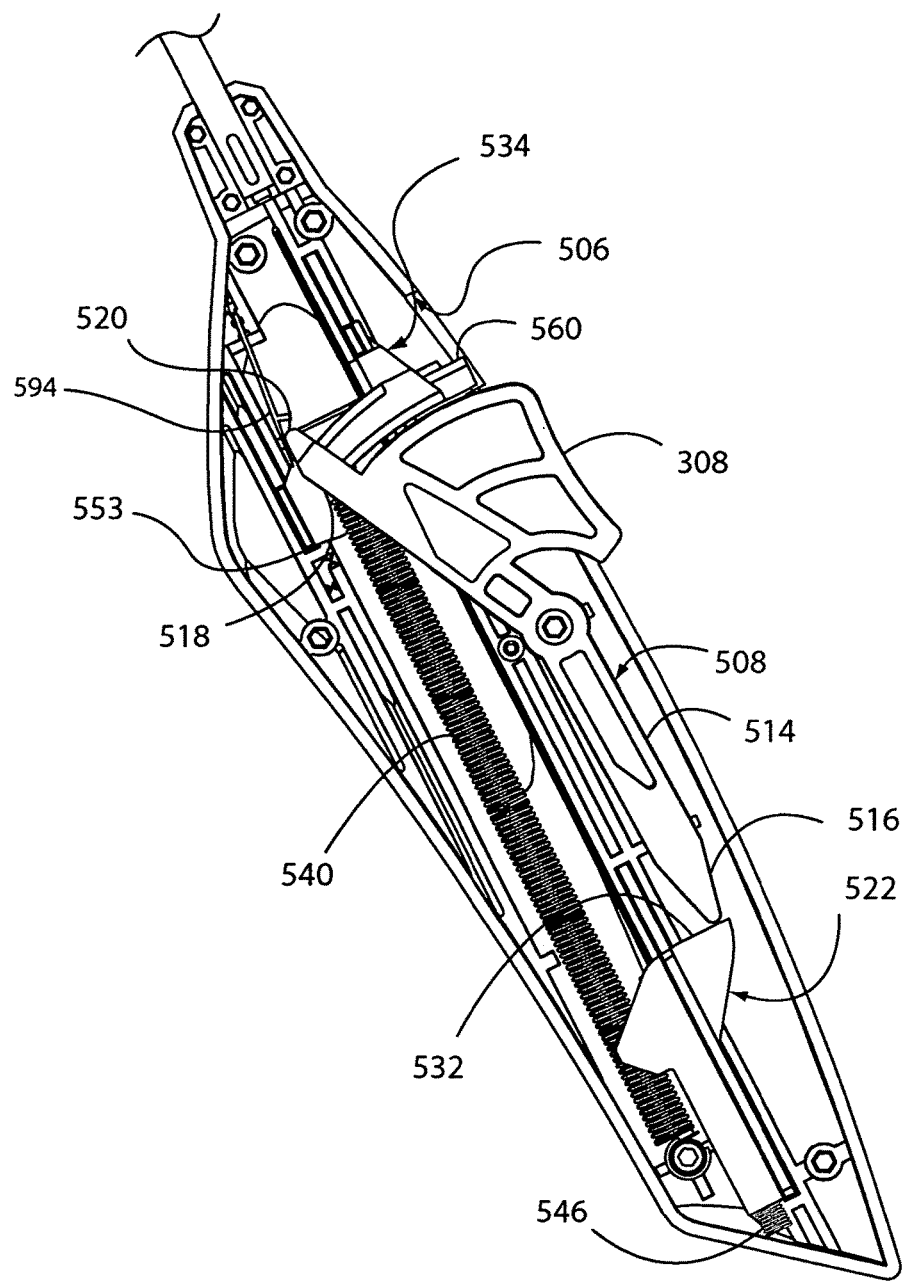
FIG. 72 is a side cross-section view of the handle of FIG. 55 in a second position.

The second cable 490 is also connected to the sled 482 in the tissue effector 400, as described above. Referring also to FIGS. 64 and 68-69, in the pre-deployment configuration the sled 482 is positioned such that each ramp element 446 is located within the corresponding passage 440 in the corresponding arm 402, proximal to the connector bays 448. Similarly, in the pre-deployment configuration the sled 482 is positioned such that each vein knife 432 is located proximal to the vein flap 408 held between the graft clip 412 and the corresponding flap receiving surface 406. Alternately, the sled 482 is positioned differently in the pre-deployment configuration. For example, each ramp element 446 may be positioned initially in a location distal to the connector bays 448. Referring also to FIG. 72, each flap 408 is held between a graft clip 412 and a flap receiving surface 406 as described above, such that the graft vessel 404 extends between the arms 402 of the tissue effector 400. The flaps 408 are held on the undersides of the arms 402. Each flap 408 is held by the corresponding graft clip 412 such that a portion of the flap 408 at its root 405, which is the portion of the flap 408 at or in proximity to its intersection with the tubular portion of the graft vessel 404, is exposed. The root 405 of each flap 408 is configured to contact the outer surface of the target vessel, as described in greater detail below.

Optionally, the orientation of the tissue effector 400 may be changed relative to the handle 302. Thus, the tissue effector 400 can be oriented relative to the target vessel such that the anvil arm 14 is aligned with it, and the handle 302 can be placed in a convenient position for the user. To re-orient the tissue effector 400, the user depresses the buttons 278, disengaging the teeth 284 of the cog 282 from the detents 310 of the receiving opening 309. The tissue effector 400 is then rotated to the desired orientation. The buttons 278 are then released, allowing the teeth 284 of the cog 282 to engage once again the detents 310 of the receiving opening 309. The cog 282 is thus held securely in place in its new orientation.

Figure 75:
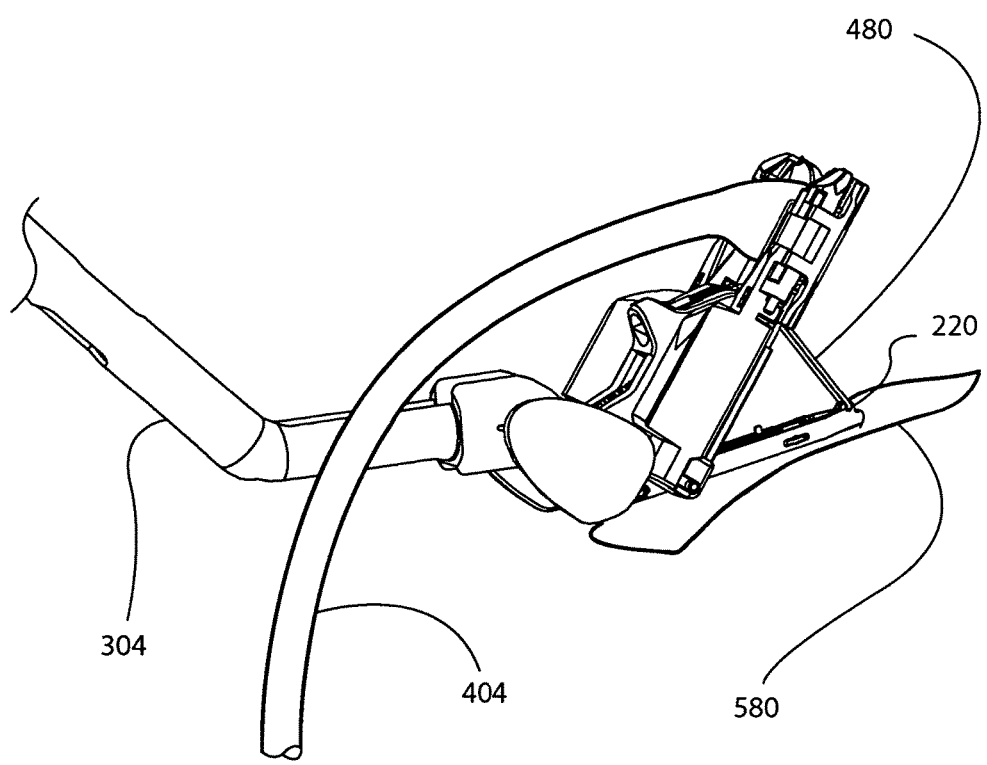
FIG. 75 is a perspective view of the tissue effector of FIG. 74, where the anvil of the tissue effector has been inserted into the lumen of a target vessel.

Referring to FIGS. 34 and 74, in the pre-deployment configuration, the distal end of the anvil arm 14 is spaced apart from the staple holder 38. Referring also to FIG. 75, the anvil arm 14 is inserted through the wall of the target vessel 580. The target vessel 580 may be a coronary artery, if the anastomosis tool 300 is used in the course of a CABG procedure, or any other appropriate bodily vessel or structure. Advantageously, the anvil arm 14 has a cross-section small enough to allow it to enter the target vessel 580 easily and to result in minimal or no leakage from the target vessel after the anvil arm 14 is removed. The distal tip of the anvil arm 14 may be sharp such that the anvil arm 14 itself penetrates the wall of the target vessel 580, resulting in an opening in the wall of the target vessel 580 substantially the same size as the cross-section of the anvil arm 14. Alternately, a sharp retractable projection, such as but not limited to the blade 78 of FIGS. 13-14 or the blade 84 of FIGS. 15-16, is provided at the distal end of the anvil arm 14. The retractable projection is extended to allow the distal end of the anvil arm 14 to penetrate the wall of the target vessel 580, then retracted into the anvil arm 14. The retractable projection may be a wire, a blade, a substantially conical member, a screw or a screw-tipped rod, or any other sharp structure or mechanism capable of penetrating the wall of the target vessel 580. Such a retractable projection alternately may be as described in U.S. patent application Ser. No. 10/134,081, which is herein incorporated by reference in its entirety. Alternately, a separate mechanism or structure is used to penetrate the wall of the target vessel 580, and the anvil arm 14 is later inserted through that penetration. Alternately, the cutter 200 includes a sharp point at its distal end, where that sharp point extends out of the distal end of the anvil arm 14 to puncture the wall of the target vessel 580. If so, the cutter 200 may be actuated in a direction the reverse of that described below.

Referring also to FIGS. 36 and 75, after insertion, the distal end of the anvil arm 14 enters the lumen of the target vessel 580. The anvil arm 14 is advanced into the target vessel 580 until a tissue stop 220 on the anvil arm 14 encounters the edge of the penetration in the wall of the target vessel 580. The tissue stop 220 is substantially flat and/or blunt, and extends upward or in another direction relative to the anvil arm 14 to increase the height and/or width of the anvil arm 14. The tissue stop 220 increases the cross-section of the anvil arm 14 such that the anvil arm 14 cannot easily move further into the penetration in the wall of the target vessel 580 after the tissue stop 220 encounters the outer wall of the target vessel 580. Because the tissue stop 220 is blunt, it does not penetrate the wall of the target vessel 580 or act to expand the size of the existing penetration. Thus, the distance between the distal end of the anvil arm 14 and the tissue stop 220 substantially determines how much of the anvil arm 14 is allowed into the lumen of the target vessel 580.

Optionally, the distal end of the anvil arm 14 is stabilized after insertion into the target vessel 580. This stabilization may be performed by, for example, extending pins (not shown) from the staple holder 38 to the anvil arm 14, where the pins act to hold the distal end of the anvil arm 14 substantially in place. The pins may be sized and shaped to fit into depressions, slots or other features on the anvil arm 14. In this way, potential deflection of the distal end of the anvil arm 14 may be further reduced without the need for increasing the stiffness of the anvil arm 14. After the connectors 464 have been deployed, the pins are retracted or otherwise moved away from the anvil arm 14, freeing it. Different or additional mechanisms, structures or methods may be used to stabilize the anvil arm 14. Optionally, a different part of the anvil arm 14 is stabilized in addition to or instead of the distal end of the anvil arm 14.

Next, referring also to FIGS. 44 and 70, an operator depresses the trigger 308 of the anastomosis tool 300. As a result, the rocker 508 begins to rotate about the rocker axle 510, such that the distal arm 518 moves downward and the proximal arm 514 of the rocker 508 moves upward. As the trigger 308 is depressed, the distal end 520 of the distal arm 518 moves downward. The stops 596 of the holder 594 continue to hold the distal slider 534 substantially in place against the proximal bias exerted by the spring 540. Thus, the distal slider 534 does not substantially move as the trigger 308 is initially depressed. The contact surface 548 of the distal slider 534 is curved to substantially match the travel of the distal end 520 of the distal arm 518. That is, the radius of curvature of the contact surface 548 relative to the rocker axle 510 is substantially the same as the path of motion of the distal end 520 of the distal arm 518 as the rocker 508 rotates, and thus does not substantially interfere with the motion of the distal arm 518. If the holder 594 is not used, the distal end 520 of the distal arm 518 holds the distal slider 534 in substantially the same position as the distal arm 518 moves relative to the contact surface 548, due to the match between the curvature of the contact surface 548 and the motion of the distal end 520 of the distal arm 518. Alternately, the contact surface 548 is configured differently. Further, the distal slider 534 may be configured to move as the trigger 308 is initially depressed, if desired.

The proximal end 516 of the proximal arm 514 moves upward as the trigger 308 is depressed, and contacts the lower portion 530 of the contact feature 528 of the proximal slider 522 if it is not initially in contact with the proximal slider 522. As the proximal end 516 of the proximal arm 514 continues to move upward, it continues to engage the lower portion 530 of the contact feature 528 of the proximal slider 522. The lower portion 530 of the contact feature 528 is shaped such that a component of force exerted by the proximal end 516 of the proximal arm 514 on that lower surface 530 is converted into a substantially translational force acting on the proximal slider 522 to urge it proximally. As one example, the lower portion 530 of the contact feature 528 is angled proximally and downward. Further, the ribs 526 and corresponding flanges 524 of the proximal slider 522 substantially linearly constrain the motion of the proximal slider. The angle of the lower surface 530 relative to the arcuate motion of the proximal end 516 of the proximal arm 514 results in the conversion of the substantially arcuate motion of the proximal end 516 of the proximal arm 514 to substantially linear motion of the proximal slider 522.

Thus, the upward motion of the rocker 508 against the lower portion 530 of the contact feature 528 of the proximal slider 522 urges the proximal slider 522 in the proximal direction, against the bias of the spring 546 connected to the proximal slider 522 and the handle 302. Referring also to FIG. 77, this is time t=1, the proximal slider 522 has moved proximally from time t=0, and the distal slider 534 has remained in substantially the same position it occupied at time t=0. As the proximal slider 522 moves proximally, it takes up slack in the first cable or cables 480 connected thereto, if slack is present. The first cable or cables 480 are fixed to the anvil 10. Because the anvil 10 is in turn fixed relative to the shaft 304, the proximal motion of the first cable or cables 480 removes slack from, then tensions, the first cable or cables 480. The first cable or cables 480 pass through at least a portion of the cable housing 306. As described above, the cable housing 306 curves between the shaft 304 and the tissue effector 400. The tension in the first cable or cables 480 causes the cable housing 306 to move. That is, the tension in the first cable or cables 480 acts upon the flexible cable housing 306, causing its curvature to decrease. Although the cable housing 306 is at least partially flexible, the cable housing 306 possesses stiffness longitudinally. Thus, as the curvature of the cable housing 306 decreases, the distal end of the cable housing 306 moves distally. Referring also to FIG. 58, the staple holder 38 is biased away from the anvil 10 by a biasing element 475, which tends to move the tissue effector 400 to an open position. The biasing element 475 may be a coil spring, leaf spring, or any other structure or mechanism capable of applying a biasing force. When the tension in the first cable or cables 480 causes the distal end of the cable housing 306 to move distally, the distal end of the cable housing 306 exerts a force on the anvil 10 that overcomes the bias of the biasing element 475, causing the anvil 10 to rotate about a pivot point such as the pin 226 to a standby position. In this way, the anvil arm 14 remains substantially stationary within the target vessel 580, while the staple holder 38 rotates. Alternately, the staple holder 38 and anvil 10 may be actuated to move between the position shown in FIG. 34 and the position shown in FIG. 44 by any structure, mechanism or method.

Alternately, a second cable housing (not shown) is provided. If so, the first cable or cables 480 may extend through the cable housing 306 as described above, and the second cable or cables 490 may extend through the second cable housing. In this way, the forces exerted along the first cable or cables 480 and cable housing 306 are substantially isolated from the forces acting along the second cable or cables 490 and the second cable housing.

Referring also to FIGS. 29-31, 44 and 76, as the staple holder 38 and anvil 10 move closer together, the staple holder 38 holds a root 405 of each flap 408 against or in proximity to the outer surface of the target vessel. For clarity, the flaps and graft vessel are not shown in FIG. 44. That is, the roots 405 of the flaps 408 are apposed to the outer wall of the target vessel 580. As a result, a portion of the intimal layer of the graft vessel 404 at the root 405 of each flap 408 is placed against the outer wall of the target vessel 580. The flaps 408 are held by the staple holder 38 in a substantially fixed position relative to the surface of the target vessel 580, such that the end of the graft vessel 404 is substantially immobile relative to the wall of the target vessel 580. Thus, the position of the end of the graft vessel 404 relative to the wall of the target vessel 580 remains substantially unchanged throughout the duration of the anastomosis procedure. Further, after the anvil arm 14 has been inserted into the lumen of the target vessel 580, the contact surface 206 of the anvil arm 14 is substantially in contact with the inner surface of the wall of the target vessel 580. The perimeter of the end of the graft vessel 404 defines a closed area on the wall of the target vessel. The location of a connection made between the end of the graft vessel 404 and the wall of the target vessel is substantially registered with an opening made within the closed area in the wall of the target vessel, regardless of the order in which the connection and the opening are made. Further, the position of the end of the graft vessel 404 relative to the wall of the target vessel 580 substantially maintains position registration throughout the duration of the anastomosis procedure relative to the opening in the wall of the target vessel through which the anvil arm 14 is inserted.

As the staple holder 38 and anvil 10 move together, the engagement member 216 engages the receiver 218. As described above, the receiver 218 is defined in the sled 482. However, the receiver 218 may be a separate component from the sled 482. Further, if the optional safety feature 210 is utilized, the relative motion of the staple holder 38 and the anvil 10 causes the staple holder 38 to contact the safety feature 210 and urge it downward against its upward bias. Consequently, the tip 212 of the safety feature 210 is moved downward out of engagement with the safety recess 214 of the cutter 200. Alternately, another structure or mechanism is configured to engage the safety feature 210 when the staple holder 38 and anvil 10 are moved together, so as to urge the tip 212 out of the safety recess 214. Thus, in the standby position, the cutter 200 is freed for translation along the channel 246.

Optionally, an interface structure 238 may be connected to or formed into the staple holder 38. The interface structure 238 engages the anvil 10 or a component associated with the anvil 10 as the staple holder 38 and the anvil 10 move to the standby position, such as by snapping onto a corresponding feature (not shown) on the anvil 10. By doing so, the interface structure 238 holds the staple holder 38 substantially fixed relative to the anvil 10, in order to maintain registration between the target vessel, the graft vessel, the anvil 10 and the staple holder 38. The interface structure 238 may be a tab, rail, bump, or any other feature that is capable of engaging a corresponding feature and holding the staple holder 38 substantially fixed relative to the anvil 10. Alternately, the interface structure 238 is formed into or connected to the anvil 10 and engages a corresponding feature on the staple holder 38.

Referring also to FIG. 70, the user continues to depress the trigger 308. As a result, the rocker 508 continues to rotate about the rocker axle 510 such that the distal end 520 of the distal arm 518 continues to move downward, and the proximal end 516 of the proximal arm 514 continues to move upward. As the proximal end 516 of the proximal arm 514 continues to move upward, its contact with the lower portion 530 of the contact feature 528 of the proximal slider 522 continues to urge the proximal slider 522 proximally. When the proximal end 516 of the proximal arm 514 has reached a position at or near the intersection between the two portions 530, 532 of the contact feature 528, the proximal slider 522 has moved substantially as far proximally as it will move during actuation of the anastomosis tool 300. Further, when the proximal end 516 of the proximal arm 514 has reached that position, the staple holder 38 and the anvil arm 14 are still in the standby position. Referring also to FIG. 77, this is time t=2, at which the proximal slider 522 has moved proximally from its position at time t=1, and has reached its most proximal position. The distal slider 534 is in substantially the same position that it was in at time t=1.

The user continues to depress the trigger 308. As the proximal end 516 of the proximal arm 514 continues to move upward, it moves past the intersection between the two portions 530, 532 of the contact feature 528, thereby contacting the upper portion 532 of the contact feature 528. The upper portion 532 of the contact feature 528 provides substantially no resistance to the continued rotation of the rocker 508, because it is substantially vertical or angled in a proximal direction as it extends upward. The proximal end 516 of the proximal arm 514 thus moves upward rapidly. Alternately, the speed of the motion of the proximal end 516 of the proximal arm 514 is controlled to be the same as or slower than its speed while it contacts the lower portion 530 of the contact feature 528. During the upward motion of the proximal end 516 of the proximal arm 514, the proximal slider 522 may move distally at least slightly due to the arcuate motion of the proximal end 516 of the proximal arm 514 relative to the non-arcuate upper portion 532 of the contact feature 528.

As the proximal end 516 of the proximal arm 514 moves upward along the upper portion 532 of the contact feature 528, the distal end 520 of the distal arm 518 continues to move downward along the contact surface 548 of the distal slider 534. As described above, the posts 544 at the distal end 520 of the distal arm 518 are spaced apart from one another, such that a gap is present between them. The distal arm 518 may contact the contact surface 548 via the posts 544 during at least a portion of its travel. As the distal end 520 of the distal arm 518 moves downward, the posts 544 reach the bottom edge 570 of the contact surface 548. The rocker 508, the proximal slider, and the distal slider 534 are positioned relative to one another and shaped such that the posts 544 reach the bottom edge 570 of the contact surface 548 at substantially the same time that the proximal end 516 of the proximal arm 514 reaches the intersection between the two portions 530, 532 of the contact feature 528 of the proximal slider 522.

When the posts 544 reach the bottom edge 570 of the contact surface 548, they contact the holder 594. As the distal end 520 of the distal arm 518 continues to move downward, the distal slider 534 is no longer restrained against proximal motion under the influence of the spring 540. The width of the lower guide 552 is less than the width of the gap between the posts 544, and the lower guide 552 is substantially aligned with the gap between the posts 544. Thus, the lower guide 552 is free to slide through the gap between the posts 544 and through the proximal end of the holder 594. The proximal motion of the distal slider 534 thus takes up the slack (if any) in the second cable 490 connected to the distal slider 534, then causes that second cable 490 to move proximally. Referring also to FIG. 77, this is time t=3, at which the distal slider 534 has rapidly moved proximally from its position at time t=2, and the proximal slider 522 has moved slightly in the distal direction from its position at time t=2.

Referring also to FIG. 58, this proximal motion of the second cable 490 urges the sled 482, which also is connected to the second cable 490, into motion. As described above, at least one channel 496 is defined in the staple holder 38, and the second cable 490 is guided by a corresponding channel 496. The staple holder 38 is shaped such that the channel 496 curves and causes the second cable 490 to curve back in a proximal direction. The second cable 490 is connected to the sled 482. Thus, the curvature of the channel 496 causes the second cable 490 to curve, such that the proximal motion of the second cable 490 pulls the sled 482 distally. In this way, proximal motion of the distal slider 534 causes the sled 482 to move distally.

Referring also to FIGS. 64 and 68-69, the sled 482 includes one or more ramp elements 446, each movable within a corresponding passage 440 in an arm 402 of the staple holder 38, as described above. Initially, the sled 482 is positioned such that each ramp element 446 is proximal to the most proximal connector bay 448 connected to the corresponding passage 440. Thus, as the second cable 490 is tensioned and moved proximally by the distal slider 534, and the sled 482 moves distally as a result, each ramp element 446 moves distally in its corresponding passage 440.

For convenience in describing the deployment of staples 464, the motion of one ramp element 446 through the corresponding passage 440 will be described; the motion of each additional ramp element 446 through its corresponding passage 440 occurs in the same or a similar manner. Referring to FIG. 64, as the ramp element 446 moves distally from its initial position, its distal end 474 contacts the most proximal connector deployer 452. As described above, each connector deployer 452 initially is in a first position in which its outer end 454 extends into the passage 440. When the distal end 474 of the ramp element 446 contacts the most proximal connector deployer 452, it urges that connector deployer 452 into the corresponding connector bay 448. The distal end 474 of the ramp element 446 may be shaped such that its inner surface 476 curves or angles relative to the direction of travel of the ramp element 446. Thus, when the distal end 474 of the ramp element 446 encounters the outer end 454 of the most proximal connector deployer 452, a component of the force it exerts on the connector deployer 452 is substantially parallel to the longitudinal centerline of the corresponding connector bay 448. That centerline may be substantially perpendicular to the direction of travel of the ramp element 446, or may be otherwise oriented relative to the direction of travel of the ramp element 446.

As a result of contact with the distal end 474 of the ramp element 446, the connector deployer 452 begins to move through the corresponding connector bay 448, away from the passage 440. A connector 464 is located in the connector bay 448, inward from the connector deployer 452. The tines 466 of the connector 464 initially may be biased against at least part of the corresponding connector bay 448 as described above, or the connector 464 may otherwise be held within the connector bay 448 prior to motion of the connector deployer 452. As the connector deployer 452 moves, it exerts a force on the corresponding connector 464, overcoming the force with which the connector 464 is initially held in place and pushing the connector 464 inward. As the connector 464 is urged inward, the registration element 458 (if used) translates along the registration feature 462 of the connector bay 448. The registration element 458 reduces or eliminates lateral cocking of the connector deployer 452 during its translation through the connector bay 448, such that the connector deployer 452 is maintained in substantially the same orientation throughout its travel.

Referring also to FIG. 61 (in which the graft vessel and target vessel are not shown for clarity), as the connector deployer 452 urges the connector 464 out of the connector bay 448, the tines 466 of the connector 464 move out of the connector bay 448, penetrate the root 405 of the flap 408 held against the inner surface 450 of the arm 402, then penetrate the wall of the target vessel 580. One or more of the arms 402 may be angled relative to a horizontal plane to facilitate connecting the flaps of the graft vessel 404 to the wall of the target vessel 580, where that angle is chosen to place connectors in a desired orientation relative to the surface of the target vessel 580. Advantageously, the staples 464 enter the target vessel substantially perpendicular to it. However, the staples 464 can enter the target vessel at a different angle, and/or at different angles relative to one another.

After the tines 464 have completely penetrated the wall of the target vessel, they encounter corresponding staple bending features 572 in the anvil arm 14. The staple bending features 572 are depressions in the surface of the anvil arm 14, aligned with the connector bays 448 such that at least one tine 466 of at least one connector 464 encounters a staple bending feature 572 upon being pushed out of its connector bay 448. One or more of the staple bending features 572 may be configured differently, or may be omitted altogether. As the connector deployer 452 continues to urge the connector 464 out of the connector bay 448 and toward the anvil arm 14, the tines 464 of the connector 464 are pressed into the staple bending features 572. Thus, the force transmitted from the ramp element 446 to the connector deployer 452 presses the tines 464 into the staple bending features 572, causing them to deflect. The tines 464 may be deflected in any direction suitable for holding the flap 408 to the graft vessel 404.

When the widest portion of the distal end 474 of the ramp element 446 encounters the outer end 454 of the connector deployer 452, the connector deployer 452 reaches the end of its stroke through the connector bay. The connector 464 and the corresponding staple bending feature or features 572 are configured such that the deflection of the tines 446, and thus the deployment of the connector 464, is substantially complete when the corresponding connector deployer 452 reaches the end of its stroke. The ramp element 446 then continues its motion through the passage 440 to encounter the next connector deployer 452, such that the staples 464 in each arm 402 are deployed sequentially. Alternately, the ramp element 446 and passage 440 are configured such that the ramp element 446 moves in substantially the same direction as the sliders 452, or is otherwise connected to the sliders 452, such that two or more of the sliders 452 are actuated substantially simultaneously. That is, the sliders 452 may be actuated in series, in parallel, or in a different way. For example, the sliders 452 may be selectively actuated, such that a selected number of staples 464 can be deployed. The user can deploy a selected number of staples 464 based on the size of the graft vessel 404 or other relevant factors. That is, the staple line (the length along the target vessel 580 along which staples 464 are deployed) is adjustable. Such adjustment may be performed in any appropriate manner, such as by adjusting the distance traveled by each ramp element 446 during deployment of the staples 464. Alternately, other mechanisms or structures may be used to deploy the staples 464 from the connector bays 448 in a desired sequence.

As described above, the staple holder 38 includes two spaced-apart arms 402. A ramp element 446 proceeds distally through a corresponding passage 440 in each arm 402. Further, the connector bays 448 in each arm 402 are aligned in a substantially bilaterally symmetric manner. Thus, as the sled 482 translates distally, the distal end 474 of each ramp element 446 encounters a connector deployer 452 at substantially the same time, such that a connector 464 is deployed from each arm 402 at substantially the same time. As a result, the staple holder 38 sequentially deploys pairs of staples 446 into tissue as the ramp elements 446 move distally. Alternately, the connector bays 448 are staggered, such that staples 464 from each arm 402 are deployed at different times than staples from the other arm 402.

The sled 482 also includes vein knives 432. Each vein knife 432 translates through a corresponding vein knife passage 430 defined by a first channel 426 in the graft clip 412 and a second channel 428 in the flap receiving surface 406, as described above. The distal end 474 of each vein knife 432 is sharp. As described above, the vein knives 432 are initially in a first position, where the distal end 474 of each vein knife 432 is located proximal to the root 405 of the corresponding flap 408. As the second cable 490 is tensioned and pulled toward the handle 302 by the distal slider 534, the sled 482 moves distally. The vein knives 432, which are connected to the sled 482 move distally as well through the corresponding vein knife passages 430.

As each vein knife 432 moves distally, its sharp distal end 474 engages the proximal edge of the root 405 of the corresponding flap 408, entering the tissue of the flap 408 and beginning to make an incision therein. The serrations 438 on the graft clip blades 436 assist in holding the flap 408 as the corresponding vein knife 432 incises it. Alternately, those serrations 438 may assist in incising the flap 408, depending on their configuration. In addition, the serrations 438 may assist in holding the excess tissue incised from each flap 408, after the vein knife 432 has made an incision through the entire flap. The vein knives 432 do not extend as far in the distal direction as the ramp elements 446. Thus, as the sled 482 translates distally, the distal end 474 of each ramp element 466 reaches any given longitudinal position before the blade 434 of the corresponding vein knife 432. Consequently, the ramp element 466 causes a staple 446 to deploy at a particular longitudinal position before the corresponding vein knife 432 extends the incision in the flap 408 to that longitudinal position. By stapling before incising at any given longitudinal position, each flap 408 is held securely as it is cut by the corresponding vein knife 432. Alternately, at any given longitudinal position, the flap 408 is incised during or before deployment of a staple 446 at that position. Each vein knife 432 is positioned to cut the flap 408 far enough from the deployed staples 446 to minimize or eliminate interference with these staples 446, but close enough to the staples 446 to cut away excess tissue on the flap 408 that is not needed for the finished anastomosis.

Figure 45:
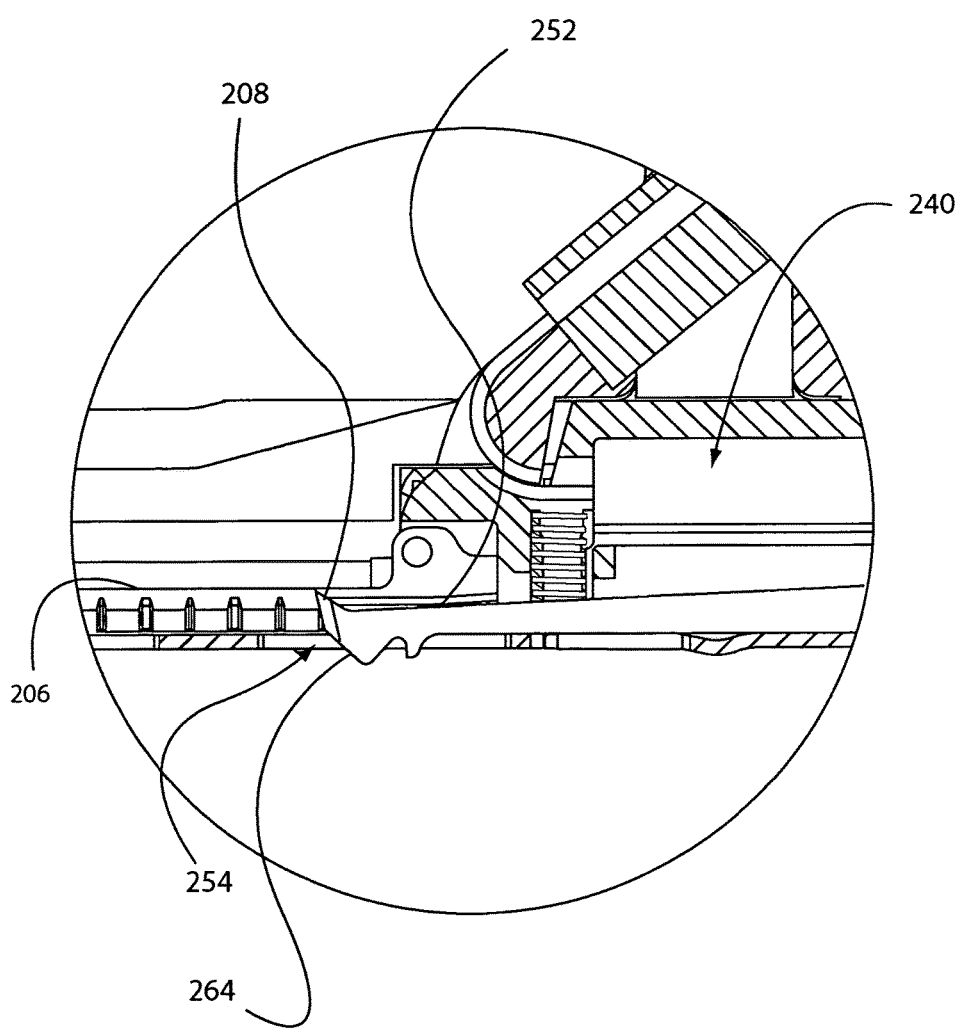
FIG. 45 is a side cutaway view of the anvil and staple holder of FIG. 34, where the cutter is in a second position.

Referring also to FIGS. 45, 58 and 68, the cutter 200 has been freed for translation. The cutter 200 is urged distally by the receiver 218, which engages the engagement feature 216 of the cutter 200. The receiver 218 may be defined in the sled 482, as described above. As the sled 482 is pulled distally by the second cable 490, the receiver 218 moves distally, thereby urging the engagement feature 216 of the cutter 200 distally. Alternately, the receiver 218 is not defined in the sled 482. Instead, the receiver 218 is a separate structure that may be connected to the sled 482, and that is configured to travel along a guide structure 241. The guide structure 241 is a rail or other structure along which the receiver 218 slide, and the receiver 218 interfaces with and translates along the rail. Thus, the guide structure 241 guides the translation of the receiver 218. A cavity 240 is provided in the staple holder 38 adjacent to the guide structure 241 to allow for motion of the receiver 218 along the guide structure 241. The cavity 240 is sized to allow the receiver 218 to translate freely. Alternately, the guide structure 241 is a hollow channel defined within the staple holder 38, such that the walls of the channel guide the translation of the receiver 218. Alternately, the guide structure 241 may be any other structure or mechanism capable of guiding the translation of the receiver 218. The guide structure 241 is substantially aligned with the anvil arm 14. That is, the longitudinal centerline of the guide structure 241 is substantially parallel to the longitudinal centerline of the anvil arm 14. Thus, motion of the receiver 218 along the guide structure 241 causes translation of the engagement feature 216 and therefore translation of the cutter 200 substantially parallel to the centerline of the anvil arm 14. The receiver 218 may be actuated to translate along the guide structure 241 by the second cable 490, which transmits force from the handle 302. Alternately, the actuator may convert stored energy to force that is applied to the cutter. Such stored energy may be provided by a spring, battery, source of compressed gas, or other source. Alternately, any mechanism, structure or method, using stored energy or not, may be used to translate the receiver 218 along the guide structure 241. The particular mechanism, structure or method used to cause translation of the cutter 200 is not critical to the invention.

The upper surface 252 of the cutter 200 is substantially planar proximal to the projection 208. The biasing element 260 contacts the upper surface 252 of the cutter 200 and biases the cutter 200 downward. The cutter 200 includes a keel 264 that extends downward. The keel 264 may be formed into the cutter 200, or may be a separate component connected to the cutter 200. The keel 264 is substantially as wide as the adjacent portion of the cutter 200. However, the keel 264 may be wider or narrower than the adjacent portion of the cutter 200. The keel 264 is positioned at or near the distal end of the cutter 200. Alternately, the keel 264 may be positioned at a different location on the cutter 200.

Figure 43A:
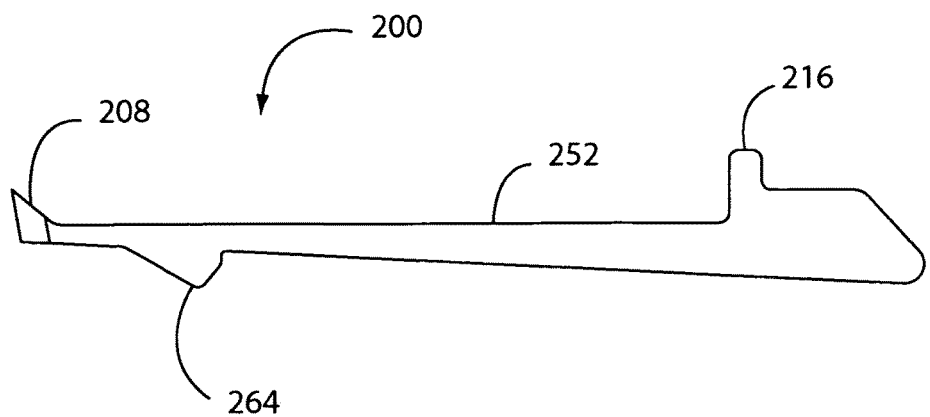
FIG. 43A is a side view of another embodiment of a cutter.

Referring to FIG. 43A, another embodiment of a cutter 200 is shown. As described above, the cutter 200 includes at least one projection 208 extending substantially upward from a position at or near its distal end, and an engagement feature 216 extending upward from the upper surface 252 of the cutter 200. In this embodiment, the keel 264 of the cutter 200 is spaced apart from the projection 208, differing from the embodiment of FIG. 37-38 in which the keel 264 is adjacent to the projection 208. By spacing the keel 264 apart from the projection 208, the keel 264 can project a smaller distance downward while moving the projection 208 substantially the same amount upward and downward. Consequently, the keel 264 as a whole can be made smaller.

Figure 43B:
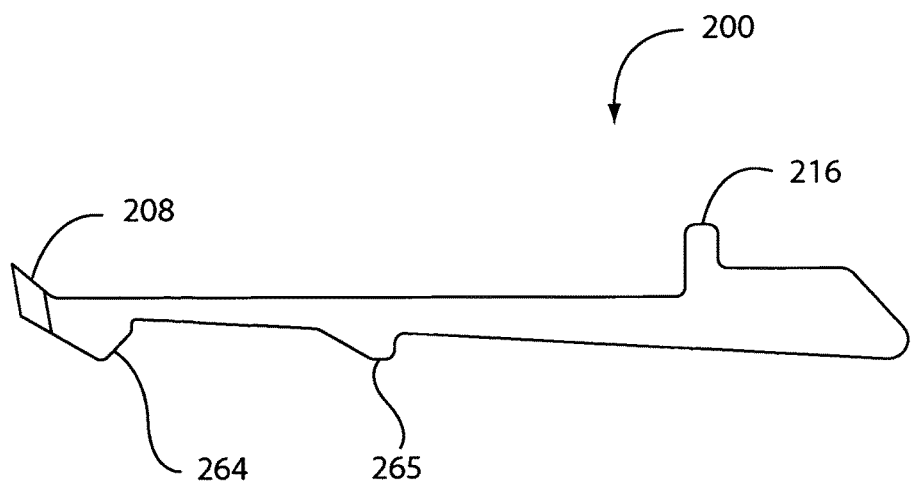
FIG. 43B is a side view of another embodiment of a cutter.

Referring to FIG. 43B, another embodiment of a cutter 200 is shown. As described above, the cutter 200 includes at least one projection 208 extending substantially upward from a position at or near its distal end, and an engagement feature 216 extending upward from the upper surface 252 of the cutter 200. In this embodiment, the cutter 200 includes a first keel 264 and a second keel 265. The first keel 264 may be configured similarly to the keel 264 of FIG. 43, and the second keel 265 may be configured similarly to the keel 265 of FIG. 43A. The first keel 264 extends further below the body of the cutter 200 than the second keel 265. A third lower opening (not shown) is defined through a lower surface 256 of the anvil 10, in addition to the first lower opening 254 and the second lower opening 268. The third lower opening is spaced apart from the second lower opening 268, and is positioned distal to the second lower opening 268. The first keel 264 initially extends into the second lower opening 268, and the second keel 265 initially extends into the first lower opening 254.

As shown in FIG. 45, the keel 264 initially extends into the first lower opening 254, which is defined through a lower surface 256 of the anvil 10. The keel 264 may extend completely through the first lower opening 254, such that its lowest point extends outside the anvil 10. The keel 264 is biased downward into the first lower opening 254 as a result of the downward force exerted on the cutter 200 by the biasing element 260. While the keel 264 is biased into the first lower opening 254, the projection 208 remains below the contact surface 206 of the anvil arm 14. In this way, the projection 208 does not extend out of the anvil arm 14 while the anvil arm 14 is inserted into the wall of a target vessel. Where the cutter 200 of FIG. 43A is used, the keel 264 need not extend into or through the first lower opening 254 as far as the keel 264 of the cutter 200 of FIGS. 37-38. As a result, less clearance for the motion of the keel 264 need be provided, and the tissue effector 400 may be made more compact. The first lower opening 254 extends along a fixed length of the lower surface 256 of the anvil 10. As the cutter 200 translates distally, the keel 264 continues to remain at least partially within the first lower opening 254, such that the projection 208 continues to remain below the contact surface 206 of the anvil arm 14. Initially, the keel 264 may be positioned proximal to the distal end of the first lower opening 254. The length of the first lower opening 254 is selected to cause the projection 208 to remain below the contact surface 206 of the anvil arm 14 across that distance. That is, this distance is selected such that the projection 208 on the cutter 200 does not engage the wall of the target vessel until the projection 208 is positioned within the circumference of the graft vessel. That is, the connection between the graft vessel and the target vessel substantially defines a closed area, and the projection 208 is configured to engage the wall of the target vessel within that closed area. In this way, the projection 208 makes an incision completely within the connection between the graft vessel and the target vessel, completing the anastomosis between the two vessels and minimizing or eliminating leakage at the anastomosis site. While the projection 208 on the cutter 200 remains below the upper surface of the anvil arm 14, it neither engages nor cuts the wall of the target vessel.

Figure 46:
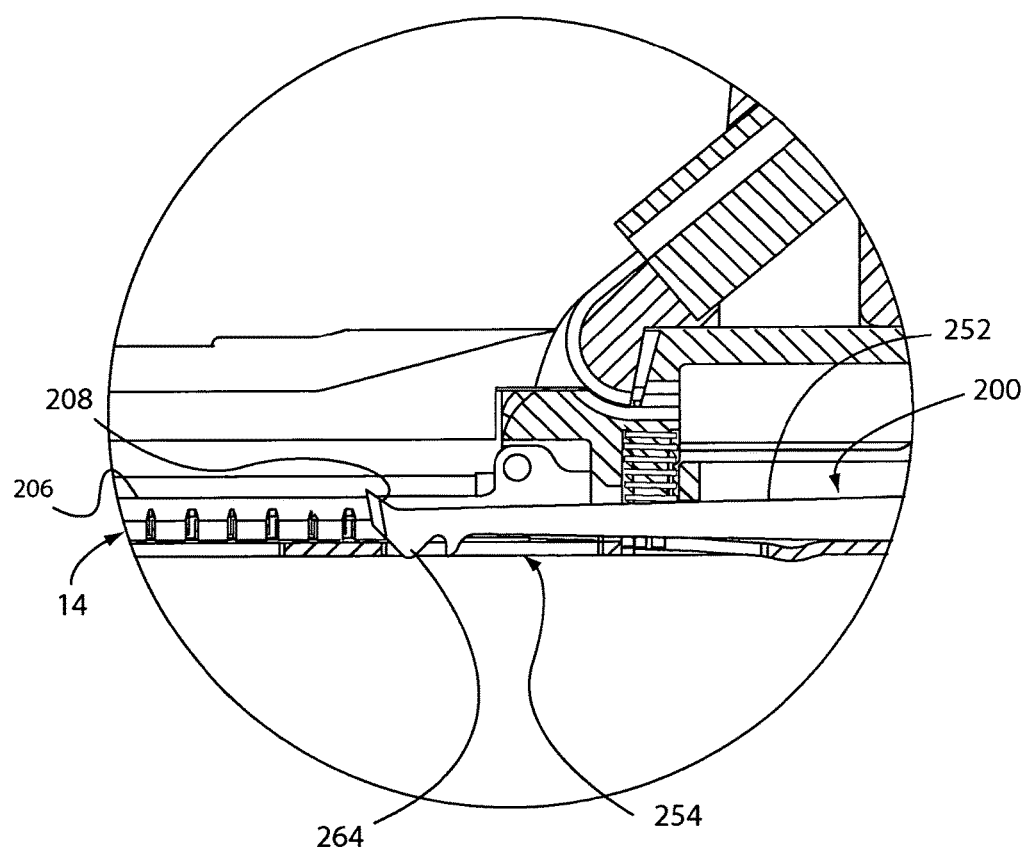
FIG. 46 is a side cutaway view of the anvil and staple holder of FIG. 34, where the cutter is in a third position.

Referring also to FIG. 46, the cutter 200 continues to advance distally as the receiver 218 continues to urge the engagement feature 216 distally. As described above, at least the distal end of the cutter 200 is biased downward. As the cutter 200 advances distally, the keel 264 encounters the distal end of the first lower opening 254. This encounter, and the continued proximal translation of the cutter 200, causes the keel 264 to move upward relative to the anvil arm 14. The keel 264 and/or the distal end of the first lower opening 254 may be constructed to provide a smooth, gradual upward motion of the keel 264, such as by providing a gradual slope on the keel 264 and/or the distal end of the first lower opening 254. Alternately, the keel 264 and/or the distal end of the first lower opening 254 may be constructed to allow or cause the keel 264 to move upward abruptly upon encountering the distal end of the first lower opening 254. The upward motion of the keel 264 causes the distal end of the cutter 200 and the projection 208 to move upward. Thus, the size and position of the first lower opening 254, including the position of the distal end of the first lower opening 254, control the motion of the cutter 200 and the projection 208 in the vertical direction.

Where the cutter 200 of FIG. 43A is used, the keel 264 contacts the distal end of the first lower opening 254 in the same manner as the cutter of FIGS. 37-38. By spacing the keel 264 apart from the projection 208, the projection 208 may be protected from inadvertent contact with the distal end of the first lower opening 254. The initial position of the cutter 200 relative to the remainder of the tissue effector 400 may be different than that of the cutter 200 of FIGS. 37-38, to ensure that the projection 208 enters the wall of the target vessel at a selected point relative to the tissue effector 400. Where the cutter 200 of FIG. 43B is used, as the cutter 200 is urged distally, the second keel 265 and the first lower opening 254 are configured such that the second keel 265 contacts the distal end of the first lower opening 254 before the first keel 264 can contact the distal end of the second lower opening 268. In this way, the distal end of the cutter 200 is prevented from contacting the distal end of the second lower opening 268.

As the distal end of the cutter 200 moves upward, the projection 208 moves upward through the upper opening 248 in the anvil arm 14. The contact surface 206 of the anvil arm 14 is substantially adjacent to the inner surface of the wall of the target vessel. Thus, upward motion of the projection 208 through the upper opening 248 and above the contact surface 206 of the anvil arm 14 causes the projection 208 to enter the wall of the target vessel. The cutter 200 continues to move distally, such that the keel 264 moves out of the first lower opening 254 completely and contacts the bottom surface 266 of the channel 246 of the anvil arm 14. The projection 208 is sized such that the projection 208 completely penetrates the wall of the target vessel when the keel 264 has moved proximally to the first lower opening 254 and is in contact with the bottom surface 266 of the channel 246. That is, at least a portion of the projection 208 passes through the wall of the target vessel and enters the lumen of the target vessel. This initial penetration of the wall of the target vessel defines the starting point of an arteriotomy performed on the target vessel by the projection 208. The starting point of the arteriotomy is spaced apart from the location on the target vessel at which the anvil arm 14 is inserted, because the cutter 200 and the projection 208 have moved proximally a selected distance before penetrating or incising the wall of the target vessel. The portion of the wall of the target vessel between the arteriotomy and the insertion point of the anvil arm 14 may be referred to as a tissue bridge. The incision is referred to as an arteriotomy for convenience, and this terminology does not limit the type of anastomosis that may be performed. For example, anastomosis may be performed between two tissue structures that are not blood vessels, such as bile ducts.

The projection 208 of the cutter 200 enters the wall of the target vessel at a location between the arms 402 of the staple holder 38. Each arm 402 holds at least a portion of a flap 408 of the graft vessel 404 against the wall of the target vessel, such that the projection 208 enters the wall of the target vessel at a location between the flaps 408. The length of the cutter 200, the position of the projection 208 on the cutter 200, and the placement of the first lower opening 254 may be selected such that the projection 208 enters the wall of the target vessel after at least one staple 446 is deployed into one of the flaps 408 and the wall of the target vessel. Alternately, the projection 208 enters the wall of the target vessel before any of the staples 446 have been deployed, or after all of the staples 446 have been deployed. Further, the length of the cutter 200, the position of the projection 208 on the cutter 200, and the placement of the first lower opening 254 may be selected such that the projection enters the wall of the target vessel at substantially the same time that one or more vein knives 432 begin to incise the corresponding flaps 408.

Figure 47:
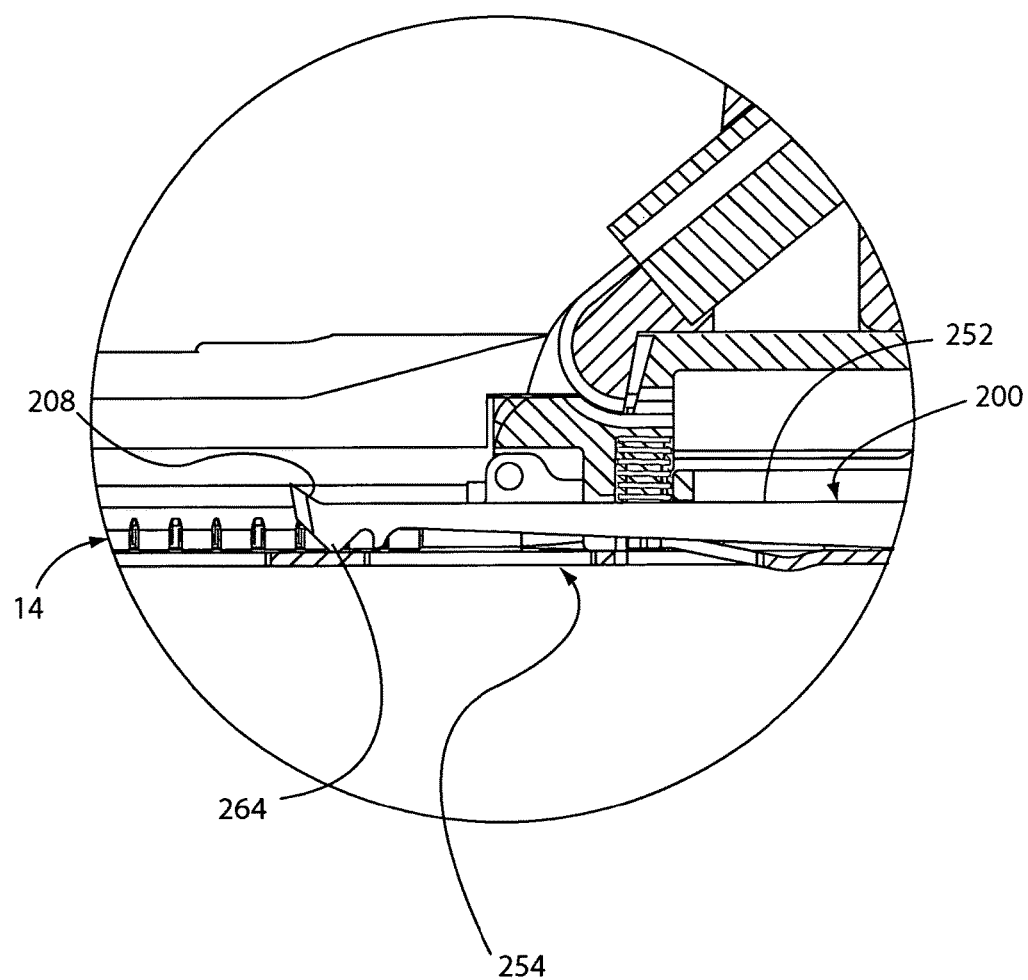
FIG. 47 is a side cutaway view of the anvil and staple holder of FIG. 34, where the cutter is in a fourth position.

As the sled 482 continues to advance distally, the distal end 474 of each ramp element 476 actuates each connector deployer 452 in turn, causing the sliders 452 to sequentially deploy the corresponding staples 446 as described above. Additionally, the vein knives 432 continue to move distally as the sled 482 advances distally, lengthening the incision in the root 405 of each flap 408. Further, referring also to FIG. 47, the cutter 200 continues to advance distally as the receiver 218 continues to urge the engagement feature 216 distally. The cutter 200 incises the wall of the target vessel at a given longitudinal position at substantially the same time as each vein knife 432 incises the corresponding flap 408 at the that longitudinal position. Alternately, the timing of the cutting action of the cutter 200 and the vein knives 432 is different, such that the cutter 200 incises the wall of the target vessel at a given longitudinal position either before or after each vein knife 432 incises the corresponding flap 408 at that longitudinal position.

The lower surface of the keel 264 contacts the bottom surface 266 of the channel 246 during this translation. The contact between the keel 264 and the bottom surface 266 of the channel 246 counteracts the downward bias of the distal end of the cutter 200. In this way, the projection 208 is maintained above the contact surface 206 of the anvil arm 14. As the cutter 200 continues to translate distally, the projection 208 moves through the tissue of the wall of the target vessel in a direction substantially parallel to the longitudinal centerline of the anvil arm 14, and incises the tissue of the wall of the target vessel to create an arteriotomy. Because the projection 208 is connected to and translated by the cutter 200, which is within the target vessel, the arteriotomy is performed from within the target vessel. The tip of the projection 208 may maintain substantially the same height relative to the contact surface 206 of the anvil arm 14 during translation of the cutter 200, or may change its height relative to the contact surface 206 of the anvil arm, as long as the projection 208 continues to incise completely through the wall of the target vessel.

Where the cutter of FIG. 43B is used, the lower surface of the second keel 265 and the lower surface of the first keel 264 both contact the bottom surface 266 of the channel 246. Alternately, the lower surface of the first keel 264 extends downward enough that the lower surface of the second keel 265 does not contact the bottom surface 266 of the channel 246.

Figure 48:
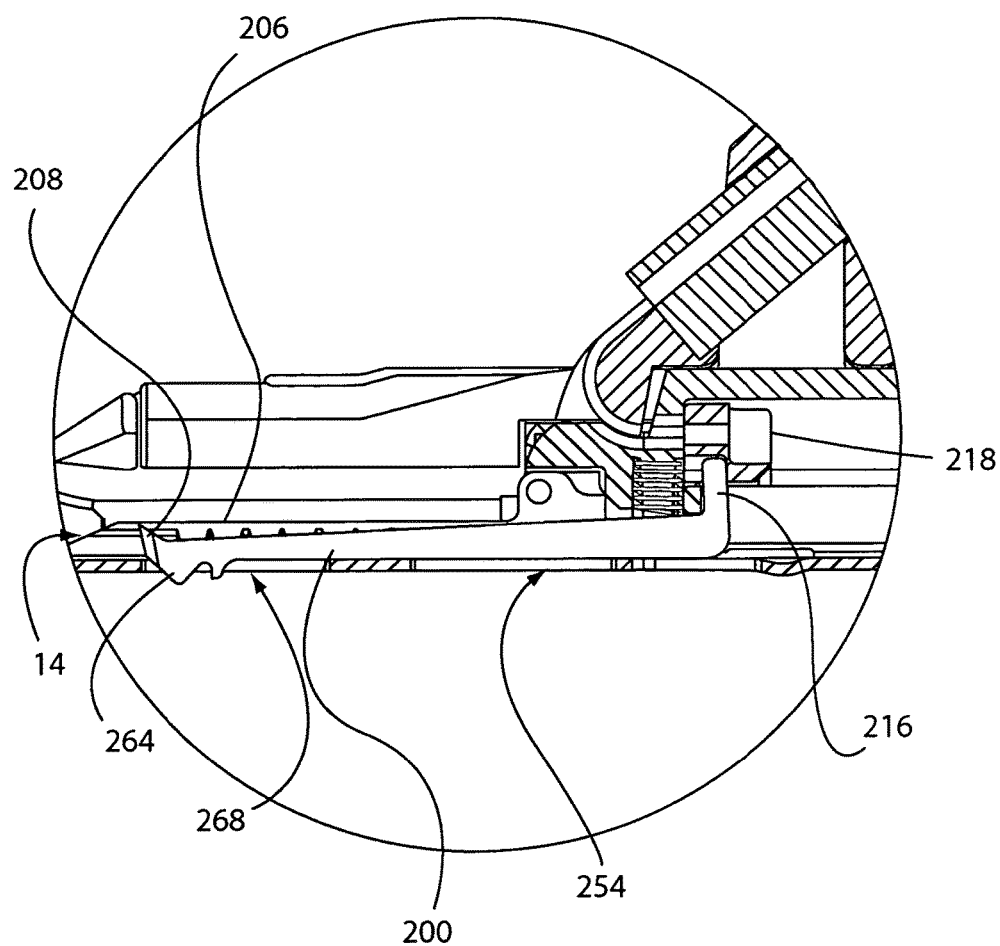
FIG. 48 is a side cutaway view of the anvil and staple holder of FIG. 34, where the cutter is in a fifth position.

Referring also to FIG. 48, a second lower opening 268 is defined through the lower surface 256 of the anvil arm 14. The second lower opening 268 is distal to and substantially aligned with the first lower opening 254. The cutter 200 continues to advance distally as the receiver 218 continues to impel the engagement feature 216 distally. As a result of this translation, the keel 264 encounters the proximal end of the second lower opening 268. Because the distal end of the cutter 200 is biased downward, the keel 264 moves downward at least partially into the second lower opening 268. The downward motion of the keel 264 causes the distal end of the cutter 200 and the projection 208 to move downward. The keel 264 and/or the proximal end of the second lower opening 268 may be constructed to provide a smooth, gradual downward motion of the keel 264, such as by providing a gradual slope on the keel 264 and/or the proximal end of the second lower opening 268. Alternately, the keel 264 and/or the proximal end of the second lower opening 268 may be constructed to allow or cause the keel 264 to move downward abruptly upon encountering the proximal end of the second lower opening 268. Alternately, where the cutter 200 of FIG. 43B is used, the first keel 264 moves as least partially into the third lower opening 269, and the second keel 264 moves at least partially into the second lower opening 268. The downward motion of the distal end of the cutter 200 causes the projection 208 to retract into or completely through the upper opening 248, such that the projection 208 no longer encounters the tissue of the wall of the target vessel. The projection 208 may be urged downward completely into the channel 246, depending on the depth of the channel 246 and the height of the projection 208.

Alternately, the upper tip of the projection 208 may remain within the upper opening 248. The cutter 200 may stop its distal translation at substantially the same time that the projection 208 retracts completely into the upper opening 248, or may continue to translate distally within the channel 246 before coming to a stop. Alternately, the second lower opening 268 is not provided, and only the first lower opening 254 extends through the lower surface 156 of the anvil 14 into the channel 246. In such a configuration, the cutter 200 is retracted in the proximal direction after the arteriotomy is formed, until the keel 264 moves downward into the first lower opening 254 and the projection 208 consequently retracts completely into the upper opening 248.

Figure 76:
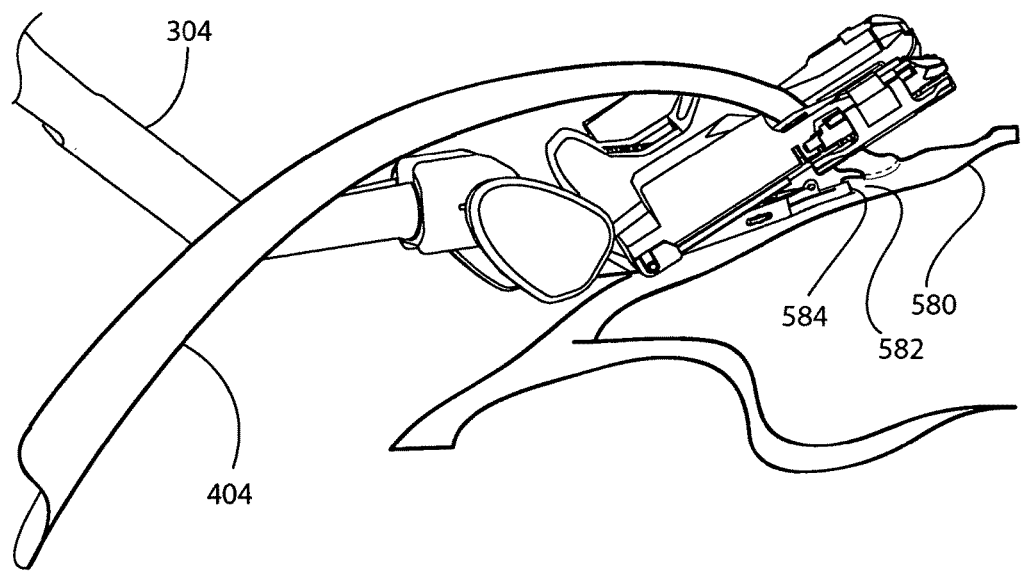
FIG. 76 is a perspective view of the tissue effector of FIG. 74, after the graft vessel has been connected to the target vessel and before the anvil of the tissue effector has been removed from the lumen of the target vessel.

The sled 482 continues to move distally, such that the distal end 474 of the ramp element 446 actuates the most distal connector deployer 452 and deploys the corresponding staple 446. Referring also to FIG. 76, the connection between the end of the graft vessel 404 and the target vessel 580 is then complete. The sled 482 continues to translate, such that each vein knife 432 then moves completely through the corresponding flap 408. A portion of each flap 408 continues to be held between each graft clip 412 and corresponding flap receiving surface 406. Thus, when the root 405 of each flap 408 has been completely incised through by the corresponding vein knife 432, the staple holder 38 no longer holds the graft vessel 404, and is freed from the anastomosis site.

Figure 73:
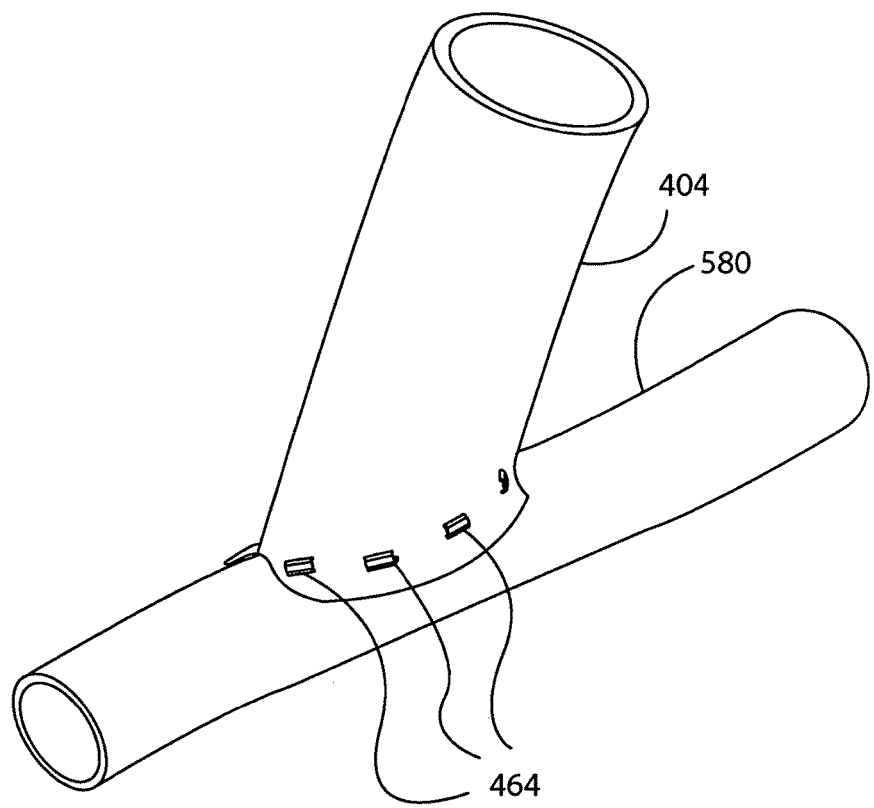
FIG. 73 is a perspective view of a completed anastomosis.

Referring to FIG. 73, the rocker 508 completes its travel when the distal end 520 of the distal arm 516 contacts one or more of the ribs 556 in the handle 302. This contact prevents further downward motion of the distal arm 518, and thereby causes the rocker 508 to cease its motion. Alternately, at least a portion of the distal arm 516 and/or the proximal arm 514 contact a stop or other structure in the handle 302 which obstructs further motion of the rocker 508. Alternately, the motion of the rocker 508 is stopped in a different way, such as by a braking or clutch mechanism. Thus, the corresponding travel of the second cable 490 and the connected sled 482 cease as well. After the rocker 508 has completed its travel, the upper portion 532 of the contact feature 528 of the proximal slider 522 contacts the proximal end 516 of the proximal arm 514. The spring 546 biases the proximal slider 522 distally. Thus, the upper portion 532 of the contact feature 528 is pressed against the proximal end 516 of the proximal arm 514, holding the proximal arm 514 and the rocker 508 in place and substantially preventing rotation of the rocker 508 in a direction opposite to its previous motion. Alternately, the proximal slider 522 does not contact the rocker 508 after the travel of the rocker 508 is complete. At substantially the same time as the motion of the rocker 508 stops, the lower guide 552 of the distal slider 534 contacts a stop 553 defined in or connected to the handle 302. The stop 553 may be integrated with at least one of the ribs 556. The stop 553 is positioned to interfere with further proximal motion of the distal slider 534, such that contact between the lower guide 552 and the stop 553 causes the distal slider 534 to cease moving proximally. Alternately, the stop 553 is not used, and the distal slider 534 is allowed to continue to move proximally after deployment of the staples 446. Referring also to FIG. 77, this is time t=4, at which the distal slider 534 has moved proximally from its position at time t=3, and the proximal slider has moved slightly distally from its position at time t=3.

As described above, the distal slider 534 may include a verification stub 560 that extends substantially upward from the upper end of the distal slider 534 through a slot 562 in the handle 302. Initially, when the distal slider 534 is in its most distal position, the verification stub 560 is also in its most distal position. As the distal slider 534 translates proximally during actuation of the anastomosis tool 300, the verification stub 560 also translates proximally. Thus, after the anastomosis tool 300 has been actuated and the distal slider 534 has moved to its most proximal position, the verification stub 560 has moved to its most proximal position as well. By visually inspecting the position of the verification stub 560, the user can confirm whether the anastomosis tool 300 has been completely actuated. In addition, the distal end 474 of at least one ramp element 446 may be visible after actuation of the anastomosis tool 300 if the distal end 442 of the passage 440 is open, providing another visual indication that the anastomosis tool 300 has been completely actuated. The distal end of the first lower opening 254 and the proximal end of the second lower opening 268 control the motion of the projection 208 and thereby control the penetration of the wall of the target vessel. That is, the distance between the distal end of the first lower opening 254 and the proximal end of the second lower opening 268 determines the length of the arteriotomy.

Alternately, where the snap arm 606 is used instead of the cam lock to hold a corresponding graft clip 412 in the closed position, the distal end 474 of the corresponding ramp element 446 extends out of the distal end 442 of the passage 440 to disengage the catch 608 of the snap arm 606. That is, the lobe 610 of the snap arm 606 is positioned relative to the distal end 442 of the passage 440 such that the distal end 474 of the corresponding ramp element 446 encounters the lobe 610 near the end of the travel of the ramp element, pushing the lobe 610 out of engagement of the arm 402 and thus disengaging the catch 608 from the arm 402. The corresponding graft clip 412 is thereby free to move out of the closed position, freeing the flap 408 held by that graft clip 412. In such an embodiment, the vein knives 432 may be omitted, because the flaps 408 are freed in their entirety. Further, the spikes 410 are omitted, such that the flaps 408 are not held in place on the flap receiving surface 406 after the snap arm 606 is disengaged from the arm 402.

After performing the arteriotomy, the cutter 200 is in a distally-extended position. The cutter 200 remains in that position as the anvil arm 14 is removed from the target vessel 580, where the tissue bridge 582 separates the anastomosis site from the hole 584 in the wall of the target vessel 580 through which the anvil arm 14 entered the target vessel 580. Thus, the projection 208 does not extend out of the upper opening 248 during removal of the anvil arm 14 from the target vessel 580. Alternately, after performing the arteriotomy, the cutter 200 may be moved proximally within the channel 246 in the anvil arm 14 before removing the anvil arm 14 from the target vessel 580.

The tissue effector 400 is then returned to the open position from the closed position, to allow the anvil arm 14 to be withdrawn from the target vessel 580. After the trigger 308 has been depressed to deploy one or more connectors 464, the distal arm 518 of the rocker 508 has deflected at least a portion of the holder 594. As a result, the deflected holder 594 exerts an opposing bias against the distal arm 518 of the rocker 508. When the user releases the trigger 308, the biased holder 594 then acts against the distal arm 518, pushing it upward and causing the rocker 508 to rotate about the rocker axle 510. As a result, the proximal arm 514 of the rocker 508 moves downward toward its original position. Thus, the proximal end 516 of the proximal arm 514 moves downward against the upper portion 532 of the contact feature 528 of the proximal slider 522, and continues to move downward past the intersection between the two portions 530, 532 of the contact feature 528. As the proximal end 516 of the proximal arm 514 moves past that intersection to contact the lower portion 530 of the contact feature 528, the proximal slider 522 is freed to move distally a small amount due to the bias of the spring 546. This proximal motion relaxes the tension on the first cable 480. As a result, the biasing element 475 pushes the staple holder 38 away from the anvil 10, returning the tissue effector 400 to the open position. The tissue effector 400 thus no longer clamps the wall of the target vessel 580, and the anvil arm 14 can be removed from the lumen of the target vessel 580. The spacing between the staple holder 38 and the anvil 10 in the open position is selected to ensure adequate clearance for separation of the tissue effector 400 from the target vessel 580. For example, the staple holder 38 is moved far enough from the anvil 10 such that the spikes 410 are fully removed from the flaps 408 before the anvil arm 14 is removed from the target vessel 580. Alternately, the tissue effector 400 is returned to the open position in another manner. When the projection 208 is retracted out of the tissue of the wall of the target vessel, the distal end of the arteriotomy is defined, and the arteriotomy is complete. Thus, the anastomosis is complete as well.

Referring also to FIG. 74, the completed anastomosis between the graft vessel 404 and the target vessel 580 remains. The hole 584 in the wall of the target vessel 580 through which the anvil arm 14 entered the target vessel 580 is small enough to prevent significant bleeding through the puncture site after the anvil arm 14 has been withdrawn. Alternately, the hole 584 is closed by hand suturing. Alternately, the hole 584 is closed with a biocompatible glue, adhesive or the like. Alternately, the hole 584 is closed with a clip, clamp, or other implantable device that remains on the target vessel. Such a device may be positioned on the outer surface and/or inner surface of the target vessel, and may extend into the hole 584. A device for closing the hole 584 may be constructed from nitinol or other superelastic or pseudoelastic material, or from stainless steel or other material, where that device moves between a first configuration and a second configuration during deployment, and where the second configuration holds the hole 584 closed. The hole 584 is less than substantially 2 mm wide, and advantageously less than 1 mm wide.

As described above, the cutter 200 incises the wall of the target vessel while the staple holder 38 is stapling or otherwise connecting the graft vessel to the target vessel, as described in greater detail below. Alternately, the staple holder 38 may completely staple or otherwise connect the graft vessel to the target vessel before the cutter 200 is urged forward, such that the two vessels are connected before the cutter 200 makes an incision between them. Alternately, the cutter 200 incises the wall of the target vessel before the staple holder 38 has stapled or otherwise connected the graft vessel to the target vessel.

Figure 49:
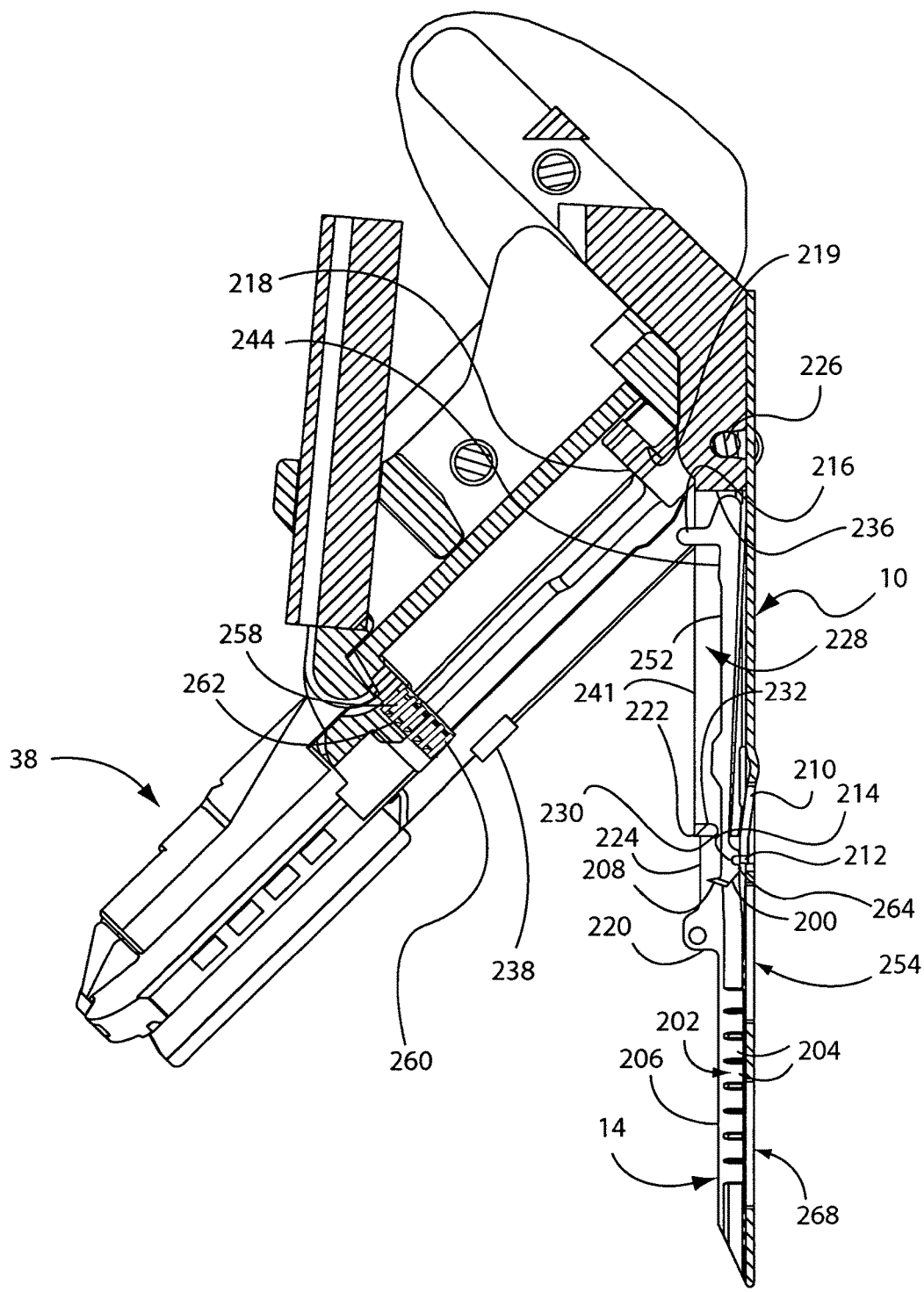
FIG. 49 is a side cutaway view of a second embodiment of an anvil and a staple holder, where the anvil and staple holder are spaced apart from each other.

Referring to FIG. 49, a different embodiment of the anvil 10 also includes a cutter 200 moveable relative to the anvil 10 for making an incision in the wall of a target vessel. The anvil 10, anvil arm 14, staple holder 38, and other components are substantially as described above with regard to FIGS. 34-38 and 44-49. In this embodiment, at least the distal end of the cutter 200 is biased upward. In other regards, the actuation of the anastomosis tool 300, the operation of the mechanisms within the handle 302, and the operation of the tissue effector 400 are substantially as described above. Referring to FIGS. 35 and 49, the anvil insert 222 is connected to the anvil 10. An aperture 230 is defined through the distal end of the anvil insert 222 into the cavity 228 defined within the anvil insert 222, connecting the channel 246 to the cavity 228. The cutter 200 extends through the aperture 230 in the anvil insert 222, such that the distal end of the cutter 200 is positioned within the channel 246 and the proximal end of the cutter 200 is positioned within the cavity 228. A cam 232 is positioned within the cavity 228 above the aperture 230. Alternately, the cam 232 may be positioned differently relative to the aperture 230. The cam 232 is a structure used in controlling the motion of the cutter 200, as is described in greater detail below.

At least the distal end of the cutter 200 may be biased upward. This biasing may be performed by any appropriate structure or mechanism, such as by one or more springs (not shown). Such a spring or springs may act in compression to push the distal end of the cutter 200 upward, or may act in tension to pull the distal end of the cutter upward. As another example, the cutter 200 may be constructed from an elastic or superelastic material that is formed in such a way as to produce an upward bias. The entire cutter 200 may be biased upward, if desired. At least the distal end of the cutter 200 is biased upward during the translation of the cutter 200 along the anvil arm 14. Alternately, the cutter 200 is not biased, either upward or downward. Instead, the cutter 200 is urged upward and downward at different locations during its translation by the interaction between at least one cam follower on the cutter 200 and at least the cam 232.

Figure 50:
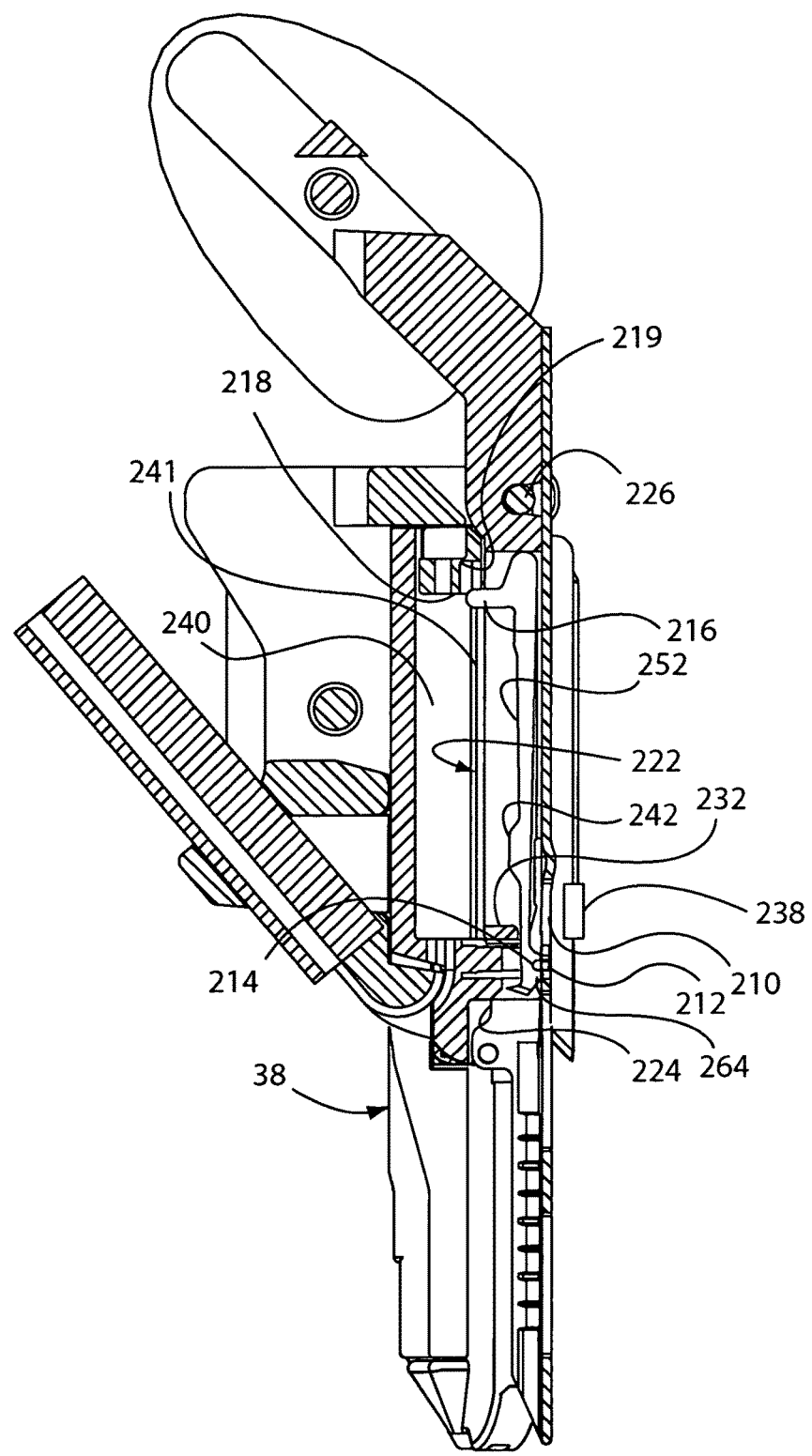
FIG. 50 is a side cutaway view of the anvil and staple holder of FIG. 40, where the cutter is in a first position.

As shown in FIG. 49, the distal end of the anvil arm 14 is spaced apart from the staple holder 38. The anvil arm 14 is inserted through the wall of the target vessel, as described above, such that the contact surface 206 of the anvil arm 14 is in substantial contact with the inner wall of the target vessel. Next, referring to FIG. 50, the staple holder 38 and anvil 10 are moved relative to one another into the standby position, as described above. In the standby position, the cutter 200 is freed for translation along the channel 246, because the tip 212 of the safety feature 210 no longer engages the safety recess 214 of the cutter 200. At least the distal end of the cutter 200 is biased upward, and the cam 232 limits the upward motion of the cutter 200 by contacting at least a portion of the upper surface 252 of the cutter 200. The cam 232 controls the motion of the distal end of the cutter 200 in the vertical direction as the cutter 200 translates within the channel 246. Because the projection 208 is fixed to the cutter 200, the cam 232 also controls the motion of the projection 208 in the vertical direction, and thus controls the location at which the projection 208 encounters the wall of the target vessel.

Figure 51:
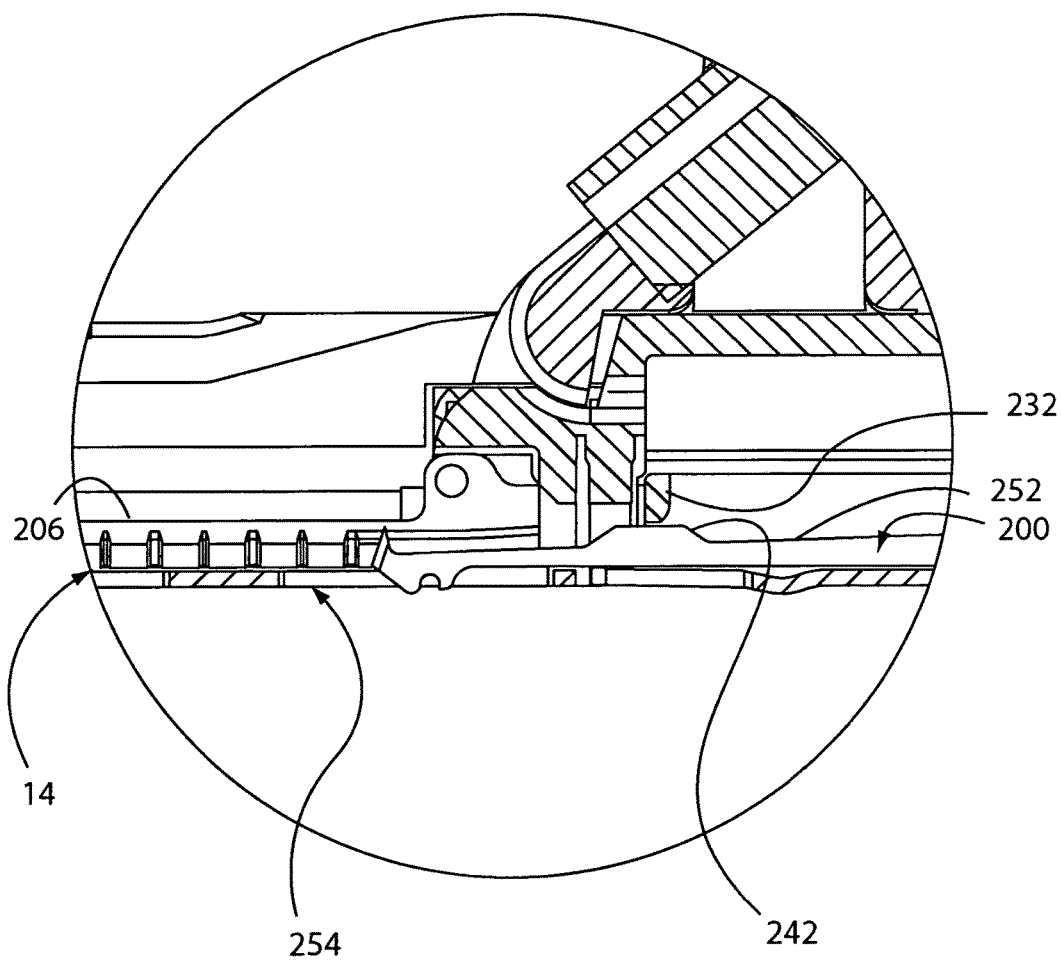
FIG. 51 is a side cutaway view of the anvil and staple holder of FIG. 40, where the cutter is in a second position.

Referring also to FIG. 51, after the cutter 200 has been freed for translation, it is urged distally by the receiver 218 as described above. A first cam follower 242 is defined on the upper surface 252 of the cutter 200. The first cam follower 242 is a raised structure formed into the upper surface 252 of the cutter 200. Alternately, the first cam follower 242 is a separate structure or mechanism constructed separately from the cutter 200 and later connected to the cutter 200. Alternately, the first cam follower 242 may be located on a surface of the cutter 200 in addition to or instead of its upper surface 252, depending on the position and configuration of the cam 232. The first cam follower 242 may be shaped as a trapezoid or similar shape, or may be shaped differently.

The cam 232 is fixed, and the first cam follower 242 is raised relative to the upper surface 252 of the cutter 200. At least the distal end of the cutter 200 is biased upward. Thus, as the cutter 200 translates distally, the cam 232 engages the first cam follower 242 and causes the cutter 200 to move downward. The cam 232 and the first cam follower 242 are shaped to smoothly engage each other. Alternately, the first cam follower 242 is shaped to induce the cutter 200 to abruptly move downward when the first cam follower 242 initially encounters the cam 232. The height of the first cam follower 242 relative to the contact surface 206 of the anvil arm 14 determines the distance that the distal end of the cutter 200 is moved downward. As described above, the cutter 200 may include a keel 264 or similar projection extending downward. As the distal end of the cutter 200 moves downward, the keel 264 or other projection moves into the first lower opening 254. In this embodiment, the first lower opening 254 does not control the motion of the cutter 200; instead, it provides a space for the keel 264 to move downward without interfering with the vertical motion of the distal end of the cutter 200. If the keel 264 is omitted, the first lower opening 254 and the second lower opening 268 may be omitted as well.

The connection between the graft vessel and the target vessel substantially defines a closed area, and the projection 208 is configured to engage the wall of the target vessel within that closed area. That is, the end of the graft vessel has a perimeter that contacts the side of the target vessel, such that the perimeter of the end of the graft vessel defines a closed area on the wall of the target vessel. In this way, the projection 208 makes an incision completely within the connection between the graft vessel and the target vessel, completing the anastomosis between the two vessels and minimizing or eliminating leakage at the anastomosis site. While the projection 208 on the cutter 200 remains below the contact surface 206 of the anvil arm 14, it neither engages nor cuts the wall of the target vessel. Thus, the first cam follower 242 is sized to translate the tip of the projection 208 below the contact surface 206 of the anvil arm 14 for a selected distance such that the projection 208 does not engage the tissue of the target vessel until the projection 208 is positioned to enter the closed area on the wall of the target vessel defined by the perimeter of the end of the graft vessel.

Figure 52:
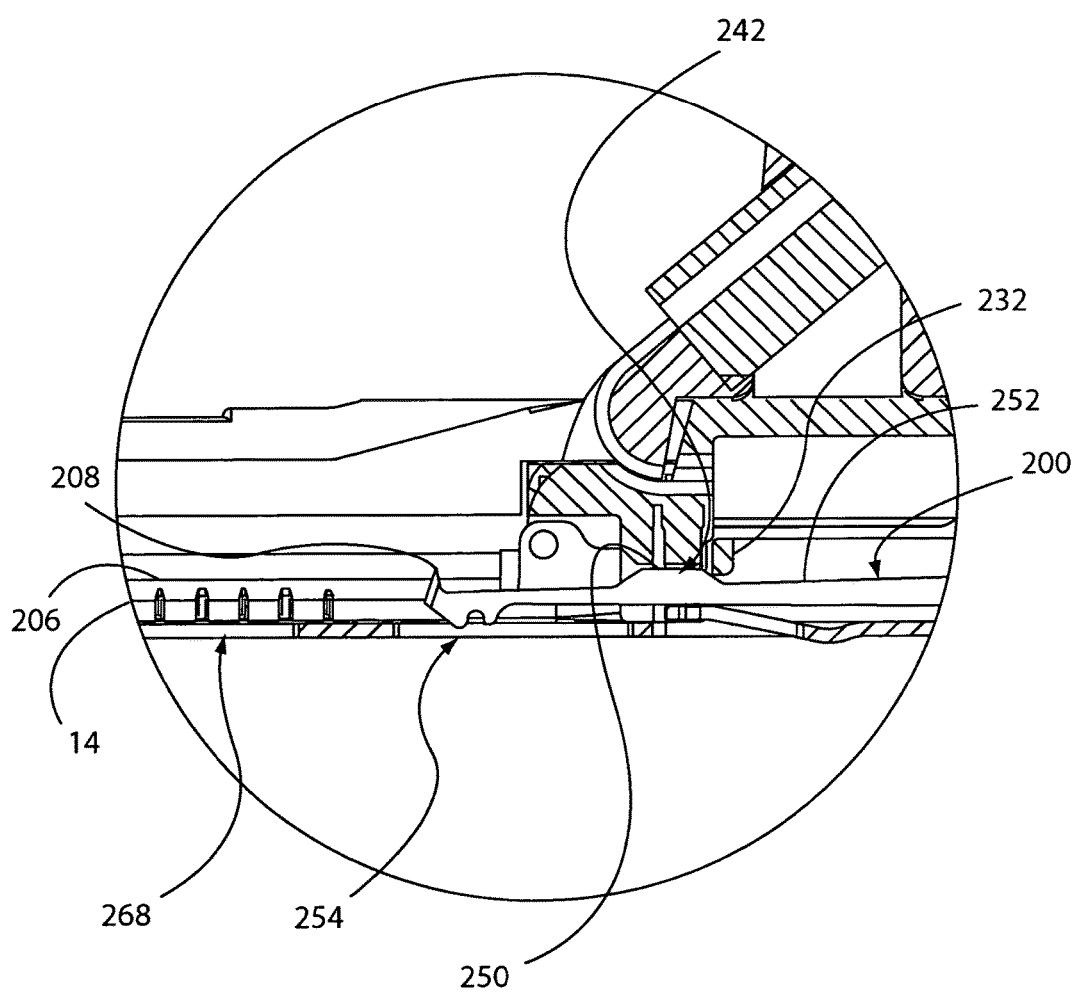
FIG. 52 is a side cutaway view of the anvil and staple holder of FIG. 40, where the cutter is in a third position.

Referring also to FIG. 52, the cutter 200 continues to advance distally as the receiver 218 continues to impel the engagement feature 216 distally. Thus, the first cam follower 242 of the cutter 200 advances distally relative to the cam 232. As described above, at least the distal end of the cutter 200 is biased upward. The first cam follower 242 decreases in height at its proximal end. Thus, as the upwardly-biased first cam follower 242 moves distally relative to the cam 232, the cam 232 and the first cam follower 242 gradually disengage, causing both the distal end of the cutter 200 and the projection 208 to move upward. The first cam follower 242 is constructed to provide a smooth, gradual upward motion of the distal end of the cutter 200 and the projection 208, such as by providing a gradual slope between an upper surface 250 of the first cam follower 242 and an upper surface 252 of the cutter 200. Alternately, the first cam follower 242 may be constructed to allow the distal end of the cutter 200 and the projection 208 to abruptly snap upward as the first cam follower 242 moves distal to the cam 232.

As the distal end of the cutter 200 moves upward, the projection 208 moves upward through the upper opening 248 in the anvil arm 14. The contact surface 206 of the anvil arm 14 is adjacent to the inner surface of the wall of the target vessel. Thus, upward motion of the projection 208 through the upper opening 248 causes the projection 208 to enter the wall of the target vessel. The projection 208 is sized, and the first cam follower 242 and cam 232 are shaped, such that the upward motion of the projection 208 after the first cam follower 242 has moved distal to the cam 232 causes the projection 208 to completely penetrate through the wall of the target vessel. That is, at least a portion of the projection 208 passes through the wall of the target vessel and enters the lumen. This initial penetration of the wall of the target vessel defines the starting point of an arteriotomy performed on the target vessel by the projection 208. The starting point of the arteriotomy is spaced apart from the location on the target vessel at which the anvil arm 14 is inserted, resulting in a tissue bridge therebetween.

Figure 53:
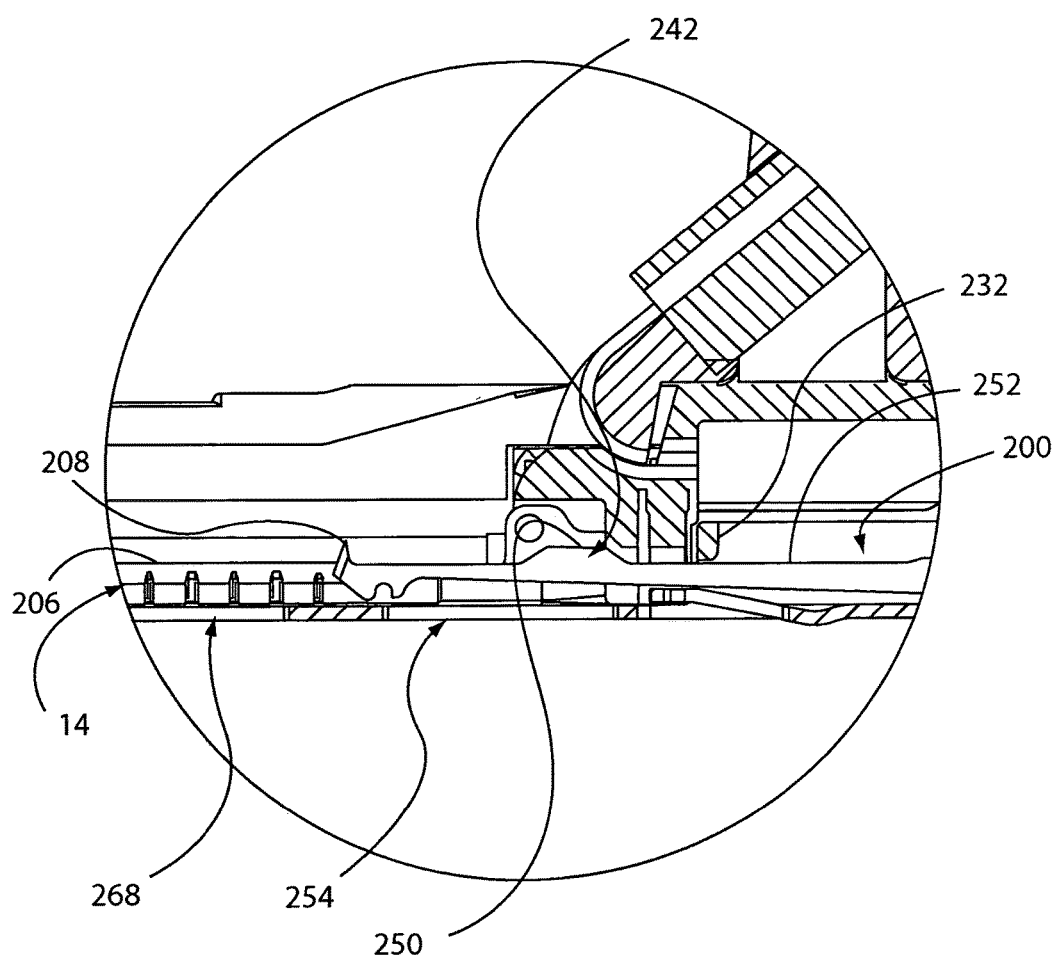
FIG. 53 is a side cutaway view of the anvil and staple holder of FIG. 40, where the cutter is in a fourth position.

Referring also to FIG. 53, the cutter 200 continues to advance distally as the receiver 218 continues to impel the engagement feature 216 distally. The upper surface 252 of the cutter 200 may contact the cam 232 during this motion, because the distal end of the cutter 200 continues to be biased upward. As the cutter 200 translates, the projection 208 moves through the tissue of the wall of the target vessel in a direction substantially parallel to the longitudinal centerline of the anvil arm 14. In this way, the projection 208 incises the tissue of the wall of the target vessel to create an arteriotomy. The tip of the projection 208 may maintain substantially the same height relative to the contact surface 206 of the anvil arm 14 during its distal translation, or may change its height relative to the contact surface 206 of the anvil arm 14, as long as the tip of the projection 208 remains in the lumen of the target vessel during that translation.

Figure 54:
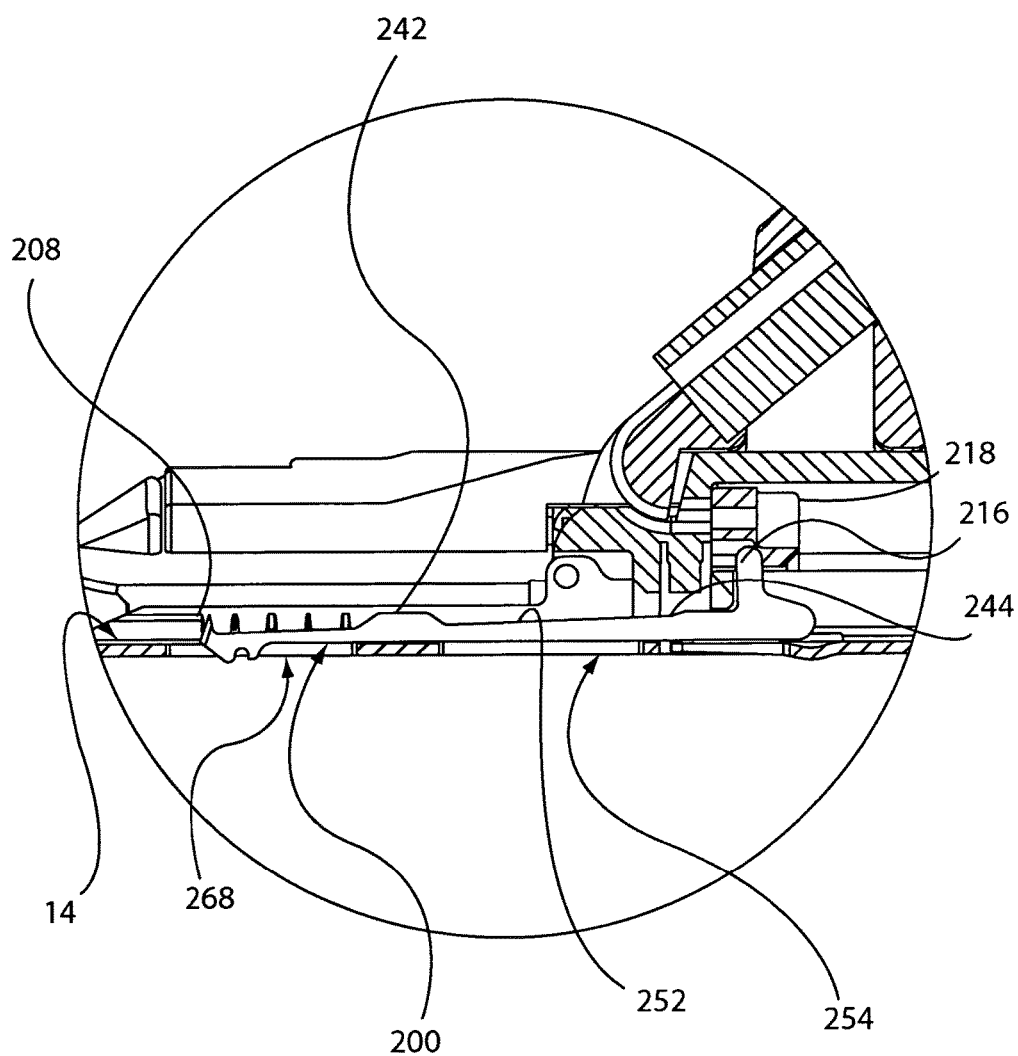
FIG. 54 is a side cutaway view of the anvil and staple holder of FIG. 40, where the cutter is in a fifth position.

Referring also to FIG. 54, a second cam follower 244 is defined on the upper surface 252 of the cutter 200, proximal to and spaced apart from the first cam follower 242. Alternately, a single cam follower is defined on the upper surface 252 of the cutter 200, where that single cam follower includes a feature corresponding to the first cam follower 242, a feature corresponding to the second cam follower 244, and a section of reduced height between them corresponding to the upper surface 252 of the cutter 200. The cutter 200 continues to advance distally as the receiver 218 continues to impel the engagement feature 216 distally. As a result of this motion, the second cam follower 244 contacts the cam 232. Engagement between the second cam follower 244 and the cam 232 pushes the distal end of the cutter 200 downward. The shape and size of the second cam follower 244 and cam 232 are selected such that the distal end of the cutter 200 is pushed downward far enough to cause the projection 208 to retract into the upper opening 248. The projection 208 may be urged downward completely into the channel 246, depending on the depth of the channel 246 and the height of the projection 208. Alternately, the upper tip of the projection 208 may remain within the upper opening 248. The cutter 200 may stop its distal translation at substantially the same time that the projection 208 retracts completely into the upper opening 248, or may continue to translate distally within the channel 246 before coming to a stop.

When the projection 208 is retracted out of the tissue of the wall of the target vessel, the distal end of the arteriotomy is defined, and the arteriotomy is complete. The distance between the first cam follower 242 and the second cam follower 244, and the shape of the cam followers 242, 244, determine the length of the arteriotomy. That is, each cam follower 242, 244 includes a location thereon having a height relative to the upper surface 252 of the cutter 200 sufficient to cause the projection 208 to be pushed out of contact with the wall of the target vessel. The distance between these locations defines the length of the arteriotomy. Thus, the cam followers 242, 244 control the motion of the projection 208 and control the penetration of the wall of the target vessel.

After performing the arteriotomy, the cutter 200 is in a distally-extended position. The cutter 200 remains in that position as the anvil arm 14 is removed from the target vessel. Alternately, after performing the arteriotomy, the cutter 200 may be moved proximally within the channel 246 before removing the anvil arm 14 from the target vessel. The anvil arm 14 is removed from the target vessel after the anastomosis between the graft vessel and the target vessel has been completed. The hole at the puncture site and its closure are substantially as described above.

Alternately, the cutter 200 is initially in a distally-extended position, and retracted proximally in order to make an incision in the wall of the target vessel. Similarly, the sled 482 is initially at its most distal location. The structures and mechanisms are substantially as described above, but operated in substantially the reverse order as described above. In this embodiment, the channels 496 in the staple holder 38 are not needed, nor it is necessary to reverse the direction of motion of the second cable 490 as applied to the sled 482; rather, the sled 482 is deployed by pulling it proximally with the second cable 490. Thus, the second cable 490 may be connected to the proximal end or other portion of the sled 482. Alternately, the cutter 200 and the projection 208 may be moved in a different way in order to incise the tissue of the wall of the target vessel. Further, this embodiment is particularly suited for the use of a cutter 200 having a sharp distal end that initially extends out of the distal end of the anvil arm 14 in order to puncture the target vessel, after which the cutter 200 is retracted proximally to move its sharp distal end into the anvil arm 14.

Where multiple projections 208 are provided on the cutter 200 as shown in FIGS. 39-43, the cutter 200 need not be translated as far to make an incision in the wall of the target vessel as it would if only a single projection were used. Because the projections 208 are spaced apart from each other along the direction of translation of the cutter 200, each projection 208 is able to form a portion of the incision during translation of the cutter 200. Thus, by translating each projection 208 across a distance less then the intended length of the entire incision, the complete incision can be formed. The distance that the cutter 200 is translated to form the incision is related to the distance between the projections 208. That is, because each projection 208 forms a portion of the incision, no single projection 208 need be translated along the entire length of the incision.

Alternately, where multiple projections 208 are utilized, the projections 208 may be inserted into the wall of the target vessel, after which energy is applied to the projections 208 via the cutter 200 or directly in order to create an incision in the wall of the target vessel. In such an embodiment, an energy source (not shown) is connected to the cutter 200. For example, an ultrasound generator (not shown) may be connected to the cutter 200 and to the energy source. The ultrasound generator may be a piezoelectric crystal, as is standard, or a different structure or mechanism. Electrical energy may be applied to the ultrasound generator from the energy source, thereby causing the ultrasound generator to vibrate the projections 208. Thus, energy may be applied from the energy source to the ultrasound generator after the projections 208 have been inserted into the wall of the target vessel, causing the projections 208 to move and thereby create an incision. Advantageously, a plurality of projections 208 spaced relatively close to one another are utilized. Other methods may be used to vibrate, move or oscillate the projections 208.

Alternately, the length of the arteriotomy created by and the number of connectors 464 deployed by the tissue effector 400 are adjustable. By controlling these parameters, graft vessels of different diameters can be attached to a target vessel within a small range of angles relative to the graft vessel. The cross-sectional area of the connection between the graft vessel and the target vessel thus can be controlled across a range of two or more sizes while providing for a substantially fixed angle between the target vessel and the graft vessel.

The number of connectors 464 deployed by the tissue effector 400 can be controlled in any appropriate manner. As one example, by varying the stroke of the sled 482 and therefore the length along each passage 440 that is traversed by the corresponding ramp element 446 of the sled 482, the number of connectors 464 deployed as a result of motion of the sled 482 can be controlled. Control of the stroke of the sled 482 may be accomplished in any appropriate manner. For example, a control (not shown) connected to the handle 302 may allow the selection of a particular number of connectors 464 for deployment. Such a control may interact with the second cable 490 and/or other components of or connected to the handle 302, in order to restrict the length that the second cable 490 moves upon actuation. By restricting the motion of the second cable 490, the stroke of the sled 482 is controlled, and hence the number of connectors 464 deployed is controlled. As another example, a set of controllable stops (not shown) may be provided within the tissue effector 400. Each stop is positioned in proximity to a connector bay 448, and is moveable between a first position that is out of the passage 440 adjacent to the connector bay 448 and a second position that is at least partially into the passage 440. In the second position, the stop contacts and prevents further distal motion of the corresponding ramp element 446 of the sled 482. The control interacts with the stops, such that when the control is used to select a particular number of connectors 464 for deployment, at least one stop is moved to its second position into a passage 440 of the tissue effector 400. Each stop that is moved to its second position corresponds to the connector bay 448 from which the last of the selected number of connectors 464 is to be deployed. Other mechanisms, structures or methods may be used to control the number of connectors 464 that are deployed.

Similarly, the length of the arteriotomy is controlled to correspond to the length of tissue that is connected by the selected number of connectors 464. The length of the arteriotomy can be controlled by controlling the motion of the cutter 200. The motion of the cutter 200 can be controlled in several ways. As one example, the openings 254, 268 in the anvil arm 14 can be changed both in length and position, to ensure that the arteriotomy is made to the correct length in the correct position. The openings 254, 268 can be changed in length and position in any appropriate manner. As one example, one or more pins or other structures (not shown) are extendable laterally across the openings 254, 268, such that the presence of those pins or other structures across the openings 254, 268 effectively changes their length and position. Other mechanisms, structures or methods may be used to control the length and position of the openings 254, 268 and/or the motion of the cutter 200.

Figure 17:
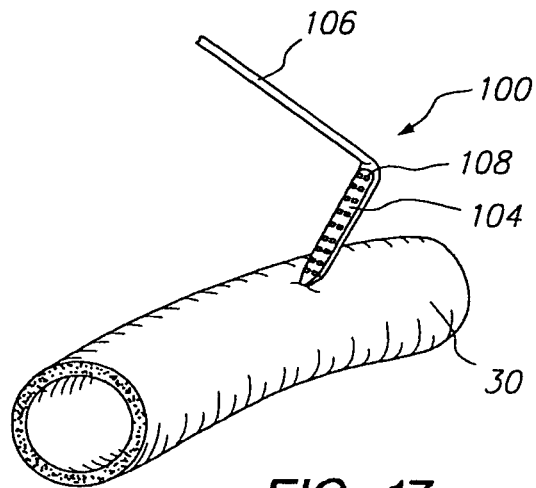
FIG. 17 is a perspective view of an anvil according to a second aspect of the invention being inserted into a target vessel.
Figure 18:
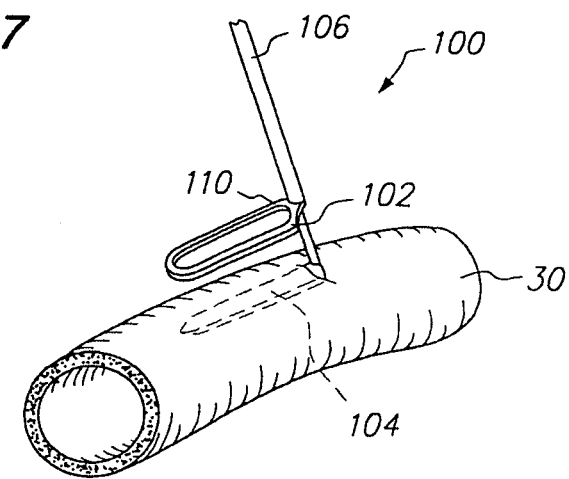
FIG. 18 is a perspective view of the anvil of FIG. 17 positioning inside a target vessel and a clamp being advanced to clamp the wall of the target vessel between the anvil and the clamp.

FIGS. 17-23 illustrate an alternate anvil 100 that is used with a clamp 102 for controlling an incision site during an anastomosis procedure. As shown in FIGS. 17 and 18, the anvil 100 includes an anvil arm 104 and a handle 106. The clamp 102 is slidable on the handle 106 to clamp the tissue of the target vessel 30 between the clamp 102 and the anvil arm 104. As with the anvil arm 104 described above, the anvil arm 104 includes two rows of staple bending features 108 in the form of recesses positioned in two parallel rows along a top surface of the anvil arm 104. The clamp 102 has a central opening 110. Once the tissue of the target vessel wall has been trapped between the clamp 102 and the anvil arm 104, an incision may be made through the target vessel wall and the edges of the incision are controlled by the combination of the anvil arm 104 and the clamp 102.

Figure 19:
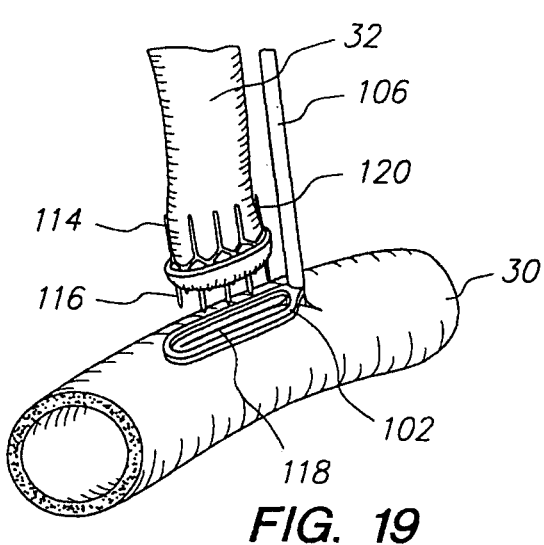
FIG. 19 is a perspective view of a graft vessel being advanced to the target vessel with a continuous anastomosis staple while the anastomosis site on the target vessel is controlled by the anvil and clamp.

As shown in FIG. 19, a continuous anastomosis staple device 114 may be used to connect the graft vessel 32 to the target vessel 30 at the anastomosis site. The staple device 114 as shown in FIG. 19 includes a plurality of linkages forming a tubular configuration and a plurality of staple ends extending from the linkages. FIGS. 20-22 illustrate how the staple ends 116 of the staple device 114 are positioned in the end of the graft vessel 32 and are inserted through the incision 118 in the target vessel and bent over by contact with the staple bending features 108 of the anvil. As shown in FIG. 22, the opposite ends 120 of the staple device 114 are folded over to complete the anastomosis. FIG. 23 illustrates a completed anastomosis performed according to the steps illustrated in FIGS. 19-22.

Figure 26:
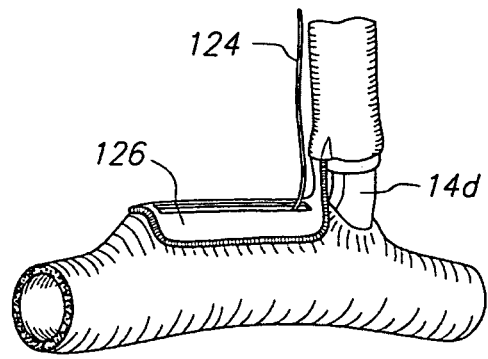
Figure 27:
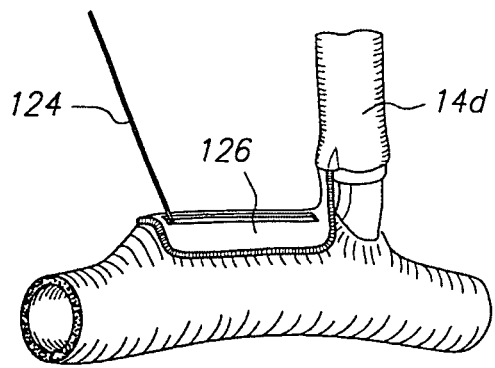

FIGS. 24-27 illustrate an alternate example of an anvil arm 14*d* having a cutting wire 124 for forming the incision in the wall of the target vessel 30. The cutting wire 124 may be used to form an incision before, during or after performing an end-to-side anastomosis procedure. Referring particularly to FIGS. 26-27, for forming the incision after the anastomosis procedure, a clamp 126 is used to trap the tissue at the anastomosis site between the clamp 126 and the anvil arm 14*d* prior to performing the incision. The incision is spaced apart from the entry point of the anvil arm 14*d* into the target vessel, creating a tissue bridge between the incision made in the wall of the target vessel and the entry point of the anvil arm 14*d* into the target vessel. A portion of the contact between the anastomosed graft vessel and target vessel extends across the tissue bridge, such that the incision is located within the closed area defined by the contact between the perimeter of the end of the graft vessel and the wall of the target vessel.

Figure 28:
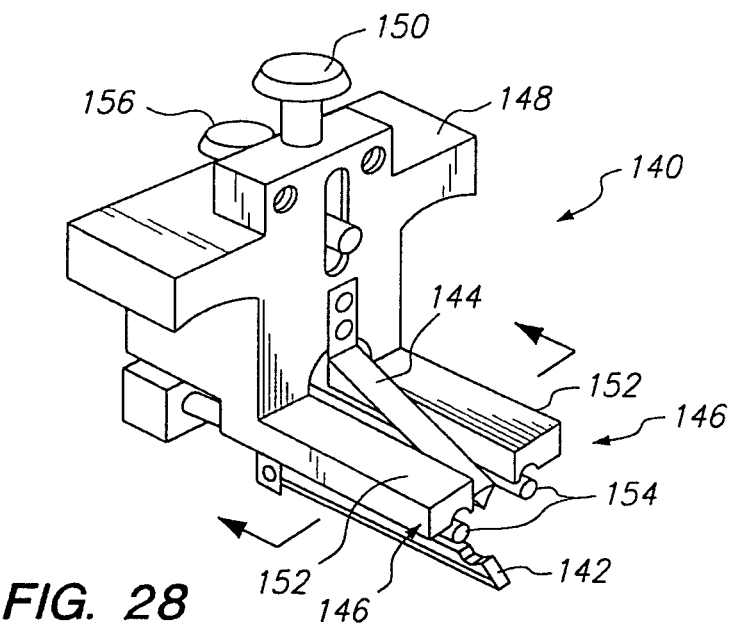
FIG. 28 is a perspective view of a system for controlling a tissue site and performing anastomosis according to the present invention.

FIG. 28 shows a system 140 for controlling a tissue site and performing anastomosis. For purposes of clarity, the staple holder and staples have been omitted from FIG. 28. The system 140 includes an anvil arm 142, a cutter 144, and a graft vessel holder 146 all mounted on a handle 148. The anvil arm 142 is mounted on the handle 148 and connected to a first actuator 150 that allows the anvil to be moved downward against the bias of a spring inside the handle. The cutter 144 may be spring biased or fixed and is positioned on the handle 148 directly above the anvil arm 142. The graft vessel holder 146 includes two fixed arms 152 and two movable arms 154. The two movable arms 154 are connected to a second actuator 156 on the handle 148. Depression of the second actuator 156 against the bias of a spring within the handle causes the movable arms 154 to be moved downward away from the fixed arms to receive portions of a graft vessel between the movable and fixed arms.

The operation of the system 140 of FIG. 28 is shown in the cross sectional views of FIGS. 29-31. As shown in FIG. 29, an end of a graft vessel 32 is split so that each half of the graft vessel 32 can be held between a fixed arm 152 and a movable arm 154. In order to load the graft vessel 32 into the system 140, the first actuator 150 and the second actuator 156 are depressed to move the anvil arm 142 and the movable arms 154 downward. The split graft vessel 32 is then inserted between the fixed and movable arms 152, 154 and the second actuator 156 is released to trap the ends of the graft vessel 32, as shown in FIG. 30. The anvil arm 142 is then inserted into the target vessel 30 in the same or similar manner as described above.

Once the anvil has been inserted in the target vessel 30 as shown in FIG. 30, the first actuator 150 is released to allow the anvil to move upward to tent the wall of the target vessel. FIG. 31 illustrates the tented target vessel 30 positioned adjacent the split and trapped graft vessel 32 in a position for performing anastomosis. The staple holders 38 are then advanced in the direction of the arrows D toward opposite sides of the anvil to staple the graft vessel and target vessel together. The staple holders 38 may hold a staple strip with an expandable backbone as shown in FIGS. 10A and 10B, or may instead or additionally hold different types of staples not connected to a backbone. The staple holders 38 may be provided with movable pins which allow the spacing between the staples to be adjusted depending on a size of the graft vessel used. Once the staples have been placed, the anvil arm 142 is removed and the cutter 144 makes an incision in the target vessel before or during removal of the anvil.

As described above, staple bending features are provided on the anvil and staples are provided at an exterior of the tissue. Alternately, the staples and/or staple holding strips may be positioned on the anvil and an exterior member with staple bending features may be moved toward the anvil to bend the ends of the staples and secure the graft and target vessels together.

Figure 32:
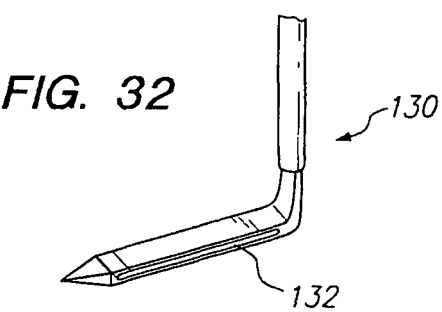
FIG. 32 is a perspective view of an anvil according to another aspect of the present invention for use with sutures.
Figure 33:
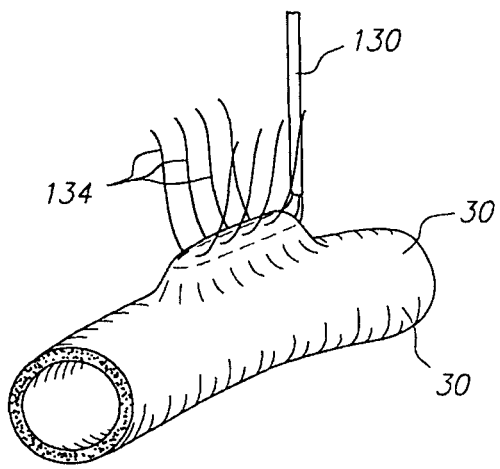
FIG. 33 is a perspective view of the anvil of FIG. 32 positioned within a target vessel and used to locate a plurality of suture at an anastomosis site.

FIGS. 32-33 illustrate the use of an alternate anvil 130 for controlling the tissue at an anastomosis site. The anvil 130 includes a longitudinal opening 132 extending through the anvil 130 for application of a plurality of conventional sutures at the anastomosis site. According to this method, the anvil 130 is inserted into the target vessel 30 and pulled against the interior wall of the target vessel 30, tenting the target vessel as shown in FIG. 33. Sutures 134 are then passed through the opening 132 in the anvil 130 and through the tissue of the target vessel wall on opposite sides of the anvil 130. Once the sutures 134 are placed as shown in FIG. 33, an incision is made in the target vessel along a center of the anvil 130. A center portion of each of the sutures 34 is then pulled out through the incision in the target vessel and cut so that an even row of sutures is provided along each of the sides of the incision. This system eliminates the tedious procedure of placing each individual suture very close to the edge of the incision in the very thin and flexible target vessel wall. Each of the sutures 134 is connected to a graft vessel in a conventional manner completing the anastomosis. The anvil as shown in FIGS. 32-33 allows quick and easy placement of a plurality of sutures in a very even manner close to the edge of the incision. For example, the sutures of a conventional anastomosis are generally within about one millimeter of the edge of the incision and are advantageously within 0.5 millimeters of the edge of the incision.

In an alternate embodiment, the cutter 200 does not include one or more projections 208. Instead, the cutter 200 includes or is connected directly or indirectly to an energy source (not shown), which is used to create an opening in the wall of the target vessel. For example, an emitter of laser or RF energy, or another type of energy, may be connected to the cutter 200 and to the energy source. As the cutter 200 translates along the anvil arm 14, it translates the emitter of laser or RF energy relative to the wall of the target vessel. The emitter of laser or RF energy is selectively actuated to transmit energy into the wall of the target vessel during translation of the cutter 200, thereby creating an opening therein. The energy source may transmit a first type of energy to the emitter or other mechanism, which is converted by the emitter into a second type of energy delivered into the wall of the target vessel. Alternately, the cutter 200 may include a projection 208 and additionally be connected to an energy source that is selectively actuated in order to assist in creating an opening in the wall of the target vessel.

In an alternate embodiment, the cutter 200 does not translate through the anvil arm 14. Instead, the cutter 200 is spatially removed from the anvil arm 14, and creates an opening in the wall of the target vessel before or after the anvil arm 14 is inserted into the target vessel. In one example of such an embodiment, the anvil arm 14 is inserted into a hole in the wall of the target vessel and the staple holder 38 deploys staples or other connectors to connect the graft vessel to the target vessel, as described above. The anvil arm 14 is removed, and an independent cutter 200 is then introduced through the hole in the wall of the target vessel. The cutter 200 may be configured as described above, including a projection 208 extending therefrom, or may be configured differently. The cutter 200 is manipulated relative to the connection between the target vessel and the graft vessel to create an opening at the junction therebetween. That is, registration is maintained between the cutter 200 and the junction between the end of the graft vessel and the wall of the target vessel. In order to position and manipulate the cutter 200 to create an opening at the location of the junction between the target vessel and the graft vessel, an imaging device (not shown) or other device may be connected to the cutter 200 or utilized in conjunction with the cutter 200. For example, a standard intravascular ultrasound unit may be connected to or used in conjunction with the cutter 200. The intravascular ultrasound unit is connected to a display device (not shown) visible to the operator. The operator controls the intravascular ultrasound unit to visualize the interior of the target vessel and the surrounding area, thereby locating the junction between the target vessel and the graft vessel and allowing the cutter 200 to be controlled to incise an opening in the wall of the target vessel within the closed area on the wall of the target vessel defined by the perimeter of the end of the graft vessel, thereby allowing blood to flow through the opening into the target vessel. A different visualization device or devices may be inserted into or positioned outside of the target vessel to locate the junction with the graft vessel. The cutter 200 and any visualization device present in the lumen of the target vessel are then removed from the lumen of the target vessel, and the opening in the wall of the target vessel through which they were removed is sealed.

In another example of such an embodiment, the anvil arm 14 is inserted into a hole in the wall of the target vessel and the staple holder 38 deploys staples or other connectors to connect the graft vessel to the target vessel, as described above. The anvil arm 14 is removed, and the hole in the wall of the target vessel is removed. A cannula (not shown) is inserted into the lumen of the graft vessel through the free end of the graft vessel, and a stylet (not shown) is inserted through the lumen of the cannula. The cannula and the stylet are surgical instruments that are well known in the art. The stylet has a distal end configured to penetrate the wall of the target vessel. Thus, a sharp point, blade, or other penetrating member may be formed into or connected to the distal end of the stylet. The cannula may be inserted into the lumen of the graft vessel such that its distal end contacts the outer wall of the target vessel. After the stylet has been inserted into the cannula, a force is exerted on the stylet to cause its distal end to penetrate the wall of the target vessel. Consequently, an opening is created between the graft vessel and the target vessel within the circumference of the end of the graft vessel. The cannula and stylet are then removed from the lumen of the graft vessel through its free end.

In another example of such an embodiment, the anvil arm 14 is inserted into a hole in the wall of the target vessel and the staple holder 38 deploys staples or other connectors to connect the graft vessel to the target vessel, as described above. The anvil arm 14 is removed, and the hole in the wall of the target vessel is closed. An independent cutter 200 is then introduced through the wall of the graft vessel. The cutter 200 itself may create an opening in the wall of the graft vessel through which it can enter, or a separate implement may be used to create an opening in the wall of the graft vessel. The cutter 200 may be configured as described above, including a projection 208 extending therefrom, or may be configured differently. For example, the cutter 200 may be J-shaped or L-shaped to facilitate creation of the opening between the graft vessel and the target vessel through the wall of the graft vessel. The cutter 200 is manipulated relative to the connection between the target vessel and the graft vessel to create an opening in the wall of the target vessel at the junction therebetween. That is, registration is maintained between the cutter 200 and the junction between the end of the graft vessel and the wall of the target vessel. The cutter 200 is then removed through the wall of the graft vessel, and the opening in the wall of the graft vessel is sealed.

While the invention has been described in detail, it will be apparent to one skilled in the art that various changes and modifications can be made and equivalents employed, without departing from the present invention. For example, the tissue effector 400 may be connected directly to the handle 302 without an intervening shaft 304, in a substantially rigid or substantially non-rigid manner. As another example, the mechanisms within the handle 302 may be reversed or otherwise rearranged, while maintaining their ability to actuate the tissue effector 400. It is to be understood that the invention is not limited to the details of construction, the arrangements of components, and/or the process of performing anastomosis set forth in the above description or illustrated in the drawings. Further, the invention is not limited to the performance of anastomosis in the context of a CABG procedure, nor it is limited to the anastomosis of two bodily vessels. Other tissue structures than vessels may be connected together within the body utilizing the present invention. Therefore, the invention is not to be restricted or limited except in accordance with the following claims and their legal equivalents.

What is claimed is:

1. A surgical tool for performing anastomosis between a graft vessel and a target vessel, comprising:
a handle;
a tissue effector including an anvil,
   a plurality of staples, and
   a staple holder connected to and movable relative to said anvil, wherein said staple holder includes two arms extending at least partly longitudinally,
   wherein each said arm holds a plurality of said staples, said staple holder defining a non-closed perimeter such that said arms are free and disconnected from one another at distal ends thereof to define an open-ended gap therebetween that extends longitudinally at least from said distal ends of said arms to a location of a proximal most said staple held by said arms, and wherein said arms are spaced apart from and fixed relative to one another along their entire length during deployment of said staples;
a cutting element having a base positioned in and moveable along a channel defined within the anvil, wherein a tip of the cutting element extends from the anvil into the open-ended gap between the two arms of the staple holder; and
a shaft connected to said handle and to said tissue effector, wherein at least part of said shaft is flexible.

2. The surgical tool of claim 1, wherein all of said shaft is flexible.

3. The surgical tool of claim 1, wherein said tissue effector is orientable in a plurality of different positions relative to said handle.

4. The surgical tool of claim 1, wherein said staple holder is rotatable relative to said anvil.

5. The surgical tool of claim 1, further comprising at least one force transmission member connected to said handle and to said tissue effector.

6. The surgical tool of claim 5, wherein said shaft includes a lumen therethrough, and wherein said force transmission member extends through said lumen.

7. The surgical tool of claim 5, wherein said force transmission member is a cable.

8. The surgical tool of claim 1, wherein the length to width ratio of said anvil is at least 2:1.

9. The surgical tool of claim 8, wherein the length to width ratio of said anvil is less than 15:1.

10. The surgical tool of claim 1, further comprising: the handle connected to a proximal end of said shaft.

11. The surgical tool of claim 1, wherein said arms hold the graft vessel therebetween during deployment of said staples.

12. The surgical tool of claim 1, further comprising at least one connector bay defined in each said arm; wherein each said connector bay holds a corresponding said staple.

13. The surgical tool of claim 1, wherein said arms are substantially fixed relative to said anvil during deployment of said staples.

14. The surgical tool of claim 1, wherein the anvil is rotatable about a pivot.

15. The surgical tool of claim 1, wherein the cutting element is moveable in a direction parallel to a top of the channel.

16. The surgical tool of claim 1, wherein a portion of the cutting element extends from the channel.

17. The surgical tool of claim 1, wherein the base of the cutting element has a first polygonal cross-section, the channel has a second polygonal cross-section, and the first and second polygonal cross-sections provide a slidable fit of the base within the channel.

18. The surgical tool of claim 1, wherein the base of the cutting element and the channel defined within the anvil are configured for longitudinal movement of the cutting element along the anvil.

19. The surgical tool of claim 1, wherein the cutting element comprises a blade attached to the base, the blade configured to extend from and slide along the channel while the base slides within the channel.

* * * * *